(12) United States Patent
Sakai et al.

(10) Patent No.: US 7,125,984 B2
(45) Date of Patent: Oct. 24, 2006

(54) GLUCURONOFUCAN SULFATE

(75) Inventors: Takeshi Sakai, Hirosaki (JP); Kumiko Ishizuka, Hirosaki (JP); Kaoru Kojima, Hirosaki (JP); Kazuo Shimanaka, Takatsuki (JP); Katsushige Ikai, Shiga (JP); Ikunoshin Kato, Uji (JP)

(73) Assignee: Takara Bio Inc., Shiga (JP)

( * ) Notice: Subject to any disclaimer, the term of this patent is extended or adjusted under 35 U.S.C. 154(b) by 538 days.

(21) Appl. No.: 10/258,133

(22) PCT Filed: Apr. 19, 2001

(86) PCT No.: PCT/JP01/03333

§ 371 (c)(1),
(2), (4) Date: Oct. 21, 2002

(87) PCT Pub. No.: WO01/81560

PCT Pub. Date: Nov. 1, 2001

(65) Prior Publication Data

US 2003/0186389 A1    Oct. 2, 2003

(30) Foreign Application Priority Data

Apr. 21, 2000 (JP) .............................. 2000-121116
Jun. 21, 2000 (JP) .............................. 2000-186346

(51) Int. Cl.
*C08B 37/00* (2006.01)
*C12P 19/04* (2006.01)

(52) U.S. Cl. .................. 536/123; 536/123.1; 536/128; 435/99; 435/101; 435/72

(58) Field of Classification Search ................. 435/99, 435/101, 72; 536/123, 123.1, 128
See application file for complete search history.

(56) References Cited

U.S. PATENT DOCUMENTS 6,054,577 A    4/2000   Sakai et al.

6,207,652 B1    3/2001   Sakai et al.

FOREIGN PATENT DOCUMENTS

EP    0 965 323 A2 *    12/1999
EP    1 176 153 A1      1/2002

OTHER PUBLICATIONS

Hideyuki Shibata et al., "Anti-ulcer Effect of Fucoidan from Brown Seaweed, *Cladosiphon okamuranus* Tokida in Rats", Yakuri to Chiryou, (1998), vol. 26, No. 8, pp. 1211-1215.
Masakuni Takou et al., "Fucoidan is Available to be Prepared in Inustrial Scale from Okinawarnozuku (*Cladosiphon okamuranus* Tokida)", Synopses of Lectures at Glucide Symposium (1997), vol. 19, p. 20.
Masakuni Tako et al., "Isolation and Identification of Fucoidan from Okinawamozuku (*Cladosiphon Okamuranus* Tokida)", J. Appl. Glycoscl. (1996), vol. 43, No. 2, pp. 143-148.
Masato Nagaoka et al., "Structural Study of Fucoidan from *Cladosiphon okamuranus* Tokida", Glycoconjugate Jounral (1999), vol. 16, pp. 19-26.
Shinichi Furukawa, "Studies on the Fucoidan-Utilizing Microorganisms II", Bulletin of Hijiyama University Junior College (1990), vol. 24, pp. 159-165.
Takeshi Sakai et al., "Two Novel Enzymes from a Sea Bacterium, α-D-Glucoronidase and Endo-α-L-Fucosidase and their Use for the Analysis of the Structure of Fucoidan (Sulfated Glucuronofucan) from *Cladosiphon okamuranus*", Nippon Toushitsu Gakkai Nenkai Youshishuu (Jun. 2000), vol. 21, p. 64.
Annika Rylund et al., "Oligosaccharides Obtained by Enzymatic Hydrolysis of Birch Kraft Pulp Xylan: Analysis by Capillary Zone Electrophoresis and mass Spectrometry", *Carbohydrate Research*, (1997), vol. 300, pp. 95-102.
Karin Bronnenmeier et al., "x-D-Glucuronidases from the Xylanolytic Thermophiles *Clostridium Stercorarium* and *Thermoanaerobacterium saccharolyticum*", Microbiology, (1995), vol. 141, pp. 2033-2040.

* cited by examiner

*Primary Examiner*—Francisco Prats
(74) *Attorney, Agent, or Firm*—Browdy and Neimark, PLLC

(57) ABSTRACT

Three enzymes degrading sulfated glucuronofucan; processes for producing these enzymes; activators for these enzymes; glucuronofucan sulfate and degradation products thereof; and a novel microorganism.

3 Claims, 40 Drawing Sheets pH of Reaction Mixture (°C)

Temperature of Reaction Mixture (°C)

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial
<220> FEATURE:
<223> OTHER INFORMATION: Designed oligonucleotide primer to amplify 16S
      rDNA region.

<400> SEQUENCE: 1
agagtttgat cctggctcag                                              20

<210> SEQ ID NO 2
<211> LENGTH: 19
<212> TYPE: DNA
<213> ORGANISM: Artificial
<220> FEATURE:
<223> OTHER INFORMATION: Designed oligonucleotide primer to amplify 16S
      rDNA region.

<400> SEQUENCE: 2
ggctaccttg ttacgactt                                               19

<210> SEQ ID NO 3
<211> LENGTH: 1478
```

<212> TYPE: DNA
<213> ORGANISM: Fucophilus fucoidanolyticus SI-1234

<400> SEQUENCE: 3

| | | | | | |
|---|---|---|---|---|---|
| agtgaacgct | ggcggcgtgg | ttaagacatg | caagtcgaac | gagattcttt | gtattgaagc | 60 |
| ctcggtggat | ttataaagat | gaaagtggca | acgggtgcg | taacacgtga | gcaatctgcc | 120 |
| ctaaagatcg | gaatagctcg | aggaaactcg | aattaatgcc | ggatgtgata | cgccaactca | 180 |
| tgttggtagt | attaaagctt | gtaatggcgc | tttaggagga | gctcgcggcc | tatcagcttg | 240 |
| ttggtgaggt | aaaggctcac | caaggcaaag | acgggtagct | ggtctgagag | gatgatcagc | 300 |
| cacactggaa | ctgagacacg | gtccagacac | ctacgggtgg | cagcagtttc | gaatcattca | 360 |
| caatggggc | aaccctgatg | gtgcaacgcc | gcgtgaggga | tgaaggcctt | cgggtcgtaa | 420 |
| acctctgtca | ccagggagca | acaagcaggt | tcatagcctg | ccctgagtta | acctggagag | 480 |
| gaagcagtgg | ctaactccgt | gccagcagcc | gcggtaatac | ggagactgca | agcgttactc | 540 |
| ggattcactg | ggcgtaaagg | gtgcgtaggc | ggatagatgt | gtcaggtgtg | aaatctcggg | 600 |
| gctcaacctc | gaaactgcgc | ctgaaactgt | ctatctagag | tattggaggg | gtaagcggaa | 660 |
| tttctggtgt | agcggtgaaa | tgcgtagata | tcagaaggaa | caccaatggc | gaaggcagct | 720 |
| tactggacaa | atactgacgc | tgaggcacga | agcatgggt | agcgaaaggg | attagatacc | 780 |
| cctgtagtcc | atgccgtaaa | cgttgcacac | taggtcttgg | gggtttcgac | cctttcagga | 840 |
| ccccagctaa | cgcgataagt | gtgccgcctg | aggactacgg | ccgcaaggct | aaaactcaaa | 900 |
| ggaattgacg | ggggcccgca | caagcggtgg | agcatgtggt | ttaattcgat | gcaacgcgaa | 960 |
| gaaccttacc | taggcttgac | atgtaatgga | cgattttcag | agatgaattt | ttcccttcgg | 1020 |
| ggctgttaca | caggtgctgc | atggccgtcg | tcagctcgtg | tcgtgagatg | tttggttaag | 1080 |
| tccagcaacg | agcgcaaccc | tcgtccttag | ttgccagcac | gtaatggtgg | ggactctaag | 1140 |
| gagacaaact | ctctttgaga | gtgggaaggt | ggggatgacg | tcaggtcagt | atggccctta | 1200 |
| cgcctagggc | tacacacgtg | ctacaatgcc | cggtacaata | ggacgcaata | ccgcgaggtg | 1260 |
| gagcaaatcc | tcaaaaccgg | gcccagttcg | gattggagtc | tgcaactcga | ctccatgaag | 1320 |
| tcggaatcgc | tagtaatgac | gtatcagcta | tgacgtcgtg | aatacgttcc | cgggccttgt | 1380 |
| acacaccgcc | cgtcacatca | tgaaagccgg | ttttgcccga | agtacgtgag | ctatccctcg | 1440 |
| ggaggcagcg | tcctaaggca | gggctggtga | ttgggatg | | | 1478 |

GLUCURONOFUCAN SULFATE

TECHNICAL FIELD

The present invention relates to a novel bacterium useful for production of an enzyme that degrades many kinds of sulfated polysaccharides contained in brown algae, a sulfated glucuronofucan-degrading enzyme useful in a field of glycotechnology, a method for producing the enzyme, various factors that activate the enzyme, a deacetylated sulfated glucuronofucan, a deacetylated deglucuronylated sulfated glucuronofucan and a sulfated glucuronofucan oligosaccharide useful as reagents for glycotechnology, as well as methods for producing the same.

BACKGROUND ART

Brown algae contain many kinds of sulfated polysaccharides. For example, the following sulfated fucose-containing polysaccharides are known: (1) sulfated fucans which consist of fucose and sulfate groups; (2) sulfated fucoglucuronomannans which contain glucuronic acid, mannose, fucose and sulfate groups, e.g., the sulfated fucose-containing polysaccharide-U as described in WO 97/26896 (approximate molar ratio of constituting saccharides, fucose: mannose:galactose:uronic acid:sulfate group=10:7:4:5:20; hereinafter referred to as U-fucoidan); and (3) sulfated fucogalactans which consist of fucose and galactose, e.g., the sulfated fucogalactan as described in PCT/JP00/00965 (molar ratio of constituting saccharides, fucose:galactose=1: 1–6; hereinafter referred to as G-fucoidan).

These polysaccharides are generically called fucoidans or fucoidins. In many cases, their structures vary depending on the algae from which they derive. For example, sulfated polysaccharides extracted from *Fucus vesiculosus, Laminaria japonica* Areschoug, *Cladosiphon okamuranus* Tokida, *Nemacystus decipiens* (Suringar) Kuckuck and sporophyll of *Undaria pinnatifida* (Harvey) Suringar are known to have structures different each other. Almost all of these sulfated fucose-containing polysaccharides are macromolecular anions. Therefore, they behave in a chemically and physically similar manner in various purification steps, making it difficult to separate them each other. For this reason, in many cases, biological activities of sulfated fucose-containing polysaccharides derived from brown algae have been examined without separating them each other. For example, a sulfated fucan fraction has been reported to have a strong anticoagulant activity, whereas a sulfated fucoglucuronomannan fraction has been reported to have an apoptosis-inducing activity against tumor cells. However, it was difficult to identify the sulfated fucose-containing polysaccharide that was responsible for the observed biological activity.

If a physiologically active sulfated polysaccharide is to be developed as a pharmaceutical, it is necessary to determine its chemical structure. For this purpose, an enzyme that degrades the physiologically active sulfated polysaccharide is required. Similarly, if oligosaccharides are to be obtained from the above-mentioned sulfated polysaccharides, it is required to obtain enzymes that degrade the respective sulfated polysaccharides.

However, no enzyme that degrades a sulfated polysaccharide from brown algae is commercially available. In addition, a degrading enzyme that specifically degrades the sulfated polysaccharide of which the structure is to be determined is required. This is because, in many cases, sulfated polysaccharides from brown algae vary depending on the species of the algae. For example, a microorganism that utilizes a certain sulfated polysaccharide is often screened in order to obtain an enzyme that degrades the sulfated polysaccharide. In this case, a sulfated polysaccharide-degrading enzyme may be efficiently produced by isolating and identifying a microorganism that utilizes the sulfated polysaccharide, and examining culture conditions. However, it takes a long time to isolate and identify such a microorganism. Furthermore, it is not usual that a single microorganism utilizes more than one sulfated polysaccharides. Almost no microorganism is known to utilize sulfated polysaccharides from brown algae belonging to several orders or families.

Thus, it has been desired to produce a sulfated polysaccharide-degrading enzyme using an already identified and isolated microorganism, or to produce a several kinds of sulfated polysaccharide-degrading enzymes from a single microbial strain.

Recently, the following studies were reported with respect to a sulfated polysaccharide from *Cladosiphon okamuranus* Tokida: the polysaccharide inhibits colonization of *Helicobacter pyroli*, a gastric ulcer-causing microorganism, on tunica mucosa ventriculi; a complex of the polysaccharide with fibroblast growth factor can be used as an agent for promoting growth of fibroblasts; and infection with a bacterium, a virus or the like can be prevented by oral administration of the polysaccharide. Accordingly, relationships between physiological activities connected with *Cladosiphon okamuranus* Tokida and chemical structures of sulfated polysaccharides derived from *Cladosiphon okamuranus* Tokida have been studied. For example, there are two reports on the polysaccharides. One describes a sulfated glucuronofucan containing fucose, glucuronic acid, sulfate group and acetyl group with a molar ratio of 6.1:1.0:2.9:1 and having a molecular weight of about 56,000 (Glycoconjugate Journal, 16:19–26 (1999)). The other describes a sulfated glucuronofucan containing fucose, glucuronic acid, xylose, sulfate group and acetyl group with a molar ratio of 3–4:0.8–1.2:0.1–0.3:0.8–1.2:0.5–1 and having a molecular weight of about 500,000–600,000 (Oyo Toshitsu Kagaku (Journal of Applied Glycoscience), 43:143–148 (1996)). To date, only average values for the structures have been shown based on physicochemical analyses.

In addition, it is necessary to obtain an oligosaccharide having a uniform structure in order to develop a pharmaceutical or the like. However, it has been difficult to obtain an oligosaccharide having a uniform structure, for example, from a sulfated polysaccharide derived from *Cladosiphon okamuranus* Tokida.

For the reasons as described above, a microorganism that degrades many kinds of sulfated polysaccharides derived from brown algae, an enzyme that specifically degrades a sulfated polysaccharide derived from *Cladosiphon okamuranus* Tokida (i.e., a sulfated glucuronofucan) and a sulfated glucuronofucan oligosaccharide having a uniform structure produced by an enzymatic means have been desired.

OBJECTS OF INVENTION

The main object of the present invention is to provide a novel microorganism that degrades many kinds of sulfated polysaccharides derived from brown algae, three enzymes that degrade sulfated glucuronofucans which are useful for glycotechnology, methods for producing the enzymes, smaller molecules obtained by allowing the enzyme to act on a sulfated glucuronofucan, a method for producing the smaller molecules and an activator of a sulfated glucuronofucan-degrading enzyme.

SUMMARY OF INVENTION

As a result of intensive studies, the present inventors have successfully isolated a bacterium capable of utilizing plural sulfated polysaccharides derived from many kinds of brown algae, and designated the genus to which it belong as genus *Fucophilus*. The present inventors have also found that a bacterial strain belonging to genus *Fucophilus, Fucophilus fucoidanolyticus* strain SI-1234, produces three sulfated glucuronofucan-degrading enzymes, i.e., a fucoidan deacetylase, an α-D-glucuronidase and an endo-α-L-fucosidase. Methods for producing the enzymes have been found. Furthermore, the present invention have found that sodium chloride, a calcium salt and a protein are useful for the efficient utilization of the enzymes. Additionally, the present inventors have found a deacetylated sulfated glucuronofucan, a deacetylated deglucuronylated sulfated glucuronofucan and a sulfated glucuronofucan oligosaccharide having a uniform structure produced by an enzymatic means which can be utilized as reagents for glycotechnology as well as methods for producing them. Thus, the present invention has been completed.

The first aspect of the present invention relates to a fucoidan deacetylase having the following chemical and physical properties. The enzyme acts on a sulfated glucuronofucan and a sulfated glucuronofucan oligosaccharide and hydrolyzes an acetyl group to release acetic acid; has an optimal pH of about 6 to 9.1; and has an optimal temperature of about 23 to 45° C.

The second aspect of the present invention relates to an α-D-glucuronidase having the following chemical and physical properties. The enzyme acts on a deacetylated sulfated glucuronofucan and a sulfated glucuronofucan oligosaccharide and hydrolyzes an α-D-glucuronyl bond to release D-glucuronic acid; has an optimal pH of about 5.8 to 7.8; and has an optimal temperature of about 14 to 29° C.

The third aspect of the present invention relates to an endo-α-L-fucosidase having the following chemical and physical properties. The enzyme acts on a deacetylated deglucuronylated sulfated glucuronofucan and a sulfated glucuronofucan oligosaccharide and hydrolyzes an α-L-fucosyl bond in an endo-type manner to generate an oligosaccharide having L-fucose at its reducing end; has an optimal pH of about 4.5 to 7.5; and has an optimal temperature of about 23 to 42° C.

In the first to third aspects, the fucoidan deacetylase, the α-D-glucuronidase or the endo-α-L-fucosidase can be produced by culturing a microorganism capable of producing the enzyme and collecting the enzyme from the culture.

The fourth aspect of the present invention relates to a method for producing a deacetylated sulfated glucuronofucan, the method comprising allowing the fucoidan deacetylase of the first aspect to act on a sulfated glucuronofucan; and collecting a deacetylated sulfated glucuronofucan from which at least one acetyl group molecule is removed.

The fifth aspect of the present invention relates to a deacetylated sulfated glucuronofucan which is obtainable by the method of the fourth aspect, or a salt thereof.

The sixth aspect of the present invention relates to a method for producing a deacetylated deglucuronylated sulfated glucuronofucan, the method comprising allowing the α-D-glucuronidase of the second aspect to act on a deacetylated sulfated glucuronofucan; and collecting a deacetylated deglucuronylated sulfated glucuronofucan from which at least one glucuronic acid residue molecule is removed.

In the sixth aspect, deglucuronylation may be carried out in the presence of sodium chloride, a calcium salt and/or a protein.

The seventh aspect of the present invention relates to a deacetylated deglucuronylated sulfated glucuronofucan which is obtainable by the method of the sixth aspect, or a salt thereof.

The eighth aspect of the present invention relates to a method for producing a sulfated glucuronofucan oligosaccharide, the method comprising allowing a fucoidan deacetylase, an α-D-glucuronidase and an endo-α-L-fucosidase to act on a sulfated glucuronofucan; and collecting a sulfated glucuronofucan oligosaccharide. In this case, the fucoidan deacetylase, the α-D-glucuronidase and the endo-α-L-fucosidase may be allowed to act at the same time, or the fucoidan deacetylase, the α-D-glucuronidase and the endo-α-L-fucosidase may be allowed to act one after another in this order.

The ninth aspect of the present invention relates to a method for producing a sulfated glucuronofucan oligosaccharide, the method comprising allowing an α-D-glucuronidase and an endo-α-L-fucosidase to act on a sulfated glucuronofucan deacetylated by alkali treatment; and collecting a sulfated glucuronofucan oligosaccharide. In this case, the α-D-glucuronidase and the endo-α-L-fucosidase may be allowed to act at the same time. Alternatively, the α-D-glucuronidase may be first allowed to act before the endo-α-L-fucosidase is allowed to act.

In the eighth or ninth aspect, the method may be carried out in the presence of sodium chloride, a calcium salt and/or a protein.

The tenth aspect of the present invention relates to a sulfated glucuronofucan oligosaccharide which is obtainable by the method of the eighth or ninth aspect, or a salt thereof.

The eleventh aspect of the present invention relates to a saccharide having a chemical structure of one selected from the group consisting of general formulas (I) to (III), or a salt thereof:

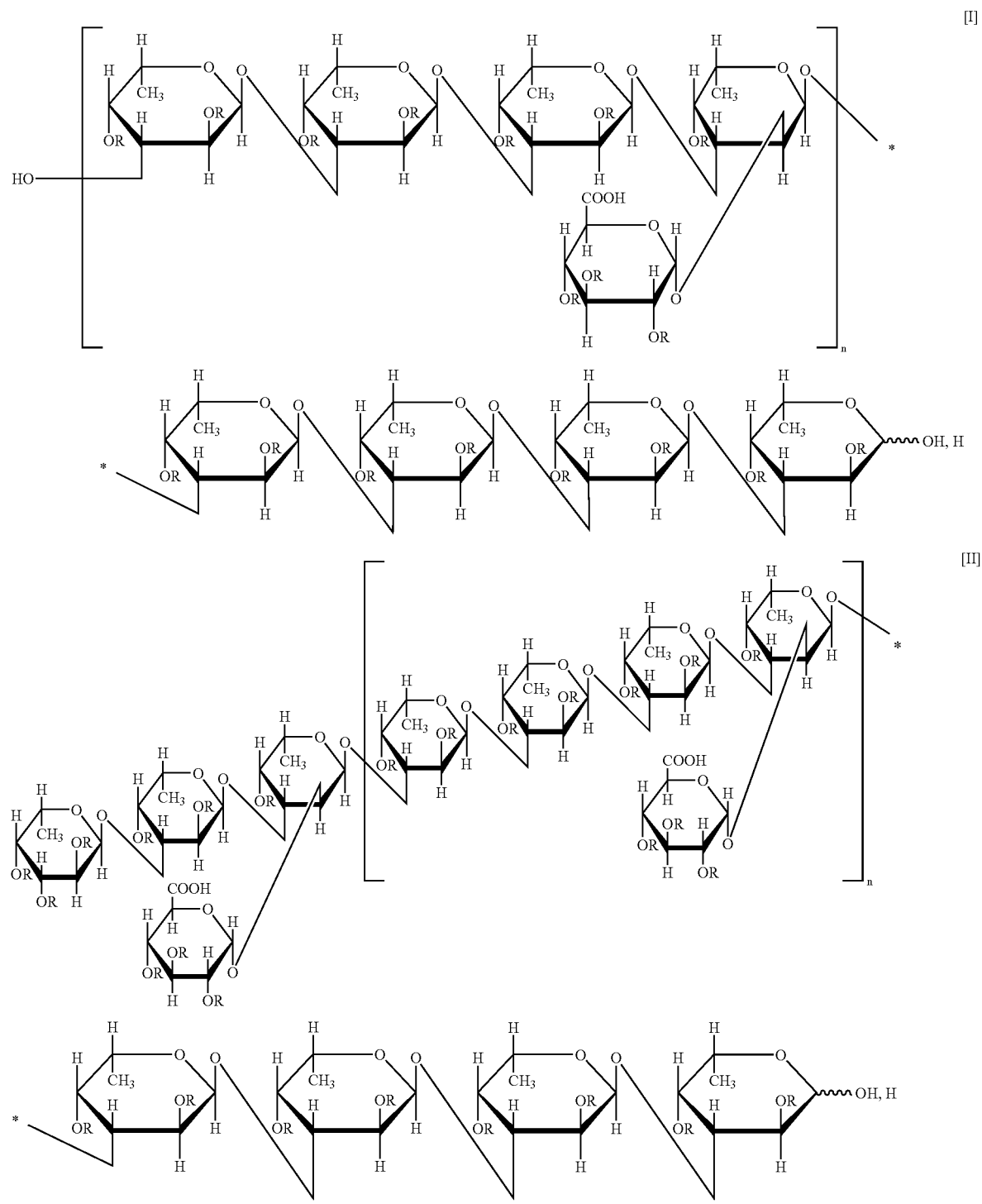

-continued

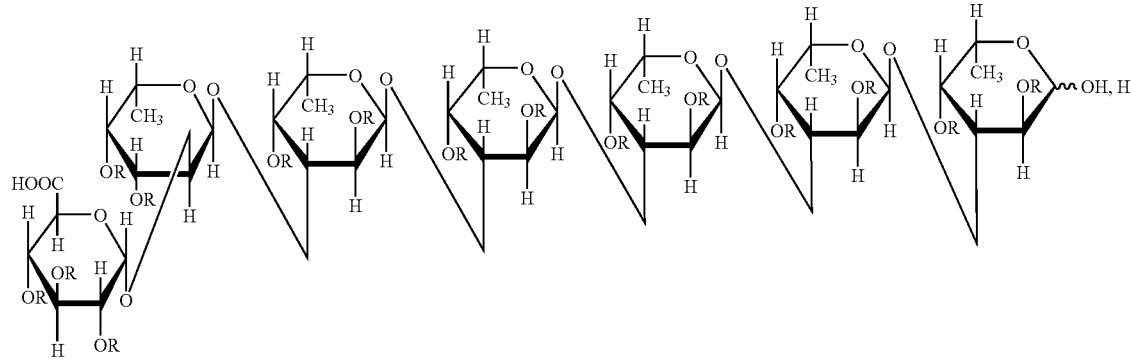

[III]

wherein R is H, SO₃H or CH₃CO; n is 0 or an integer of 1 or more.

The twelfth aspect of the present invention relates to a sulfated glucuronofucan having the following chemical and physical properties, or a salt thereof. An exemplary sulfated polysaccharide contains fucose and glucuronic acid as constituting saccharides at a molar ratio of 35:10 to 44:10; and contains a sulfated saccharide of general formula (VIII) as an essential component of the constituting saccharides:

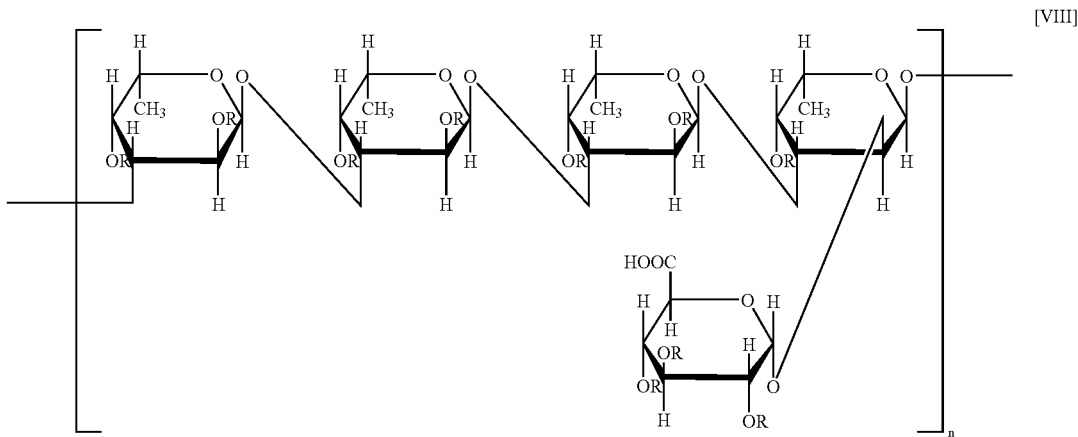

[VIII]

wherein R is H, SO₃H or CH₃CO.

In the twelfth aspect, n in general formula (VIII) is preferably from 1 to 5000.

The thirteenth aspect of the present invention relates to a bacterium belonging to genus Fucophilus capable of utilizing plural sulfated polysaccharides derived from brown algae.

In the thirteenth aspect, the bacteria belonging to genus *Fucophilus* include a bacterium which has menaquinone in its electron transport chain, and of which the GC content is about 50%, and a bacterium which contains a 16S ribosomal DNA having a nucleotide sequence with homology of 90% or more to the nucleotide sequence of 16S ribosomal DNA of SEQ ID NO:3. Although it is not intended to limit the present invention, *Fucophilus fucoidanolyticus* strain SI-1234 (FERM P-17517) is exemplified.

DETAILED DESCRIPTION OF THE INVENTION

Figure 1:
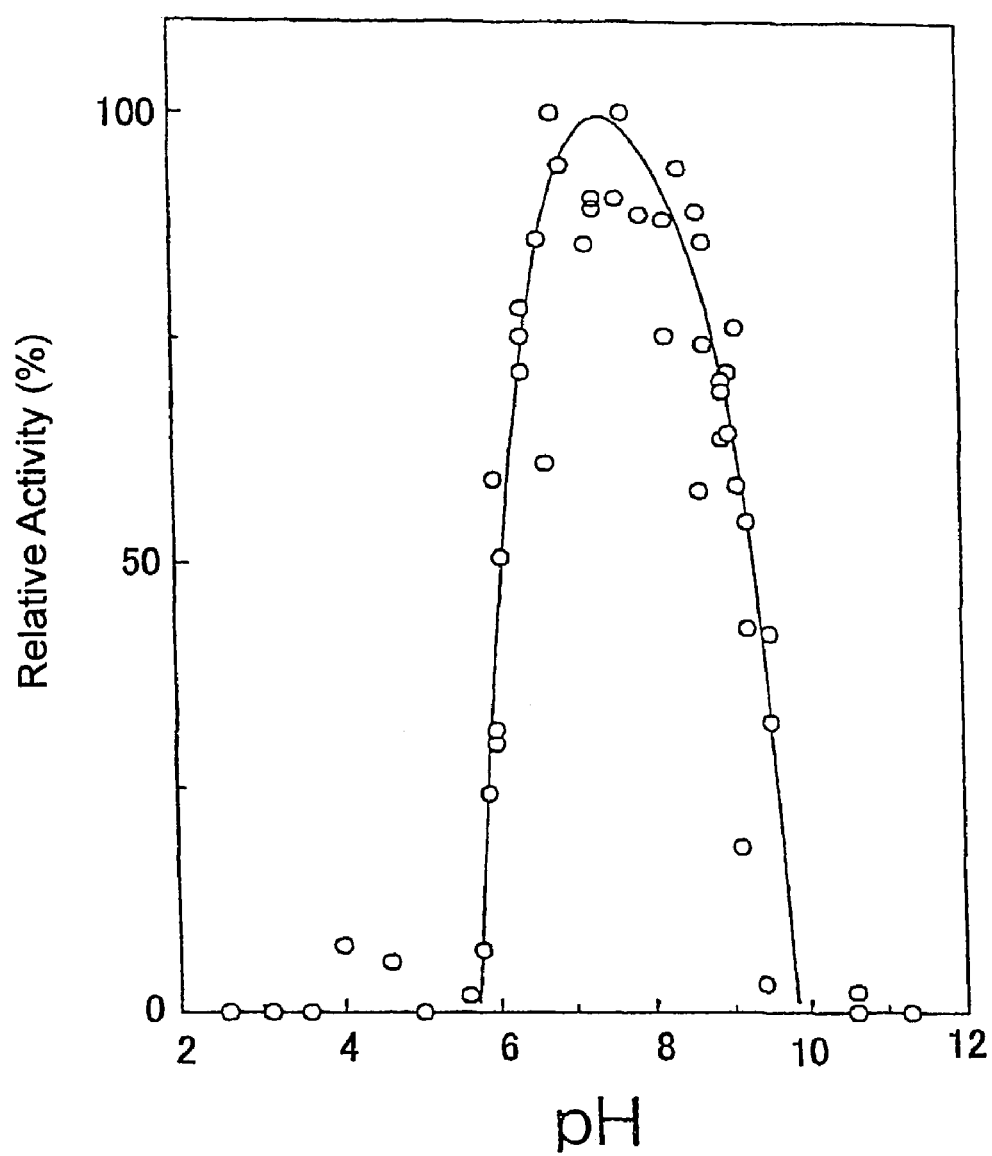
FIG. 1: a graph which illustrates the relationship between pH and the relative activity (%) of the fucoidan deacetylase according to the present invention.

The present invention will be explained in detail.

A bacterium belonging to genus *Fucophilus* according to the present invention may be any one capable of utilizing plural sulfated polysaccharides derived from brown algae. For example, a bacterium capable of utilizing one or more of sulfated polysaccharides derived from brown algae such as *Kjellmaniella crassifolia* Miyabe, *Laminaria japonica* Areschoug, *Undaria pinnatifida* (Harvey) Suringar, *Nemacystus decipiens* (Suringar) Kuckuck, *Cladosiphon okamuranus* Tokida, *Lessonia nigrescens, Fucus vesiculosus* and *Ascophyllum nodosum* can be preferably used. As used herein, utilization refers to incorporation by an organism of a substance added to a medium as it is or after conversion into a smaller molecule, or metabolic conversion thereof into another substance. According to the present invention, microorganisms capable of utilizing sulfated polysaccharides derived from brown algae include microorganisms capable of producing enzymes that convert sulfated polysaccharides from brown algae into smaller molecules. It is impossible to identify the bacterium belonging to genus *Fucophilus* of the present invention only using conventional bacteriological classification methods. It is necessary to use a molecular genetic classification method in combination with conventional methods. Such a molecular genetic classification method is exemplified by a method of classification based on homologies among nucleotide sequences of 16S ribosomal DNAs (rDNAs; DNAs encoding ribosomal RNAs). Thus, bacteria belonging to genus *Fucophilus* of the present invention include ones bacteriologically classified into genus *Fucophilus*, as well as ones of which the 16S rDNA nucleotide sequence shares homology of about 90% or more with that of the bacterium belonging to genus *Fucophilus* as disclosed herein. The Advanced BLAST search which is available, for example, at the home page of National Center for Biotechnology Information (NCBI) via the Internet can be utilized for homology analyses of 16S rDNA nucleotide sequences.

Although it is not intended to limit the present invention, for example, *Fucophilus fucoidanolyticus* strain SI-1234 of the present invention can be preferably used as a bacterium belonging to genus *Fucophilus*. *Fucophilus fucoidanolyticus* strain SI-1234 is a bacterium newly obtained by the present inventors by screening from a content in a digestive tract of a sea cucumber. Its bacteriological properties are as follows.

a. Morphological Properties:
Coccus of 1.2 to 1.6 μm in diameter
Spore: no
Gram staining: negative b. Physiological Properties:
(1) Growth temperature: 25° C.
(2) Attitude to oxygen: aerobic
(3) Catalase: positive
(4) Oxidase: negative
(5) Salt requirements:
Growth in 0% salt medium: negative
Growth in 1% salt medium: negative
Growth in seawater medium: positive
(6) Quinones: menaquinone 7
(7) GC content of intracellular DNA: 52%
(8) OF-test: not generating acid
(9) Colony color: not generating characteristic colony color
(10) Motility: negative
(11) Gliding: negative
(12) Flagellum: no This strain is classified into Group 4 (Gram-negative aerobic bacilli and cocci) according to the basic classification as described in Bergey's Manual of Determinative Bacteriology, Vol. 9 (1994). However, this strain is different from bacteria belonging to Group 4 in that it has menaquinone 7 in its electron transport chain and the GC content is 52%. Then, a 16S rDNA region was amplified using primers having nucleotide sequences of SEQ ID NOS:1 and 2 as well as TaKaRa PCR Amplification Kit, and the nucleotide sequence of the amplified fragment was analyzed according to a conventional method in order to determine the nucleotide sequence of the 16S rDNA of the strain. The nucleotide sequence of the 16S rDNA is shown as SEQ ID NO:3. Comparison of the nucleotide sequence of SEQ ID NO:3 with those of known bacteria revealed that there was no known bacterium that exhibits homology of about 90% or more over the whole 16S rDNA region (about 1,500 bases). Thus, the present inventors concluded that this strain is a bacterium that does not belong to a known genus but belongs to a new genus, and designated as *Fucophilus fucoidanolyticus* strain SI-1234. *Fucophilus fucoidanolyticus* strain SI-1234 was deposited under Budapest Treaty at International Patent Organism Depositary, National Institute of Advanced Science and Technology (AIST Tsukuba Central 6, 1-1, Higashi 1-Chome, Tsukuba, Ibaraki 305-8566, Japan) on Aug. 18, 1999 (date of original deposit) under accession number FERM BP-7495.

Actually, when *Fucophilus fucoidanolyticus* strain SI-1234 is cultured in a medium containing as a substrate a sulfated polysaccharide selected from those derived from brown algae belonging, for example, without limitation, to order Laminariales (e.g., *Kjellmaniella crassifolia* Miyabe, *Laminaria japonica* Areschoug, *Undaria pinnatifida* (Harvey) Suringar, *Lessonia nigrescens*, *Ecklonia maxima*, order Chordariales (e.g., *Nemacystus decipiens* (Suringar) Kuckuck, *Cladosiphon okamuranus* Tokida) and order Fucales (e.g., *Fucus vesiculosus*, *Ascophyllum nodosum*), the sulfated polysaccharide in the medium is utilized. Furthermore, when such a sulfated polysaccharide is mixed with an extract of the bacterial cells, conversion of the sulfated polysaccharide into smaller molecules is clearly observed.

*Fucophilus fucoidanolyticus* strain SI-1234 of the present invention is a microorganism that is capable of utilizing plural sulfated polysaccharides derived from the above-mentioned brown algae, degrading a sulfated glucuronofucan and producing the fucoidan deacetylase, the α-D-glucuronidase and the endo-α-L-fucosidase of the present invention.

According to the present invention, a sulfated glucuronofucan is a sulfated polysaccharide mainly containing fucose and glucuronic acid as constituting saccharides at a molar ratio of 35:10 to 44:10, and it is known to have an acetyl group. The sulfated glucuronofucan is exemplified by one containing fucose, glucuronic acid and acetyl group at a molar ratio of 4:1:0.5. The average molecular weight is, for example, about 1,000,000 (molecular weight distribution: about 100,000 to 2,000,000) as determined by HPLC gel filtration.

The structure of the sulfated glucuronofucan according to the present invention is represented by general formula (VIII) below. In the general formula, n is an integer of 1 or more. For example, the sulfated glucuronofucans include those in which n is in the range of 1 to 5000, preferably 1 to 1000. The sulfated glucuronofucans include those having a structure in which general formula (VIII) is continuously repeated and those having a structure in which general formula (VIII) is discontinuously included being intervened by other structures as long as they are within the definition as described above.

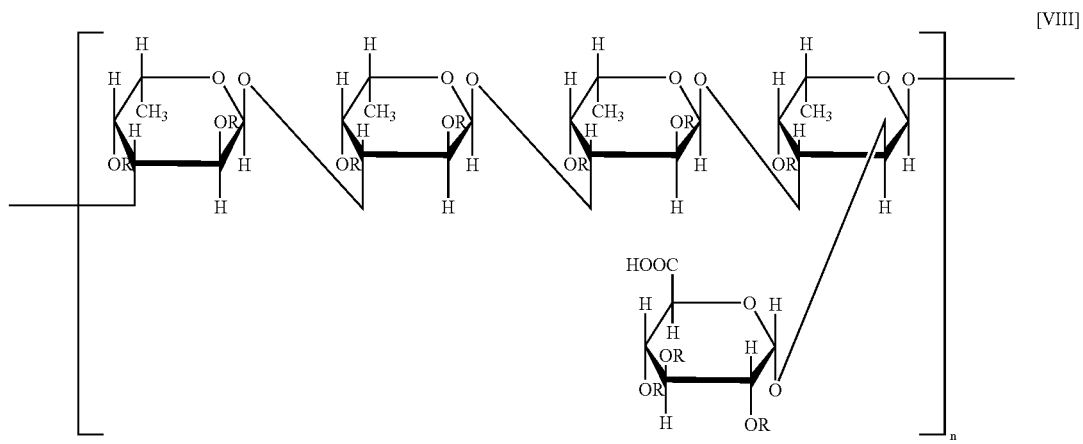

wherein R is H, SO₃H or CH₃CO.

The molecular weight, the saccharide composition and the sulfate group content of the sulfated glucuronofucan vary depending on the harvest time of the raw material for the sulfated glucuronofucan, the method used for drying the raw material, the method used for storing the raw material, the heating or pH conditions used for extracting the sulfated glucuronofucan and the like. For example, the sulfated glucuronofucan may be hydrolyzed with acid. Therefore, the molecular weight, the molecular weight distribution, the saccharide composition and the sulfate group content of the sulfated glucuronofucan disclosed herein are just examples and may be readily changed depending on the conditions used for extracting the sulfated glucuronofucan. For example, a sulfated glucuronofucan having the above-mentioned saccharide composition and molecular weight is obtained from *Cladosiphon okamuranus* Tokida by extraction at pH 6.0 at 95° C. for 2 hours. Thus, a sulfated glucuronofucan having desired molecular weight, molecular weight distribution, saccharide composition or sulfate group content can be prepared using appropriately selected preparation conditions. For example, about two sulfate group residues are contained per four fucose saccharides as the principal constituting saccharides of the sulfated glucuronofucan. Generally, sulfate groups attached to saccharides through ester bonds are chemically labile and readily cleaved with acid, alkali or heat. The sulfate content or the acetyl group content is reduced, for example, by heating under acidic or alkaline conditions. Accordingly, the sulfated glucuronofucan can be intentionally desulfated or deacetylated. The amount of sulfate groups or acetyl groups to be cleaved can be controlled by selecting the type and/or the concentration of the acid or alkali as well as the temperature and/or the time of heating upon the desulfation or the deacetylation. Although it is not intended to limit the present invention, a deacetylated sulfated glucuronofucan obtained, for example, by treatment in a solution of sodium hydroxide at a concentration of about 0.5 to 1 N at 25° C. for 24 hours can be preferably used as a substrate for the α-D-glucuronidase or the endo-α-L-fucosidase of the present invention.

Thus, the sulfated glucuronofucans according to the present invention include all of those derived from brown algae as long as they have the above-mentioned properties or they are converted into smaller molecules using the sulfated glucuronofucan-degrading enzyme of the present invention.

There is no specific limitation concerning the origin of the sulfated glucuronofucan. For example, brown algae belonging to family Chordariaceae such as *Cladosiphon okamuranus* Tokida, *Sphaerotrichia divaricata* (Agardh) Kylin, *Eudesme viescens* (Carmichael) J. Agardh or *Tinocladia crassa* (Suringar) Kylin are preferable as raw materials because their sulfated glucuronofucan contents are high.

For example, the main chain of the sulfated polysaccharide derived from *Cladosiphon okamuranus* Tokida consists of L-fucose which is more labile to acid than general saccharides. Therefore, it is considered that extraction at pH 3.0 or with 0.2 N hydrochloric acid may result in conversion of the sulfated polysaccharide into smaller molecules. That is, the sulfated polysaccharide derived from *Cladosiphon okamuranus* Tokida is readily converted into smaller molecules by heating or treatment with acid like other polysaccharides containing sulfated L-fucose as the principal constituting saccharide.

The sulfated glucuronofucan according to the present invention has a sulfate group and/or a carboxyl group in its molecule. Such groups react with various bases to form salts. Since the sulfated glucuronofucan according to the present invention is stable in a form of salt, it is usually provided in a form of salt with sodium and/or potassium and/or calcium. One can convert the salt into the sulfated glucuronofucan according to the present invention in a free form by utilizing a cation exchange resin such as Dowex 50W. Optionally, the salts may be subjected to conventional salt exchange for other various desirable salts.

Pharmaceutically acceptable salts can be used as the salts of the sulfated glucuronofucan according to the present invention. Examples of the salts include salts with alkaline metals such as sodium and potassium, salts with alkaline earth metals such as calcium, magnesium and zinc as well as ammonium salts.

A water-soluble fraction extract is first obtained from brown algae in order to produce the sulfated glucuronofucan used according to the present invention. In this case, it is preferable to obtain the water-soluble fraction extract at pH 4–9 at a temperature of 100° C. or below in order to prevent the conversion of the sulfated glucuronofucan into smaller molecules. Furthermore, amino acids or small molecule pigments in the extract can be efficiently removed using ultrafiltration. In addition, activated carbon treatment is effective for the removal of hydrophobic substances. As a result, a fraction of sulfated polysaccharides derived from brown algae can be obtained. A more highly pure sulfated glucuronofucan can be obtained by separating the fraction using an anion exchange column.

The sulfated glucuronofucan obtained as described above exhibits an effect on hair growth. Thus, it is useful as a component for a hair growth tonic, for example.

Either the sulfated polysaccharide fraction obtained as described above or the sulfated glucuronofucan purified using an anion exchange column may be used as a substrate for the fucoidan deacetylase, the α-D-glucuronidase or the endo-α-L-fucosidase of the present invention. It may be used as a substrate for determining activities upon purification of the fucoidan deacetylase, the α-D-glucuronidase or the endo-α-L-fucosidase of the present invention. Also, it may be used as a raw material for producing the deacetylated sulfated glucuronofucan, the deacetylated deglucuronylated sulfated glucuronofucan or the sulfated glucuronofucan oligosaccharide of the present invention.

As used herein, a sulfated glucuronofucan oligosaccharide refers to an oligosaccharide generated from a sulfated glucuronofucan. It basically contains a sulfate group, a glucuronyl group, a fucosyl group and an acetyl group. However, an oligosaccharide consisting, for example, only of a sulfate group and a fucosyl group may be referred to as a sulfated glucuronofucan oligosaccharide if it is derived from a sulfated glucuronofucan.

As used herein, a fucoidan deacetylase refers to an enzyme that acts on a sulfated glucuronofucan, a sulfated glucuronofucan oligosaccharide and the like, and hydrolyzes an acetyl group to release acetic acid. The chemical and physical properties of the fucoidan deacetylase of the present invention are as follows:

(I) acting on a sulfated glucuronofucan, a sulfated glucuronofucan oligosaccharide and the like and hydrolyzing an acetyl group to release acetic acid;

(II) having an optimal pH of about 6 to 9.1 (FIG. 1, a graph illustrating the relationship between the reaction pH and the relative activity of the enzyme of the present invention, in which the vertical axis represents the relative activity (%) and the horizontal axis represents the pH);

(III) having an optimal temperature of about 23 to 45° C. (FIG. 2, a graph which illustrates the relationship between the reaction temperature and the relative activity of the enzyme of the present invention, in which the vertical axis represents the relative activity (%) and the horizontal axis represents the temperature (° C.)); and (IV) having a molecular weight of about 30,000 to 50,000 as determined by gel filtration.

The fucoidan deacetylase of the present invention can be identified by measuring an activity of degrading a sulfated glucuronofucan oligosaccharide having an acetyl group and a compound prepared by fluorescently labeling it at the reducing end. A sensitive system for determining the activity for a trace amount can be constructed using such a fluorescently labeled oligosaccharide. A fucoidan deacetylase activity can be determined by allowing a fucoidan deacetylase to act on a sulfated glucuronofucan oligosaccharide, and then separating acetic acid and a deacetylated sulfated glucuronofucan oligosaccharide contained in the reaction product and measuring the contents of acetic acid and acetyl groups, or subjecting the reaction product to mass spectrometric analyses. A cell-free extract from a producer strain or an enzyme solution obtained after purification using various column chromatographies may be used for measuring the activity of the fucoidan deacetylase of the present invention.

In one embodiment, the deacetylase of the present invention is activated in the presence of sodium chloride and/or a protein. Each factor is effective when it is used alone or in combination. Regarding sodium chloride, any material containing sodium chloride such as sodium chloride as a reagent, table salt, seawater or artificial seawater may serve as sodium chloride. The concentration of sodium chloride to be added to a reaction mixture for the deacetylase of the present invention ranges preferably from 0.1 mM to 1 M, more preferably from 1 mM to 600 mM.

Regarding a protein, any protein may be used as a protein to be added to a reaction mixture for activation of the fucoidan deacetylase of the present invention as long as it does not degrade the fucoidan deacetylase of the present invention, or it does not inhibit the reaction. Bovine serum albumin can be preferably used. Also, proteins extracted from cells of *Fucophilus fucoidanolyticus* strain SI-1234 of the present invention may be used, for example. The concentration of the protein to be added to a reaction mixture for the fucoidan deacetylase of the present invention ranges preferably from 0.001 to 10 mg/ml, more preferably from 0.01 to 1 mg/ml.

Figure 3:
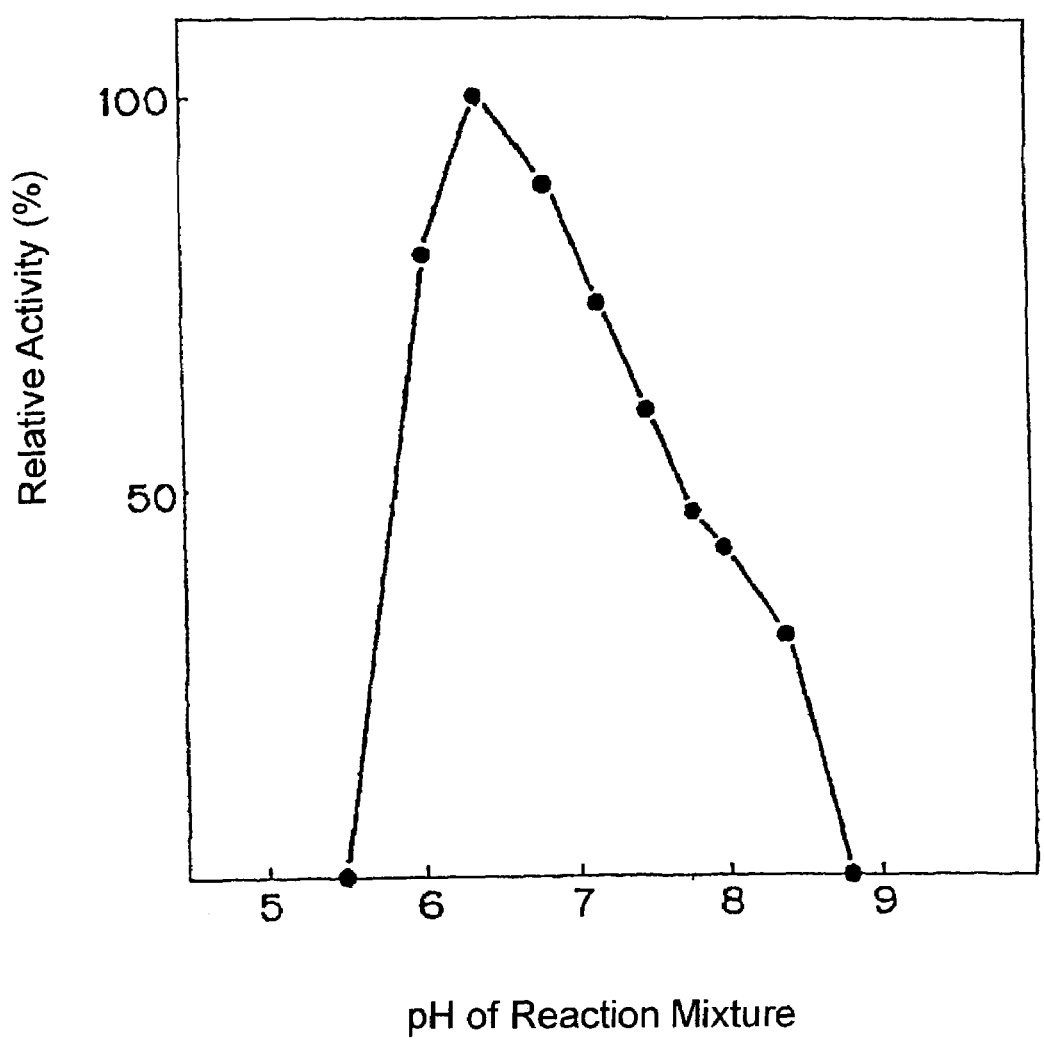
FIG. 3: a graph which illustrates the relationship between pH and the relative activity (%) of the α-D-glucuronidase according to the present invention.
Figure 4:
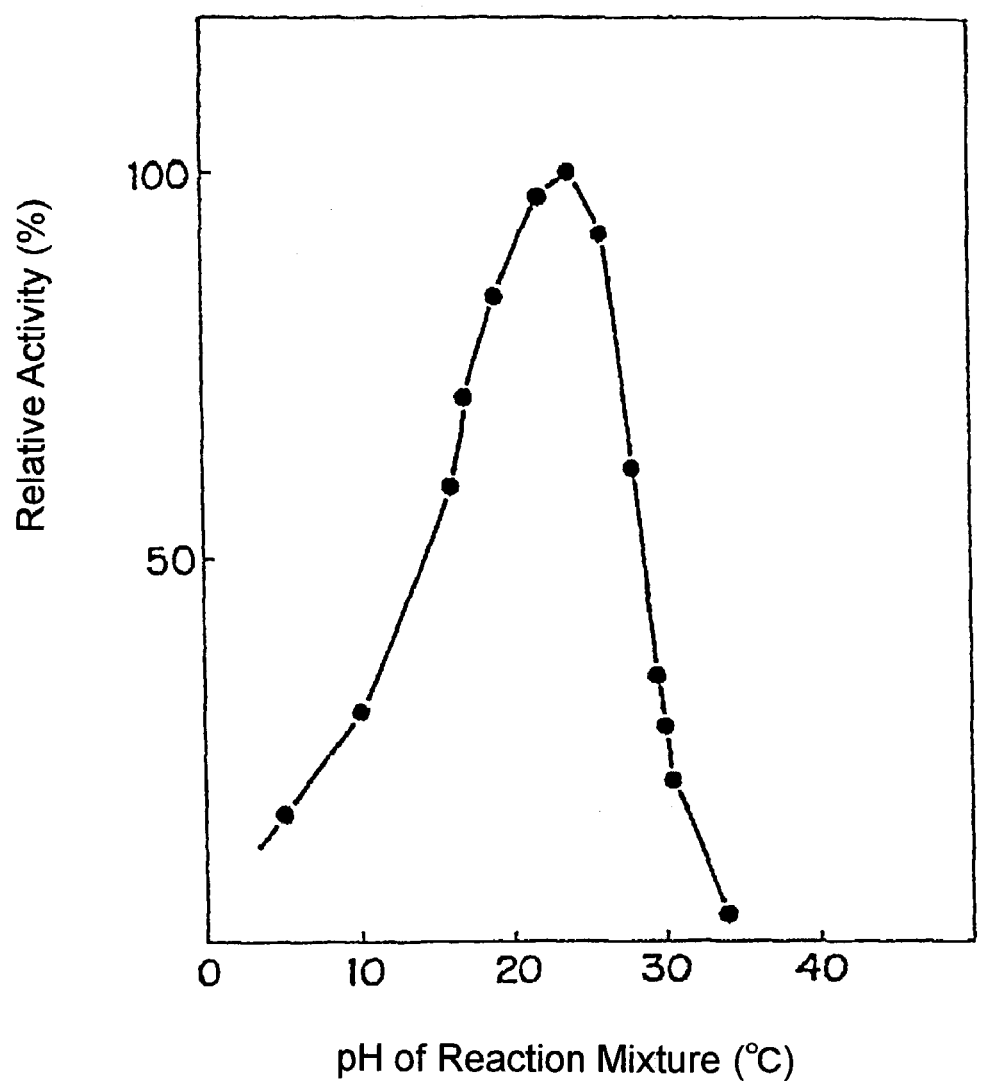
FIG. 4: a graph which illustrates the relationship between temperature (° C.) and the relative activity (%) of the α-D-glucuronidase according to the present invention.

As used herein, an α-D-glucuronidase refers to an enzyme that acts on a deacetylated sulfated glucuronofucan, a sulfated glucuronofucan oligosaccharide and the like and hydrolyzes an α-D-glucuronyl bond between glucuronic acid and fucose to release D-glucuronic acid. The chemical and physical properties of the α-D-glucuronidase of the present invention are as follows:

(I) acting on a deacetylated sulfated glucuronofucan, a sulfated glucuronofucan oligosaccharide and the like and hydrolyzing an α-D-glucuronyl bond to release D-glucuronic acid;

(II) having an optimal pH of about 5.8 to 7.8 (FIG. 3, a graph illustrating the relationship between the reaction pH and the relative activity of the enzyme of the present invention, in which the vertical axis represents the relative activity (%) and the horizontal axis represents the pH);

(III) having an optimal temperature of about 14 to 29° C. (FIG. 4, a graph which illustrates the relationship between the reaction temperature and the relative activity of the enzyme of the present invention, in which the vertical axis represents the relative activity (%) and the horizontal axis represents the temperature (° C.)); and (IV) having a molecular weight of about 120,000 to 180,000 as determined by gel filtration.

The α-D-glucuronidase of the present invention can be identified by measuring an activity of degrading a deacetylated sulfated glucuronofucan. Also, a sulfated glucuronofucan oligosaccharide or a compound prepared by fluorescently labeling it with 2-aminopyridine at the reducing end may serve as a substrate for this enzyme. A sensitive system for determining the activity for a trace amount can be constructed using such a fluorescently labeled oligosaccharide. An α-D-glucuronidase activity can be determined by allowing an α-D-glucuronidase to act on a sulfated glucuronofucan oligosaccharide, and then separating glucuronic acid and a sulfated glucuronofucan oligosaccharide contained in the reaction product and measuring the total sugar content and the total uronic acid content, or subjecting the reaction product to mass spectrometric analyses. A cell-free extract from a producer strain or an enzyme solution obtained after purification using various column chromatographies may be used for measuring the activity of the α-D-glucuronidase of the present invention.

In one embodiment, the α-D-glucuronidase of the present invention is activated in the presence of sodium chloride, a calcium ion and/or a protein. Each factor is effective when it is used alone, or two or three are used in combination.

Regarding sodium chloride, any material containing sodium chloride such as sodium chloride as a reagent, table salt, seawater or artificial seawater may serve as sodium chloride. The concentration of sodium chloride to be added to a reaction mixture for the α-D-glucuronidase of the present invention ranges preferably from 0.1 mM to 1 M, more preferably from 1 mM to 600 mM.

Regarding a calcium ion, any material may be used as long as it generates an calcium ion. Soluble calcium salts such as calcium chloride and calcium acetate can be preferably used. Furthermore, insoluble calcium salts such as calcium carbonate, calcium phosphate, calcium citrate and calcium sulfate slowly generate calcium ions in the presence of a dissolved sulfated polysaccharide (e.g., a sulfated glucuronofucan). Thus, they can be used to activate the α-D-glucuronidase of the present invention. If a calcium salt is contained as a counter ion to a sulfate group or a carboxyl group of a sulfated glucuronofucan, the substrate itself serves as a source for generating a calcium ion. The amount of a calcium ion source to be added for activation can be reduced correspondingly. In some cases, the enzyme may act without adding a calcium salt. The concentration of a calcium ion to be added to a reaction mixture for the α-D-glucuronidase of the present invention ranges preferably from 0.1 to 200 mM, more preferably from 1 to 100 mM.

Regarding a protein, any protein may be used as a protein to be added to a reaction mixture for activation of the α-D-glucuronidase of the present invention as long as it does not degrade the α-D-glucuronidase of the present invention, or it does not inhibit the reaction. Bovine serum albumin can be preferably used. Also, proteins extracted from cells of *Fucophilus fucoidanolyticus* strain SI-1234 of the present invention may be used, for example. The concentration of the protein to be added to a reaction mixture for the α-D-glucuronidase of the present invention ranges preferably from 0.001 to 10 mg/ml, more preferably from 0.01 to 1 mg/ml.

As used herein, an endo-α-L-fucosidase refers to an enzyme that acts on a deacetylated deglucuronylated sulfated glucuronofucan, a sulfated glucuronofucan oligosaccharide and the like and hydrolyzes an α-L-fucosyl bond in an endo-type manner to generate an oligosaccharide having L-fucose at its reducing end. The endo-α-L-fucosidase of the present invention does not act on a naturally occurring sulfated glucuronofucan so much. However, it acts well on a sulfated glucuronofucan after treatment with a fucoidan deacetylase and an α-D-glucuronidase or in the presence of a fucoidan deacetylase and an α-D-glucuronidase. If the acetyl group and the glucuronic acid are removed for some reason (due to an enzyme derived from another marine bacterium, a physicochemical factor, etc.), a naturally occurring sulfated glucuronofucan may be preferably used as a substrate for the endo-α-L-fucosidase of the present invention.

Figure 5:
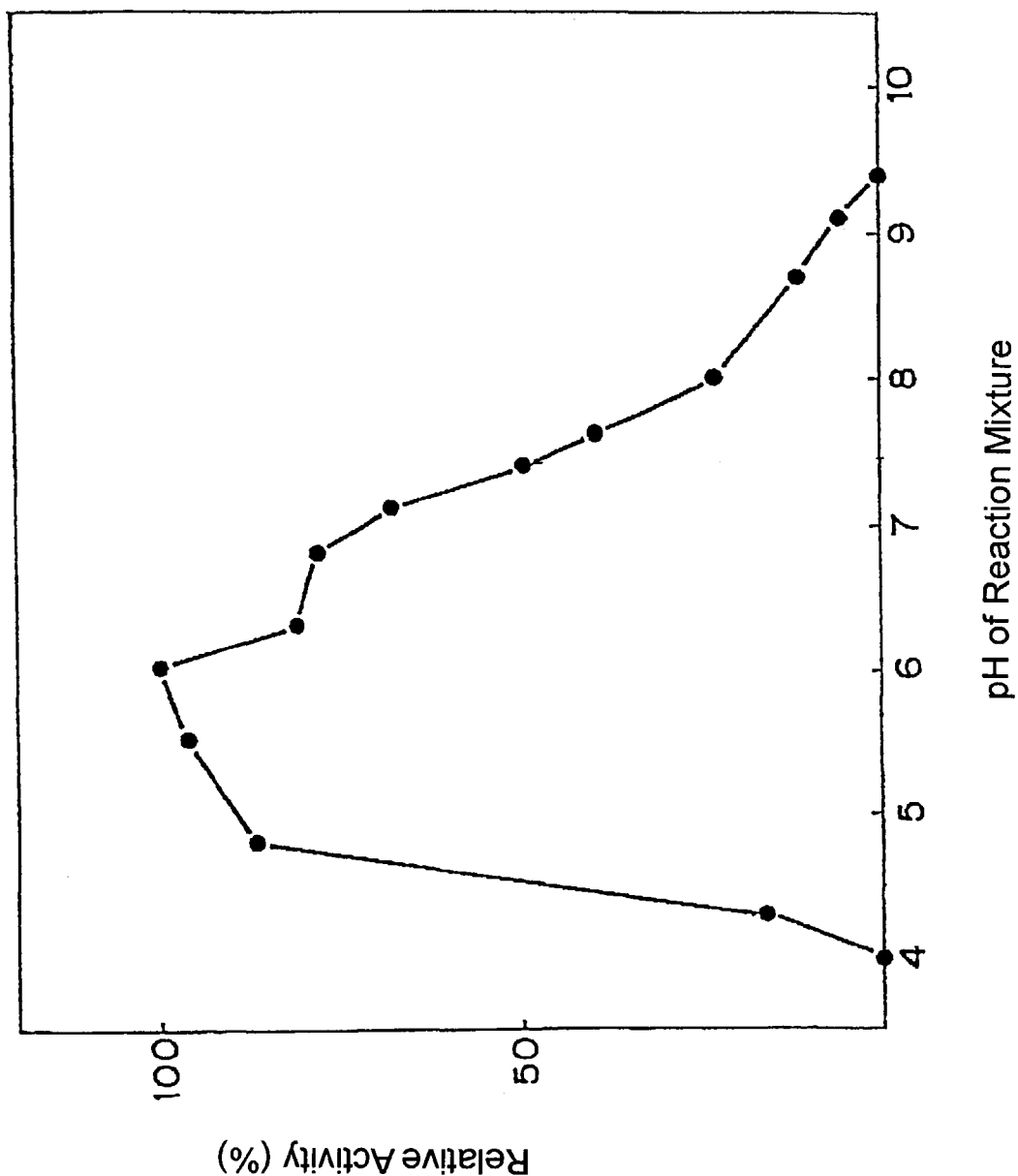
FIG. 5: a graph which illustrates the relationship between pH and the relative activity (%) of the endo-α-L-fucosidase according to the present invention.
Figure 6:
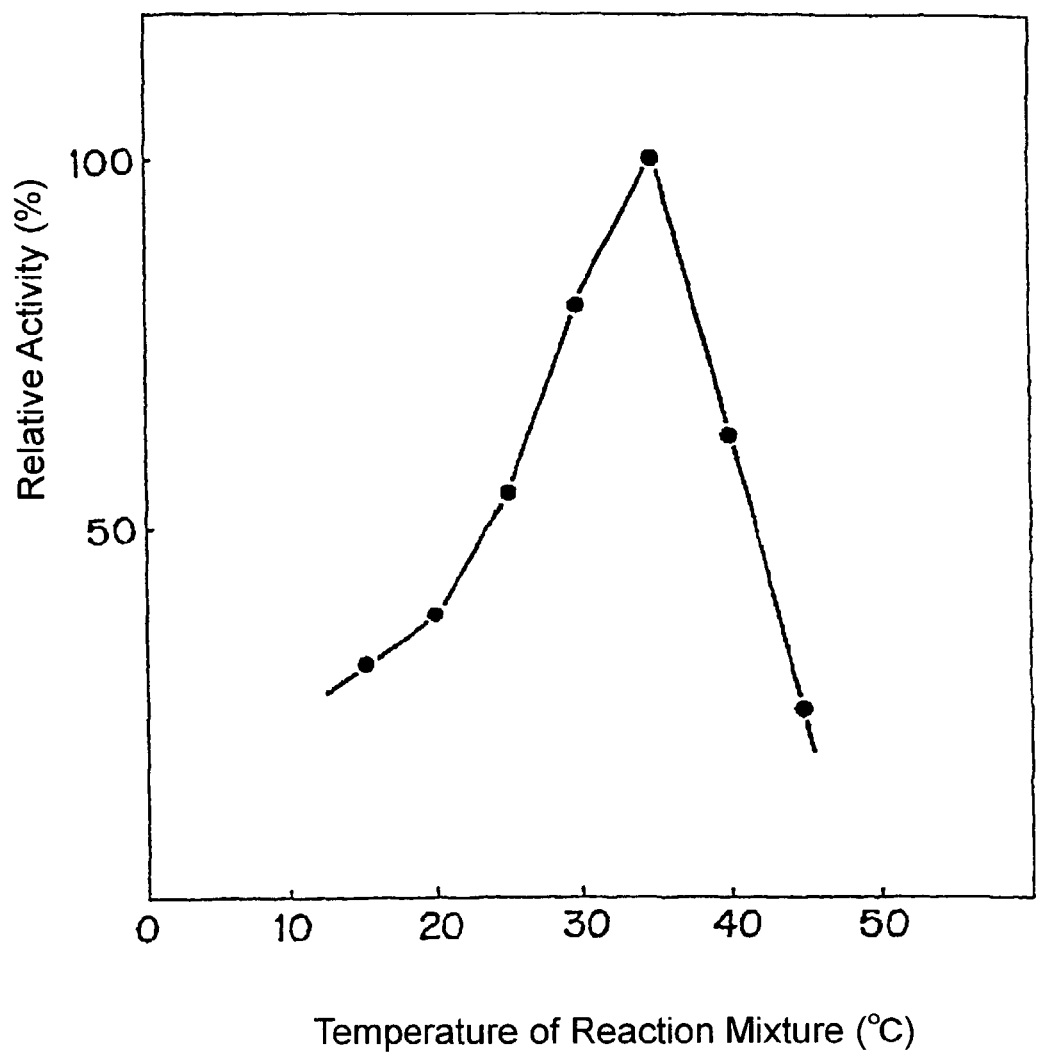
FIG. 6: a graph which illustrates the relationship between temperature (° C.) and the relative activity (%) of the endo-α-L-fucosidase according to the present invention.

The chemical and physical properties of the endo-α-L-fucosidase of the present invention are as follows:

(I) acting on a deacetylated deglucuronylated sulfated glucuronofucan, a sulfated glucuronofucan oligosaccharide and the like and hydrolyzing an α-L-fucosyl bond in an endo-type manner to generate an oligosaccharide having L-fucose at its reducing end;

(II) having an optimal pH of about 4.5 to 7.4 (FIG. 5, a graph illustrating the relationship between the reaction pH and the relative activity of the enzyme of the present invention, in which the vertical axis represents the relative activity (%) and the horizontal axis represents the pH);

(III) having an optimal temperature of about 23 to 42° C. (FIG. 6, a graph which illustrates the relationship between the reaction temperature and the relative activity of the enzyme of the present invention, in which the vertical axis represents the relative activity (%) and the horizontal axis represents the temperature (° C.)); and (IV) having a molecular weight of about 150,000 to 200,000 as determined by gel filtration.

The endo-α-L-fucosidase of the present invention can be identified by measuring an activity of degrading a deacetylated deglucuronylated sulfated glucuronofucan. Also, an oligosaccharide obtained by treating a sulfated glucuronofucan oligosaccharide with the α-D-glucuronidase of the present invention or a compound prepared by fluorescently labeling it with 2-aminopyridine at the reducing end may serve as a substrate for this enzyme. A sensitive system for determining the activity for a trace amount can be constructed using such a fluorescently labeled oligosaccharide. For example, an endo-α-L-fucosidase activity can be determined by carrying out a reaction using 8Fuc-4S-PA (infra) as a substrate, and then analyzing the reaction product using HPLC. A cell-free extract from a producer strain or an enzyme solution obtained after purification using various column chromatographies may be used for measuring the activity of the endo-α-L-fucosidase of the present invention.

In one embodiment, the endo-α-L-fucosidase of the present invention is activated in the presence of sodium chloride, a calcium ion and/or a protein. Each factor is effective in activation when it is used alone, or two or three are used in combination. Regarding sodium chloride, any material containing sodium chloride such as sodium chloride as a reagent, table salt, seawater or artificial seawater may serve as sodium chloride. The concentration of sodium chloride to be added to a reaction mixture for the endo-α-L-fucosidase of the present invention ranges preferably from 0.1 mM to 1 M, more preferably from 1 mM to 600 mM.

Regarding a calcium ion, any material may be used as long as it generates an calcium ion. Soluble calcium salts such as calcium chloride and calcium acetate can be preferably used. Furthermore, insoluble calcium salts such as calcium carbonate, calcium phosphate, calcium citrate and calcium sulfate slowly generate calcium ions in the presence of a dissolved sulfated polysaccharide (e.g., a sulfated glucuronofucan). Thus, they can be used to activate the endo-α-L-fucosidase of the present invention. If a calcium salt is contained as a counter ion to a sulfate group or a carboxyl group of a sulfated glucuronofucan, the substrate itself serves as a source for generating a calcium ion. The amount of a calcium ion source to be added for activation can be reduced correspondingly. In some cases, the enzyme may act without adding a calcium salt. The concentration of a calcium ion to be added to a reaction mixture for the endo-α-L-fucosidase of the present invention ranges preferably from 0.1 to 200 mM, more preferably from 1 to 100 mM.

Regarding a protein, any protein may be used as a protein to be added to a reaction mixture for activation of the endo-α-L-fucosidase of the present invention as long as it does not degrade the endo-α-L-fucosidase of the present invention, or it does not inhibit the reaction. Bovine serum albumin can be preferably used, for example. Also, proteins extracted from cells of *Fucophilus fucoidanolyticus* strain SI-1234 of the present invention may be used, for example. The concentration of the protein to be added to a reaction mixture for the endo-α-L-fucosidase of the present invention ranges preferably from 0.001 to 10 mg/ml, more preferably from 0.01 to 1 mg/ml.

There is no specific limitation concerning the microorganism used for the production of the fucoidan deacetylase, the α-D-glucuronidase or the endo-α-L-fucosidase of the present invention as long as it produces an enzyme (or enzymes) that convert(s) a sulfated polysaccharide fraction as described above or a sulfated glucuronofucan into smaller molecules. For example, a bacterium belonging to genus *Fucophilus* can be preferably used. The bacteria belonging to genus *Fucophilus* include ones bacteriologically classified into genus *Fucophilus*, as well as ones classified into genus *Fucophilus* based on the 16S rDNA nucleotide sequence homology. The bacteria belonging to genus *Fucophilus* include all microorganisms producing an enzyme that degrades a sulfated glucuronofucan as the fucoidan deacetylase, the α-D-glucuronidase or the endo-α-L-fucosidase of the present invention does.

Any nutrient source can be added to a medium for culturing a microorganism producing the fucoidan deacetylase, the α-D-glucuronidase and the endo-α-L-fucosidase of the present invention as long as it is utilized by the microorganism to produce the enzymes in the presence of the nutrient source. For example, a sulfated glucuronofucan, algae such as *Cladosiphon okamuranus* Tokida, alginic acid, laminaran, fucose, glucose, mannitol, glycerol, saccharose, maltose, starch and the like can be utilized as carbon sources. Yeast extract, peptone, casamino acid, corn steep liquor, meat extract, defatted soybean, ammonium sulfate, ammonium chloride, urea, uric acid and the like are suitable nitrogen sources. In addition, a chloride, a phosphate or a sulfate of sodium, potassium, magnesium, calcium, zinc or the like may be added. Furthermore, the medium for the microorganism may be made from seawater or commercially available artificial seawater.

Naturally, the culture conditions, the composition of the medium and the like are determined such that the productivities of the fucoidan deacetylase, the α-D-glucuronidase and the endo-α-L-fucosidase of the present invention become maximal depending on the microorganism used. For example, culturing with aeration and stirring at a culture temperature of 15 to 30° C. at medium pH of 5 to 9 for 5 to 72 hours is preferable. The maximal productivities of the fucoidan deacetylase, the α-D-glucuronidase and the endo-α-L-fucosidase of the present invention are achieved by culturing under the above-mentioned conditions. The fucoidan deacetylase, the α-D-glucuronidase and the endo-α-L-fucosidase of the present invention can be obtained from cells and a culture supernatant separated each other by centrifugation after culturing.

Although it is not intended to limit the present invention, a cell-free extract is obtained, for example, by culturing *Fucophilus fucoidanolyticus* strain SI-1234 of the present invention in an appropriate medium, collecting the cells, and disrupting the cells by a conventional means for cell disruption such as sonication. A purified enzyme preparation can be then obtained from the extract by a conventional means for purification. The fucoidan deacetylase, the α-D-glucuronidase or the endo-α-L-fucosidase of the present invention in a purified form substantially free from another sulfated fucose-containing polysaccharide-digesting enzyme can be obtained by purification using, for example, salting out, ion exchange column chromatography, hydrophobic column chromatography, gel filtration or the like. Furthermore, the α-D-glucuronidase and the endo-α-L-fucosidase of the present invention can be readily separated by using a resin to which a sulfated glucuronofucan is immobilized.

Furthermore, a purification procedure similar to that for the purification of the intracellular enzyme can be used to purify the fucoidan deacetylase, the α-D-glucuronidase or the endo-α-L-fucosidase of the present invention from the culture supernatant which also contains the enzyme in large quantities.

*Fucophilus fucoidanolyticus* strain SI-1234 is a microorganism that utilizes a sulfated glucuronofucan, and produces the fucoidan deacetylase, the α-D-glucuronidase and the endo-α-L-fucosidase of the present invention inside or outside the cell to degrade the sulfated glucuronofucan. These three enzymes can be separated by column purification procedures.

The endo-α-L-fucosidase of the present invention degrades a sulfated glucuronofucan to sulfated glucuronofucan oligosaccharides in the presence of the fucoidan deacetylase and the α-D-glucuronidase of the present invention. It is almost unable to degrade the sulfated glucuronofucan when used alone. The endo-α-L-fucosidase of the present invention by itself can degrade the deacetylated deglucuronylated sulfated glucuronofucan of the present invention. Thus, one can understand that the presence of the fucoidan deacetylase and the α-D-glucuronidase of the present invention is not necessarily required for the degradation of a sulfated glucuronofucan to sulfated glucuronofucan oligosaccharides, rather deacetylation and deglucuronylation of the sulfated glucuronofucan are required.

The deacetylated deglucuronylated sulfated glucuronofucan according to the present invention is one obtained by allowing the α-D-glucuronidase of the present invention to act on a deacetylated sulfated glucuronofucan, and hydrolyzing at least one α-D-glucuronyl bond molecule. Removal of D-glucuronic acid from the deacetylated sulfated glucuronofucan finally results in loss of the glucuronic acid content (i.e., a deacetylated deglucuronylated sulfated fucan). A deacetylated deglucuronylated sulfated glucuronofucan with a varying glucuronic acid content containing fucose and glucuronic acid at a molar ratio of 4:1 to 4:0 can be produced by adjusting the enzymatic reaction conditions.

The deacetylated deglucuronylated sulfated glucuronofucan of the present invention may be obtained by allowing an α-D-glucuronidase to act on a deacetylated sulfated glucuronofucan and removing a released D-glucuronic acid, for example, by ultrafiltration, gel filtration, anion exchange column treatment or the like. Optionally, desalting, lyophilization or the like may be carried out. The deglucuronylation can be efficiently carried out by deacetylating the sulfated glucuronofucan beforehand by treatment with a fucoidan deacetylase, alkali treatment or the like.

For example, about one D-glucuronic acid molecule is contained per four fucose molecules in an deacetylated sulfated glucuronofucan obtained by deacetylating a sulfated glucuronofucan derived from *Cladosiphon okamuranus* Tokida. A deacetylated deglucuronylated sulfated glucuronofucan with a varying glucuronic acid content can be prepared by removing D-glucuronic acid using an α-D-glucuronidase. A deacetylated deglucuronylated sulfated glucuronofucan with a varying glucuronic acid content containing fucose and glucuronic acid at a molar ratio of 4:1 to 4:0 can be produced by adjusting the conditions including the amounts of the enzyme and the substrate used for the deglucuronylation reaction, the reaction time, the reaction temperature and pH. Although it is not intended to limit the present invention, for example, appropriate amounts of sodium chloride and bovine serum albumin as well as 500 mU of the α-D-glucuronidase of the present invention are mixed with 1 g of a deacetylated sulfated glucuronofucan and the mixture is reacted at 20° C. at about pH 7 for a varying time.

The deacetylated deglucuronylated sulfated glucuronofucan can be used as a reagent for glycotechnology as it is. It can be used as a substrate for the endo-α-L-fucosidase of the present invention for measuring the activity. The reaction product, i.e., the sulfated glucuronofucan oligosaccharide of the present invention, is useful as a reagent for glycotechnology.

Upon preparation of the deacetylated deglucuronylated sulfated glucuronofucan of the present invention, an deacetylated sulfated glucuronofucan or a material containing a deacetylated sulfated glucuronofucan may be dissolved according to a conventional method. The deacetylated sulfated glucuronofucan or the material containing a deacetylated sulfated glucuronofucan may be dissolved in the solution at the maximal concentration. However, the concentration is usually selected taking its operationality and the titer of the enzyme into consideration. The solvent for the deacetylated sulfated glucuronofucan may be selected from water, buffers and the like depending on the objects. Usually, the pH of the solution is nearly neutral. The enzymatic reaction is usually carried out at about 20° C. The degree of deglucuronylation can be controlled by adjusting the amount of the enzyme, the composition of the reaction mixture, the reaction time and the like. Optionally, the deacetylated deglucuronylated sulfated glucuronofucan may be further subjected to a purification procedure using ion exchange resin treatment, ultrafiltration or the like, or they may be desalted, sterilized or lyophilized.

The deacetylated deglucuronylated sulfated glucuronofucan of the present invention has a sulfate group and/or a carboxyl group in its molecule. Such groups react with various bases to form salts. Since the deacetylated deglucuronylated sulfated glucuronofucan of the present invention is stable in a form of salt, it is usually provided in a form of salt with sodium and/or potassium and/or calcium. One can convert the salt into the deacetylated deglucuronylated sulfated glucuronofucan of the present invention in a free form by utilizing a cation exchange resin such as Dowex 50W. Optionally, the salts may be subjected to conventional salt exchange for other various desirable salt.

Pharmaceutically acceptable salts can be used as the salts of the deacetylated deglucuronylated sulfated glucuronofucan of the present invention. Examples of the salts include salts with alkaline metals such as sodium and potassium, salts with alkaline earth metals such as calcium, magnesium and zinc as well as ammonium salts.

As used herein, a sulfated glucuronofucan oligosaccharide refers to an oligosaccharide having L-fucose at its reducing end that is obtained by deacetylating a sulfated glucuronofucan by the action of the fucoidan deacetylase of the present invention or by alkali treatment, and then allowing an α-D-glucuronidase and an endo-α-L-fucosidase to act on the deacetylated sulfated glucuronofucan. Although it is not intended to limit the present invention, sulfated glucuronofucan oligosaccharides are exemplified by a saccharide having a chemical structure of one selected from the group consisting of general formulas (I) to (III):

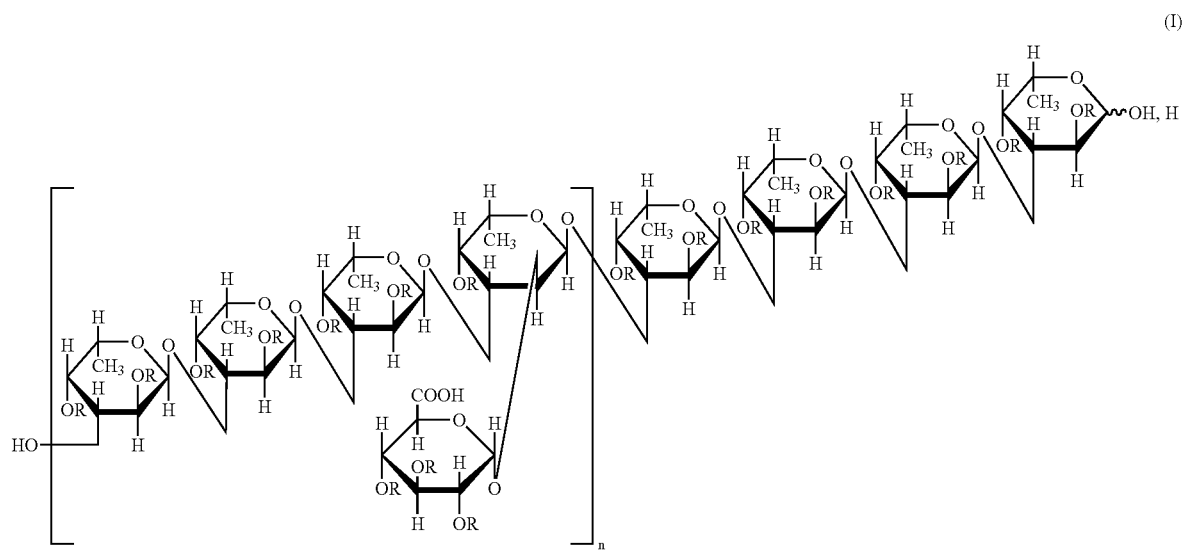

(I)

wherein R is H, SO$_3$H or CH$_3$CO.

-continued

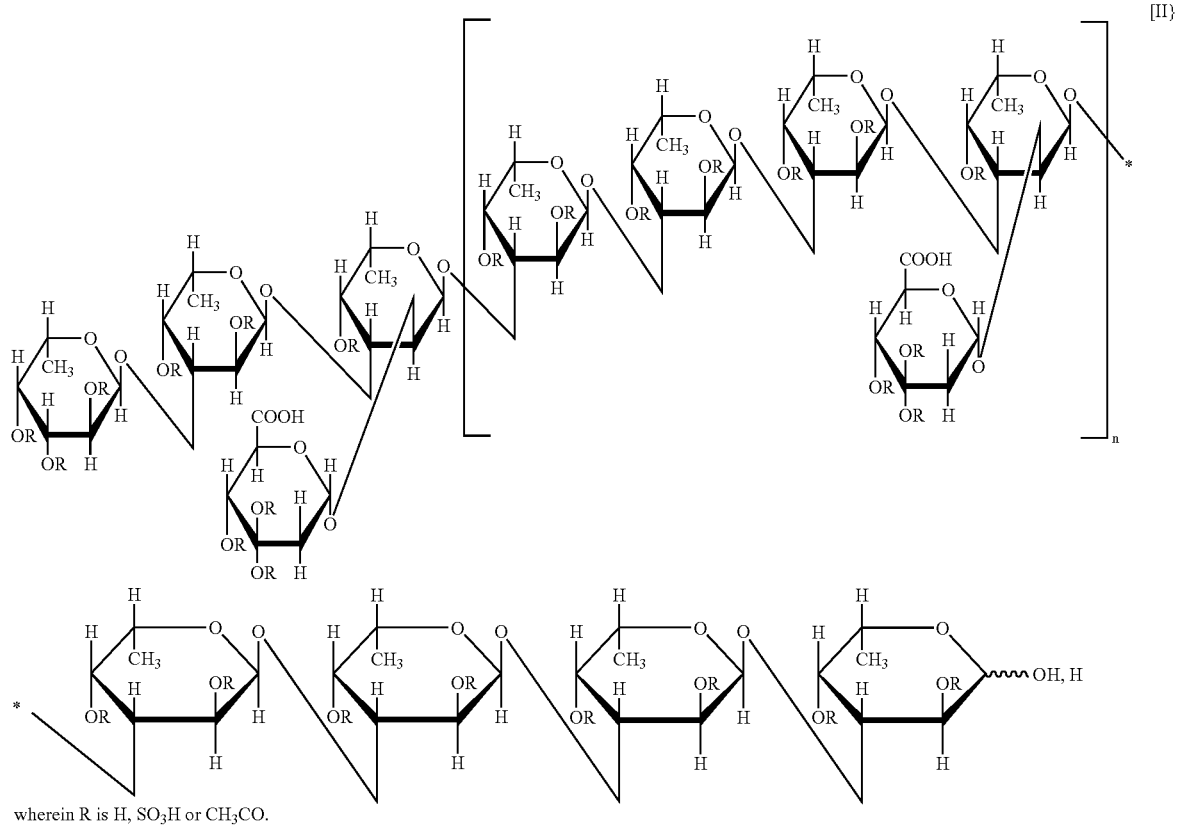

wherein R is H, SO₃H or CH₃CO.

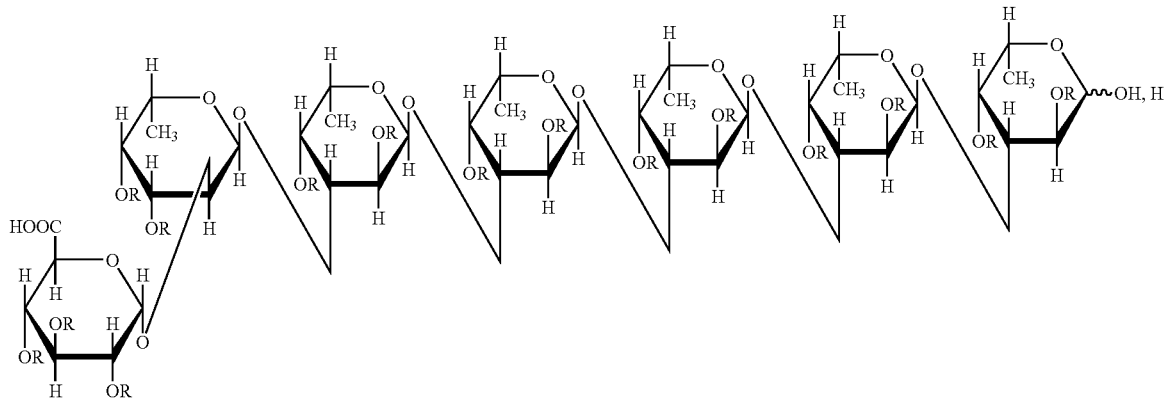

wherein R is H, $SO_3H$ or $CH_3CO$; n is 0 or an integer of 1 or more.

The sulfated glucuronofucan oligosaccharide of the present invention can be efficiently prepared by allowing the fucoidan deacetylase, the α-D-glucuronidase and the endo-α-L-fucosidase of the present invention to act on a sulfated glucuronofucan or a material containing a sulfated glucuronofucan. It may also be prepared by allowing the α-D-glucuronidase and the endo-α-L-fucosidase of the present invention to act on a sulfated glucuronofucan that has been deacetylated by chemical treatment such as alkali treatment beforehand. For example, a partially purified preparation of sulfated glucuronofucan, a sulfated fucose-containing polysaccharide fraction derived from brown algae, a product obtained by extracting brown algae with an aqueous solvent, or brown algae themselves can be preferably used as the material containing a sulfated glucuronofucan. Of course, the sulfated glucuronofucan oligosaccharide of the present invention can also be obtained by allowing the endo-α-L-fucosidase of the present invention to act on the deacetylated deglucuronylated sulfated glucuronofucan of the present invention. Although it is not intended to limit the present invention, for example, a saccharide having a chemical structure of one selected from the group consisting of general formulas (I) to (III) or a salt thereof can be obtained by deacetylating a sulfated glucuronofucan derived from *Cladosiphon okamuranus* Tokida, and allowing the α-D-glucuronidase and the endo-α-L-fucosidase of the present invention to act on the deacetylated sulfated glucuronofucan.

Upon preparation of the sulfated glucuronofucan oligosaccharide of the present invention, a sulfated glucuronofucan or a material containing a sulfated glucuronofucan may be dissolved according to a conventional method. The sulfated glucuronofucan according to the present invention or the material containing a sulfated glucuronofucan may be dissolved in the solution at the maximal concentration. However, the concentration is usually selected taking its operationality and the amounts of the fucoidan deacetylase, the α-D-glucuronidase and the endo-α-L-fucosidase of the present invention used in the reaction into consideration. The solvent for the sulfated glucuronofucan may be selected from water, buffers and the like depending on the objects. Usually, the pH of the solution is nearly neutral. The enzymatic reaction is usually carried out at about 25° C. The molecular weight of the sulfated glucuronofucan oligosaccharide or the contents of glucuronic acid and acetyl groups can be controlled by adjusting the ratio or the amounts of the fucoidan deacetylase, the α-D-glucuronidase and the endo-α-L-fucosidase of the present invention used for the reaction, the composition of the reaction mixture, the reaction time and the like. A sulfated glucuronofucan is degraded using three enzymes, i.e., the fucoidan deacetylase, the α-D-glucuronidase and the endo-α-L-fucosidase of the present invention. The reactions with these three enzymes may be conducted simultaneously or independently. Specifically, the molecular weight distribution and the contents of glucuronic acid and acetyl groups of the sulfated glucuronofucan oligosaccharide of the present invention generated by the following procedure can be readily controlled. First, a sulfated glucuronofucan is deacetylated and deglucuronylated using the fucoidan deacetylase and the α-D-glucuronidase of the present invention. The fucoidan deacetylase and the α-D-glucuronidase of the present invention are then inactivated by heating, or treatment with acid or alkali. Finally, the endo-α-L-fucosidase of the present invention is allowed to act thereon.

The sulfated glucuronofucan oligosaccharide of the present invention having more homogeneous molecular weight or more homogeneous charge density distribution can be prepared by fractionating the sulfated glucuronofucan oligosaccharide of the present invention obtained as described above using molecular weight fractionation or anion exchange column. A conventional means for molecular weight fractionation such as gel filtration or molecular weight fractionation membrane may be used. Optionally, the smaller molecules may be subjected to further purification procedure using ion exchange resin treatment, activated carbon treatment or the like, or they may be desalted, sterilized or lyophilized. Consequently, the sulfated glucuronofucan oligosaccharide of the present invention having a structure so homogeneous as one can determine the structure by NMR analysis can be obtained.

The sulfated glucuronofucan oligosaccharide of the present invention has a sulfate group and a carboxyl group in its molecule. Such groups react with various bases to form salts. Since the sulfated glucuronofucan oligosaccharide of the present invention is stable in a form of salt, it is usually provided in a form of salt with sodium and/or potassium and/or calcium. One can convert the salt into the sulfated glucuronofucan oligosaccharide of the present invention in a free form by utilizing a cation exchange resin such as Dowex 50W. Optionally, the salts may be subjected to conventional salt exchange for other various desirable salts.

Pharmaceutically acceptable salts can be used as the salts of the sulfated glucuronofucan oligosaccharide of the present invention. Examples of the salts include salts with alkaline metals such as sodium and potassium, salts with alkaline earth metals such as calcium, magnesium and zinc as well as ammonium salts.

Additionally, the sulfated glucuronofucan oligosaccharide of the present invention can be used as a reagent for glycotechnology. For example, a 2-aminopyridine (PA)-labeled oligosaccharide prepared by subjecting the oligosaccharide to PA-labeling according to the method as described in JP-B 5-65108 can be used as a substrate for the measurement of an activity of the fucoidan deacetylase, the α-D-glucuronidase or the endo-α-L-fucosidase of the present invention. Thus, the sulfated glucuronofucan oligosaccharide of the present invention is a substance very useful as a reagent for glycotechnology The fucoidan deacetylase, the α-D-glucuronidase and the endo-α-L-fucosidase of the present invention convert a sulfated glucuronofucan into smaller molecules. So, they can be used for the structural analysis of the sulfated glucuronofucan. Furthermore, the stabilities and the reaction rates of the fucoidan deacetylase, the α-D-glucuronidase and the endo-α-L-fucosidase of the present invention are increased in the presence of sodium chloride, a protein and/or a calcium ion in the reaction mixture. Thus, the conversion into smaller molecules can be efficiently conducted in the presence of such a factor for activating a sulfated glucuronofucan-degrading enzyme. In addition, the sulfated glucuronofucan oligosaccharide, the deacetylated sulfated glucuronofucan and the deacetylated deglucuronylated sulfated glucuronofucan of the present invention can be used as reagents for glycotechnology and as substrates for the measurement of activities of the fucoidan deacetylase, the α-D-glucuronidase and the endo-α-L-fucosidase of the present invention.

EXAMPLES

The following examples further illustrate the present invention in detail but are not to be construed to limit the scope thereof.

Referential Example 1

(1) Preparation of Crude Sulfated Glucuronofucan Fraction 625 g of commercially available salted *Cladosiphon okamuranus* Tokida suspended in 4375 ml of 30 mM sodium phosphate buffer (pH 6.0) was processed using a homogenizer at 8,000 rpm for 5 minutes and treated at 95° C. for 1 hour. 10 g of activated carbon was added to a supernatant obtained by centrifugation, and the mixture was then stirred for 30 minutes. A supernatant obtained by centrifugation was concentrated to 2 l using an ultrafiltration device equipped with hollow fibers with exclusion molecular weight of 100,000. The concentrate was subjected to solvent exchange for 20 mM sodium chloride and lyophilized to obtain 10.9 g of a dried preparation of a crude sulfated glucuronofucan fraction.

(2) Method for Measuring Activity of Degrading Sulfated Glucuronofucan

The fucoidan deacetylase, the α-D-glucuronidase or the endo-α-L-fucosidase of the present invention cannot act on a sulfated glucuronofucan to efficiently produce oligosaccharides if it is used alone. However, if the above-mentioned three enzymes are used in combination, they can degrade a sulfated glucuronofucan to efficiently convert it into smaller molecules. An activity of degrading a sulfated glucuronofucan in the presence of the three enzymes was designated as "an activity of degrading a sulfated glucuronofucan" and was numerically expressed according to the method for measuring the activity as described below.

Briefly, 10 μl of 1% solution of the crude sulfated glucuronofucan fraction, 52.5 μl of 50 mM imidazole-hydrochloride buffer (pH 6.6), 5.5 μl of 4 M sodium chloride, 2 μl of 1 M calcium chloride, 10 μl of 5 mg/ml bovine serum albumin and 20 μl of an enzyme solution containing the fucoidan deacetylase, the α-D-glucuronidase and the endo-α-L-fucosidase of the present invention were mixed together. After reacting at 30° C. for 3 hours, the reaction mixture was treated at 100° C. for 10 minutes. After centrifugation, 90 μl of the supernatant was analyzed using HPLC to determine the degree of conversion into smaller molecules. As controls, a reaction mixture obtained by a reaction which the buffer used for dissolving the fucoidan deacetylase, the α-D-glucuronidase and the endo-α-L-fucosidase of the present invention was used in place of the enzyme solution and a reaction mixture obtained by a reaction in which water was used in place of the crude sulfated glucuronofucan fraction were similarly analyzed using HPLC. One unit of the activity of degrading a sulfated glucuronofucan is defined as an amount of an enzyme that cleaves fucosyl bonds in 1 μmol of a sulfated glucuronofucan in 1 minute in the above-mentioned reaction system. The amount of cleaved fucosyl bond was calculated according to the following equation:

$$\{(10\times1000\times1/100)MG\}\times\{(MG/M)-1\}\times\{1/(180\times0.02)\}=U/ml \quad \text{Equation 1}$$

10×1000×1/100: the crude sulfated glucuronofucan fraction added to the reaction system (μg);
MG: the average molecular weight of the sulfated glucuronofucan as a substrate;
M: the average molecular weight of the reaction product;
(MG/M)−1: the number of sites cleaved by the enzyme in one sulfated glucuronofucan molecule;
180: the reaction time (minutes); and
0.02: the volume of the enzyme solution (ml).

The HPLC was carried out as follows.

Instrument: L-6200 (Hitachi);
Column: OHpak SB-806HQ (8×300 mm; Showa Denko);
Eluent: 50 mM sodium chloride containing 5 mM sodium azide;
Detection: differential refractive index detector (Shodex RI-71, Showa Denko);
Flow rate: 1 ml/minute; and
Column temperature: 25° C.

The following procedure was carried out in order to determine the average molecular weight of the reaction product. Commercially available pullulan (STANDARD P-82, Showa Denko) of which the molecular weight was known was analyzed under the same conditions as those for the above-mentioned HPLC analysis. The relationship between the molecular weight of pullulan and retention time was expressed as a curve, which was used as a standard curve for determining the molecular weight of the reaction product. The amount of protein was determined by measuring the absorbance of the enzyme solution at 280 nm. The calculation was carried out assuming the absorbance of a solution containing a protein at a concentration of 1 mg/ml as 1.0.

Example 1

*Fucophilus fucoidanolyticus* strain SI-1234 was inoculated into 50 ml of a medium consisting of artificial seawater (pH 8.0) (Jamarine Laboratory) containing the crude sulfated glucuronofucan fraction prepared from *Cladosiphon okamuranus* Tokida as described in Referential Example 1(1) and peptone at concentrations of 0.2% and 1%, respectively, which had been autoclaved at 120° C. for 20 minutes, and cultured at 24° C. for 72 hours to prepare a seed culture. Seven 2-l Erlenmeyer flasks each containing 600 ml of a medium consisting of artificial seawater (pH 8.0) (Jamarine Laboratory) containing the crude sulfated glucuronofucan fraction prepared from *Cladosiphon okamuranus* Tokida as described in Referential Example 1(1) and peptone at concentrations of 0.2% and 1%, respectively, as well as an antifoaming agent (KM70, Shin-Etsu Chemical) were autoclaved at 115° C. for 10 minutes. 5 ml of the seed culture was inoculated into each of the Erlenmeyer flasks and cultured at 90 rpm at 24° C. for 72 hours. After cultivation, the culture was centrifuged to separate cells from a supernatant.

The cells were suspended in 250 ml of 10 mM imidazole-hydrochloride buffer (pH 7.0) containing 100 mM sodium chloride and 10 mM calcium chloride, sonicated and centrifuged to obtain a supernatant. The supernatant was adequately dialyzed against the same buffer and centrifuged to obtain a supernatant as a crude enzyme solution.

The resulting crude enzyme solution was loaded onto a 300-ml DEAE-Cellulofine A-800 column equilibrated with the same buffer. After washing with the same buffer, elution was then carried out with a gradient of 100 mM to 400 mM sodium chloride to collect an active fraction. Thus, a partially purified enzyme solution was obtained. Both the culture supernatant and the crude enzyme solution were confirmed to contain "activities of degrading a sulfated glucuronofucan." The activity detected in the cell extract was 0.4 mU/ml culture medium.

Example 2

(1) The sulfated glucuronofucan oligosaccharides according to the present invention were prepared by allowing the crude enzyme solution as described in Example 1 to act on the crude sulfated glucuronofucan fraction as described in Referential Example 1(1). Briefly, 5 g of the crude sulfated glucuronofucan fraction was dissolved in 1 l of 10 mM imidazole-hydrochloride buffer (pH 6.6) containing 250 mM sodium chloride and 20 mM calcium chloride. 35 mU of the crude enzyme solution as described in Example 1 was then added thereto. The mixture was reacted at 30° C. for 6 days. A supernatant obtained by centrifuging the reaction mixture was subjected to an ultrafiltration device equipped with hollow fibers with exclusion molecular weight of 10,000 to collect a fraction of oligosaccharides having molecular weight of 10,000 or less. This fraction was designated as a sulfated glucuronofucan enzymatic digestion product fraction 1.

(2) The sulfated glucuronofucan enzymatic digestion product fraction 1 obtained in Example 2(1) was desalted using a desalting apparatus (Micro Acilyzer G3, Asahi Kasei). Imidazole and sodium chloride were added to the desalted sulfated glucuronofucan enzymatic digestion product fraction 1 at final concentrations of 5 mM and 20 mM, respectively. The resulting mixture was loaded onto a 1-l DEAE-Cellulofine A-800 column equilibrated with 5 mM imidazole-hydrochloride buffer (pH 7.0) containing 20 mM sodium chloride. After adequately washing with the same buffer, elution was then carried out with a gradient of 20 mM to 600 mM sodium chloride. The total sugar content and the total uronic acid content of each of the eluted fractions were measured according to the phenol-sulfuric acid method and the carbazole-sulfuric acid method, respectively. As a result, the eluted fractions formed at least eight distinct peaks. The fractions in each peak were combined, concentrated to 40 ml using an evaporator, loaded onto a Cellulofine GCL-25 column equilibrated with 10% ethanol and eluted with 10% ethanol for desalting. The sulfated glucuronofucan oligosaccharides, or the oligosaccharides, 1-(1) to (8) of the present invention were obtained as described above.

(3) The oligosaccharides 1-(1) to (8) obtained in Example 2(2) were subjected to analyses of saccharides at the reducing ends and saccharide compositions according to the fluorescence labeling method using 2-aminopyridine as well as determination of absolute configurations of fucose using Reagent for measuring urinary free fucise (UFC test kit Takara) (Takara Shuzo). As a result, the saccharide at the reducing end for each of the oligosaccharides 1-(1) to (8) was determined to be L-fucose. Regarding the saccharide composition, the oligosaccharide 1-(1) consisted only of fucose whereas the oligosaccharides 1-(2) to (8) consisted of fucose and glucuronic acid. Next, determination of the sulfuric acid content (measured according to the turbidimetric method using barium chloride) and the uronic acid content (measured according to the carbazole-sulfuric acid method), mass spectrometric analysis using a mass spectrometer API-III (Perkin-Elmer Sciex) and NMR analysis using a nuclear magnetic resonance apparatus JNM-α500 (Nippon Denshi) were carried out. Samples to be analyzed were subjected to structural analyses after exchange for heavy water according to a conventional method. Bonds of constituting saccharides were analyzed using the HMBC method, a method for $^1$H-detection of heteronuclei. The DQF-COSY method and the HOHAHA method were used for identification in $^1$H-NMR. The HSQC method was used for identification in $^{13}$C-NMR. Physical properties of the oligosaccharides 1-(1) to (8) are shown below.

(a) Physical Properties of the Oligosaccharide 1-(1)

Figure 7:
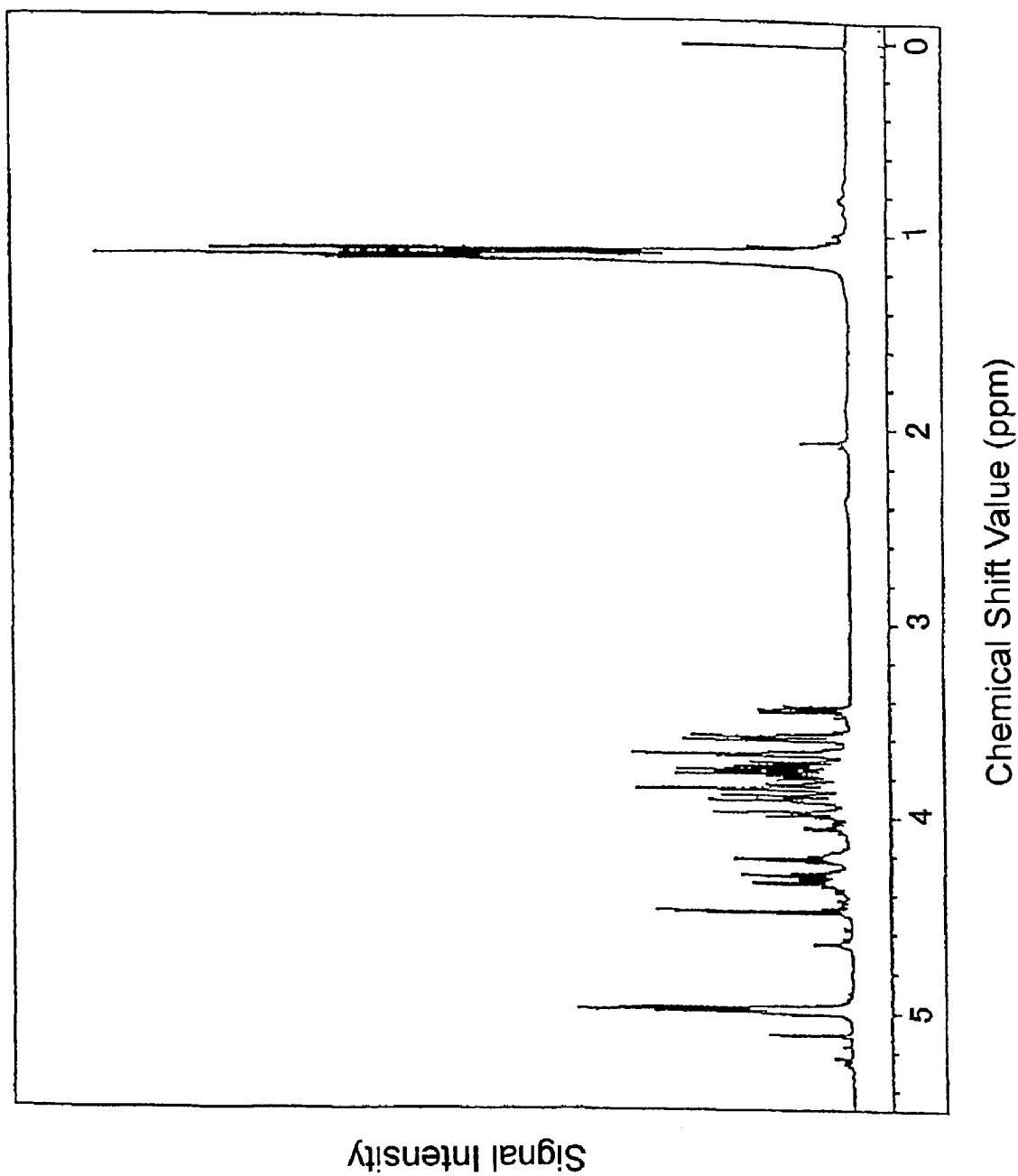
FIG. 7: a figure which illustrates the ¹H-NMR spectrum of the sulfated glucuronofucan oligosaccharide 1-(1) according to the present invention.
Figure 8:
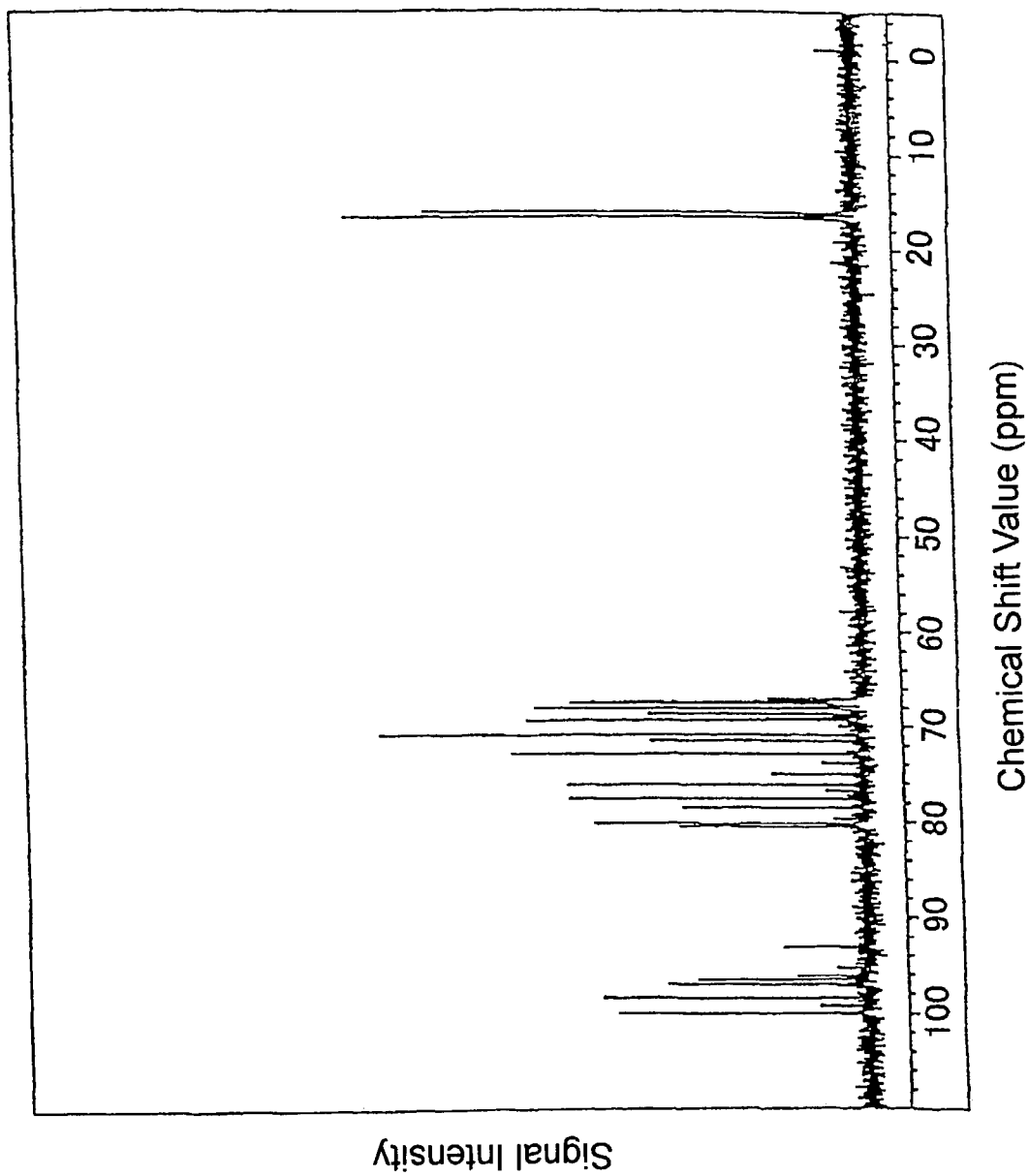
FIG. 8: a figure which illustrates the ¹³C-NMR spectrum of the sulfated glucuronofucan oligosaccharide 1-(1) according to the present invention.
Figure 9:
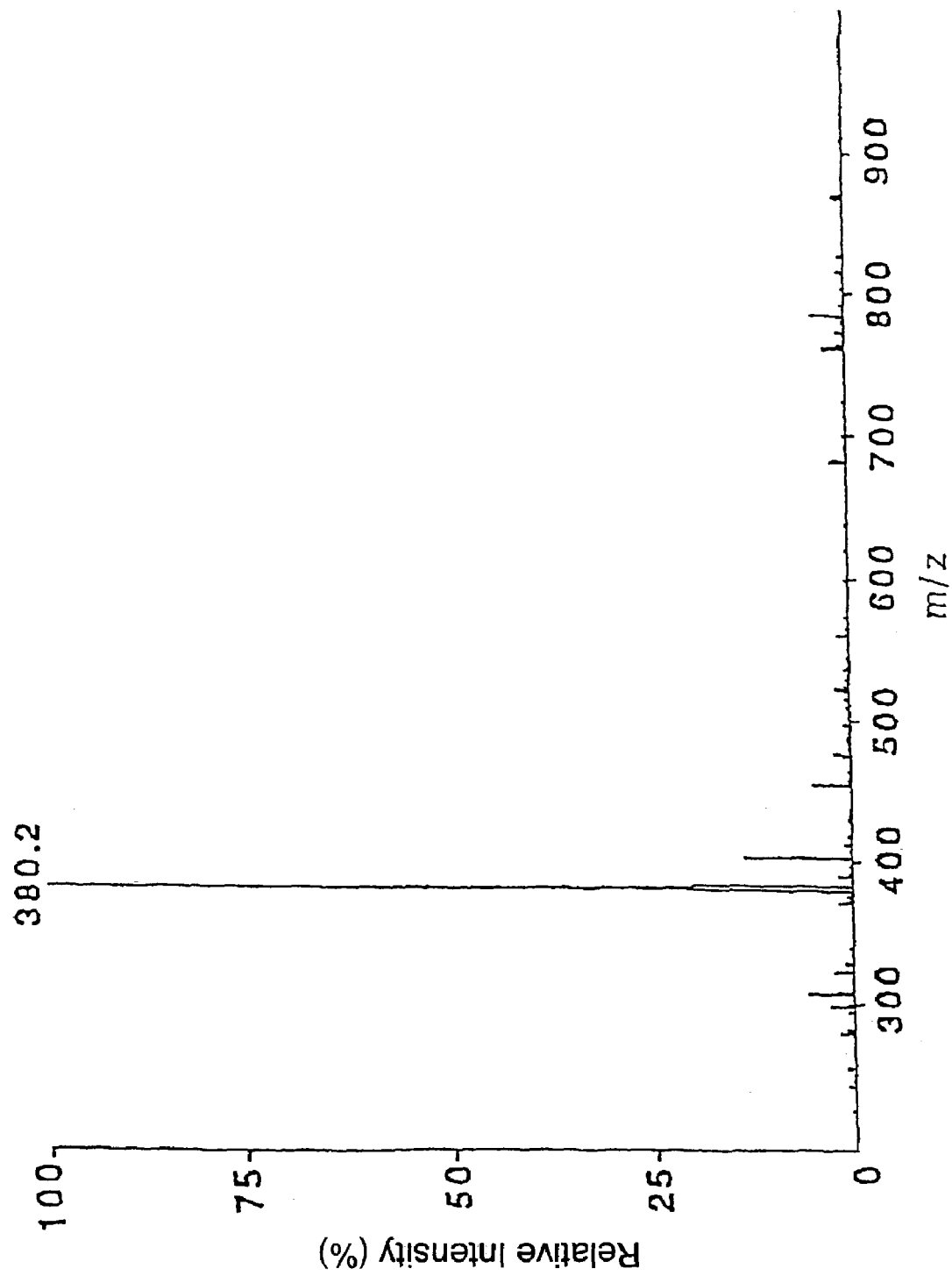
FIG. 9: a figure which illustrates the mass spectrum of the sulfated glucuronofucan oligosaccharide 1-(1) according to the present invention.

The results for mass spectrometric analysis and identification in NMR analysis are shown below. The $^1$H-NMR spectrum, $^{13}$C-NMR spectrum and mass spectrum of the sulfated glucuronofucan oligosaccharide 1-(1) of the present invention are illustrated in FIGS. 7, 8 and 9, respectively. In FIGS. 7 and 8, the vertical axes represent the signal intensity and the horizontal axes represent the chemical shift value (ppm). In FIG. 9, the vertical axis represents the relative intensity and the horizontal axis represents the m/z value.

Molecular weight: 762

MS m/z 380.2 $[M-2H^+]^{2-}$

Results of $^1$H-NMR and $^{13}$C-NMR analyses are shown in Table 1.

TABLE 1

| | Chemical shift value (ppm) | |
|---|---|---|
| | $^{13}$C-NMR | $^1$H-NMR Chemical shift value, multiplicity, coupling constant |
| F1-1 | 97.0 | 4.48, d, 7.6 |
| F1-2 | 70.8 | 3.44, dd, 7.6, 10.1 |
| F1-3 | 78.4 | 3.59, dd, 3.7, 10.1 |
| F1-4 | 68.6 | 3.86, d, 3.7 |
| F1-5 | 71.4 | 3.66, q, 6.8 |
| F1-6 | 16.5 | 1.13, d, 6.8 |
| F2-1 | 96.5 | 4.98, d, 4.0 |
| F2-2 | 67.5 | 3.85, dd, 4.0, 10.4 |
| F2-3 | 77.5 | 3.98, dd, 3.1, 10.4 |
| F2-4 | 80.5 | 4.65, d, 3.1 |
| F2-5 | 67.2 | 4.30, q, 6.8 |
| F2-6 | 16.5 | 1.13, d, 6.8 |
| F3-1 | 99.9 | 4.99, d, 4.0 |
| F3-2 | 68.0 | 3.72, dd, 4.0, 10.6 |
| F3-3 | 76.1 | 3.90, dd, 3.0, 10.6 |
| F3-4 | 80.3 | 4.65, d, 3.0 |
| F3-5 | 67.4 | 4.34, q, 6.7 |
| F3-6 | 16.5 | 1.11, d, 6.7 |
| F4-1 | 98.4 | 4.97, d, 4.0 |
| F4-2 | 69.3 | 3.59, dd, 4.0, 10.4 |
| F4-3 | 70.8 | 3.76, dd, 3.4, 10.4 |
| F4-4 | 72.8 | 3.68, d, 3.4 |
| F4-5 | 68.0 | 4.21, q, 6.7 |
| F4-6 | 16.0 | 1.09, d, 6.7 |

Saccharide composition: L-fucose (4 molecules)

Sulfate group: 2 molecules

The numbers for peak identification in $^1$H-NMR and $^{13}$C-NMR are as indicated in formula (IV) below:

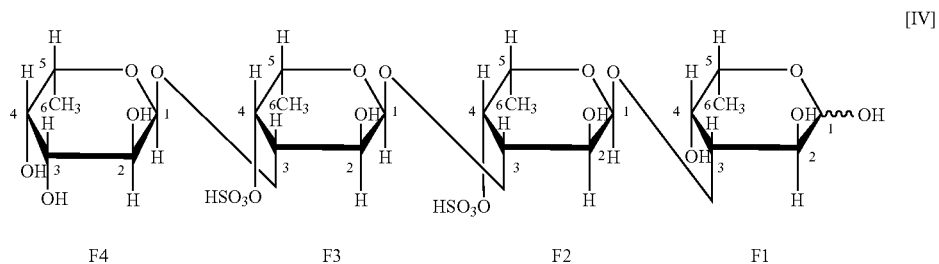

[IV]

F4　　　　F3　　　　F2　　　　F1

(b) Physical Properties of the Oligosaccharide 1-(2)

Figure 10:
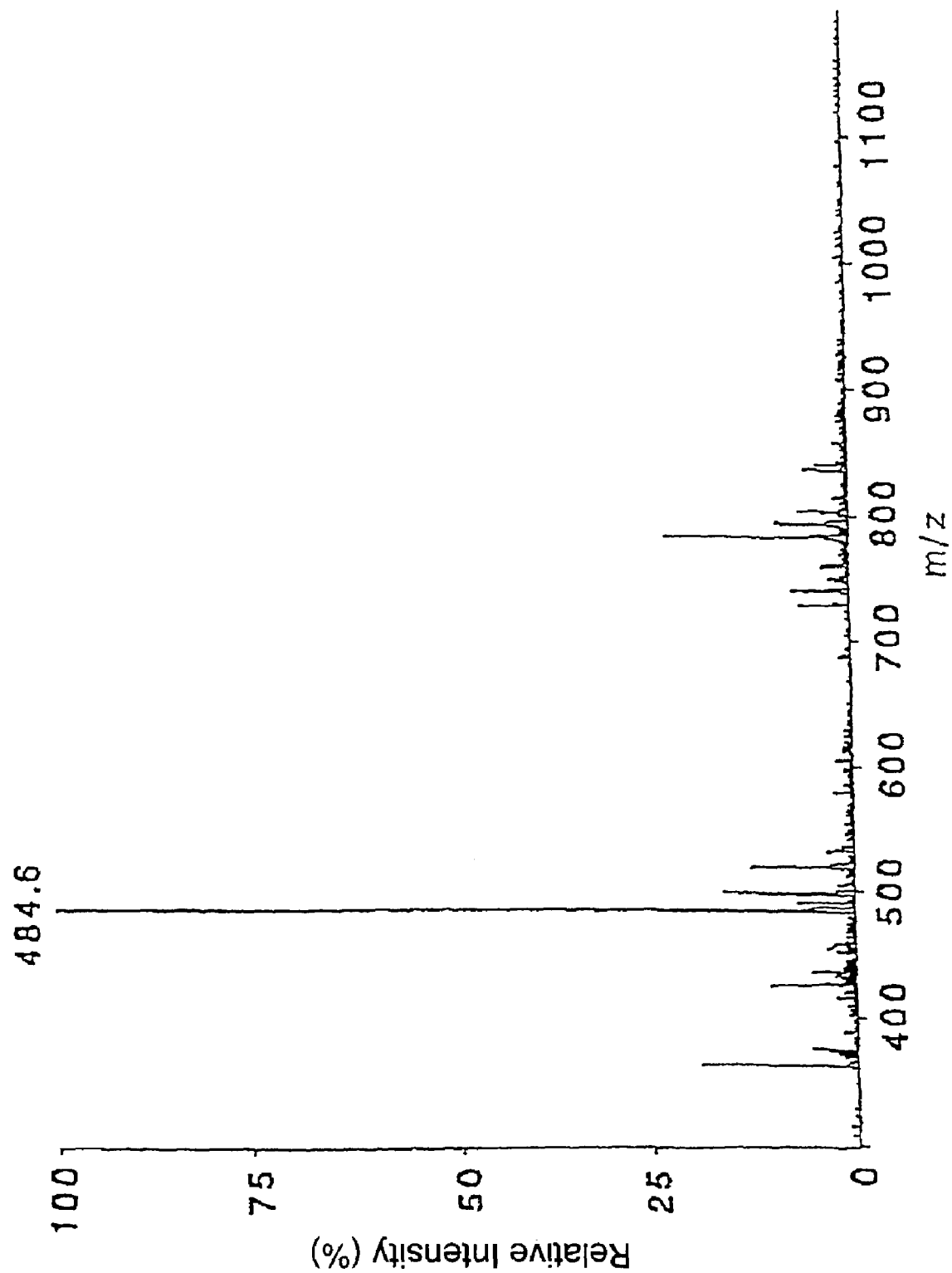
FIG. 10: a figure which illustrates the mass spectrum of the sulfated glucuronofucan oligosaccharide 1-(2) according to the present invention.

The results for mass spectrometric analysis are shown below. The mass spectrum of the sulfated glucuronofucan oligosaccharide 1-(2) of the present invention is illustrated in FIG. 10. In FIG. 10, the vertical axis represents the relative intensity and the horizontal axis represents the m/z value.

Molecular weight: 1456
MS m/z 484.6 $[M-3H^+]^{3-}$

Saccharide composition: L-fucose:D-glucuronic acid=7:1

Sulfate group: 3 molecules (c) Physical Properties of the Oligosaccharide 1-(3)

Figure 11:
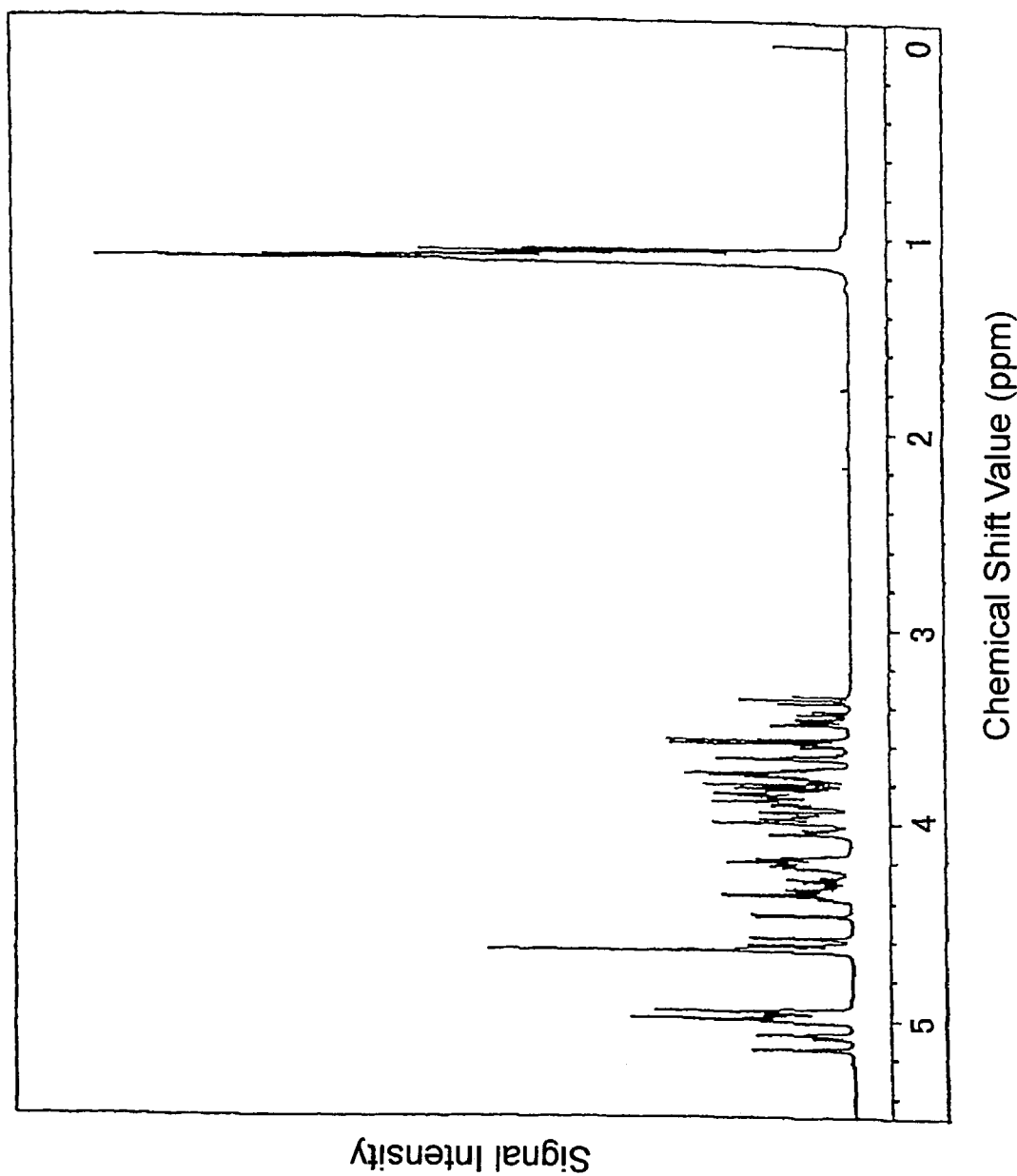
FIG. 11: a figure which illustrates the $^1$H-NMR spectrum of the sulfated glucuronofucan oligosaccharide 1-(3) according to the present invention.
Figure 12:
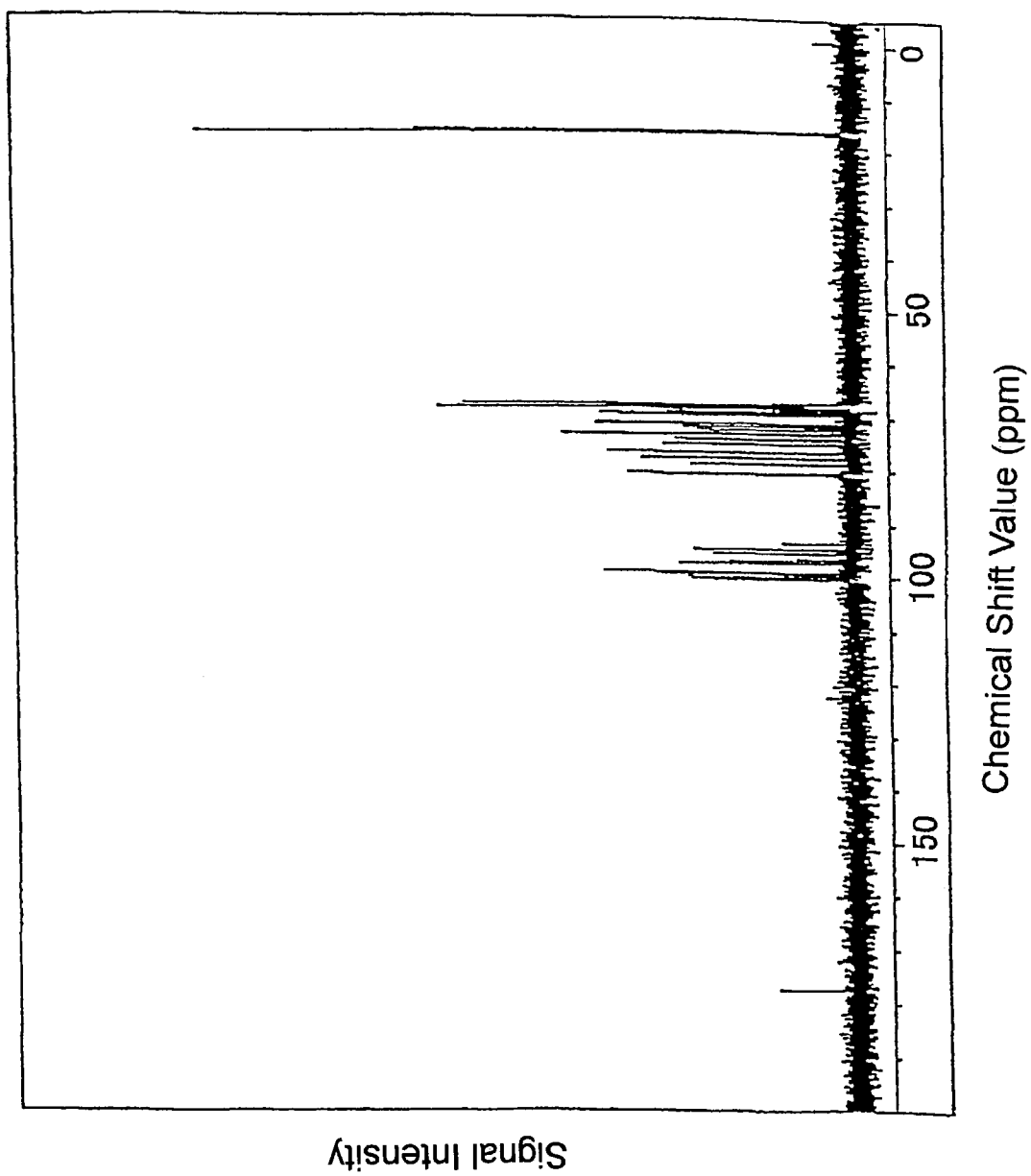
FIG. 12: a figure which illustrates the $^{13}$C-NMR spectrum of the sulfated glucuronofucan oligosaccharide 1-(3) according to the present invention.
Figure 13:
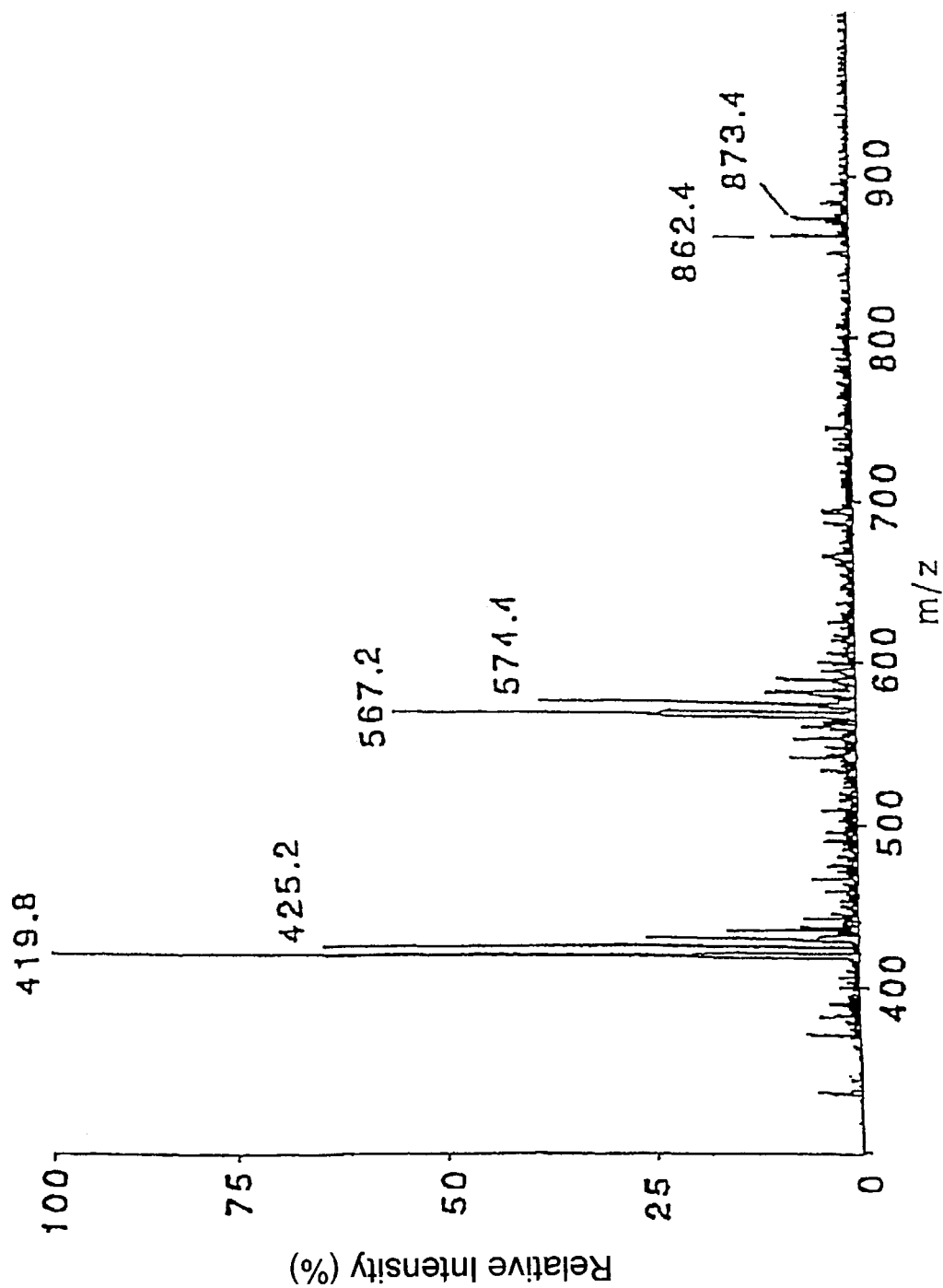
FIG. 13: a figure which illustrates the mass spectrum of the sulfated glucuronofucan oligosaccharide 1-(3) according to the present invention.

The results for mass spectrometric analysis and identification in NMR analysis are shown below. The $^1$H-NMR spectrum, $^{13}$C-NMR spectrum and mass spectrum of the sulfated glucuronofucan oligosaccharide 1-(3) of the present invention are illustrated in FIGS. 11, 12 and 13, respectively. In FIGS. 11 and 12, the vertical axes represent the signal intensity and the horizontal axes represent the chemical shift value (ppm). In FIG. 13, the vertical axis represents the relative intensity and the horizontal axis represents the m/z value.

Molecular weight: 1682
MS m/z 873.4 $[M+3Na^+-5H^+]^{2-}$, 862.4 $[M+2Na^+-4H^+]^{2-}$, 574.4 $[M+2Na^+-5H^+]^{3-}$, 567.2 $[M+Na^+-4H^+]^{3-}$, 425.2 $[M+Na^+-5H^+]^{4-}$, 419.8 $[M-4H^+]^{4-}$ Results of $^1$H-NMR and $^{13}$C-NMR analyses are shown in Table 2.

TABLE 2

| | Chemical shift value (ppm) | |
|---|---|---|
| | | $^1$H-NMR |
| | $^{13}$C-NMR | Chemical shift value, multiplicity, coupling constant |
| F1-1 | 97.1 | 4.47, d, 7.9 |
| F1-2 | 70.9 | 3.44, dd, 7.9, 10.1 |
| F1-3 | 78.6 | 3.57, dd, 3.2, 10.1 |
| F1-4 | 68.7 | 3.85, d, 3.2 |
| F1-5 | 71.5 | 3.65, q, 6.7 |
| F1-6 | 16.6 | 1.13, d, 6.7 |
| F2-1 | 96.6 | 4.98, d, 4.0 |
| F2-2 | 67.6 | 3.86, dd, 4.0, 8.6 |
| F2-3 | 77.6 | 3.97, dd, 2.9, 8.6 |
| F2-4 | 80.6 | 4.65, d, 2.9 |
| F2-5 | 67.4 | 4.29, q, 6.7 |
| F2-6 | 16.7 | 1.11, d, 6.7 |
| F3-1 | 100.1 | 4.99, d, 4.0 |
| F3-2 | 68.1 | 3.74, dd, 4.0, 10.4 |
| F3-3 | 77.4 | 3.89, dd, 2.8, 10.4 |
| F3-4 | 80.6 | 4.62, d, 2.8 |
| F3-5 | 67.4 | 4.33, q, 6.7 |
| F3-6 | 16.6 | 1.12, d, 6.7 |

TABLE 2-continued

| | Chemical shift value (ppm) | |
|---|---|---|
| | | $^1$H-NMR |
| | $^{13}$C-NMR | Chemical shift value, multiplicity, coupling constant |
| F4-1 | 99.6 | 4.95, d, 4.0 |
| F4-2 | 67.7 | 3.72, dd, 4.0, 10.4 |
| F4-3 | 74.8 | 3.86, dd, 3.1, 10.4 |
| F4-4 | 69.1 | 3.95, d, 3.1 |
| F4-5 | 68.1 | 4.22, q, 6.8 |
| F4-6 | 16.2 | 1.09, d, 6.8 |
| F5-1 | 95.1 | 5.00, d, 4.0 |
| F5-2 | 71.4 | 4.04, dd, 4.0, 10.4 |
| F5-3 | 73.7 | 4.19, dd, 2.8, 10.4 |
| F5-4 | 68.1 | 4.00, d, 2.8 |
| F5-5 | 67.4 | 4.20, q, 6.7 |
| F5-6 | 16.2 | 1.11, d, 6.7 |
| F6-1 | 94.3 | 5.08, d, 4.0 |
| F6-2 | 67.4 | 3.89, dd, 4.0, 10.4 |
| F6-3 | 76.5 | 3.99, dd, 2.4, 10.4 |
| F6-4 | 80.3 | 4.58, d, 2.4 |
| F6-5 | 67.8 | 4.37, q, 6.7 |
| F6-6 | 16.7 | 1.12, d, 6.7 |
| F7-1 | 99.1 | 4.99, d, 4.0 |
| F7-2 | 68.1 | 3.74, dd, 4.0, 10.4 |
| F7-3 | 76.4 | 3.91, dd, 3.0, 10.4 |
| F7-4 | 80.2 | 4.64, d, 3.0 |
| F7-5 | 67.4 | 4.37, q, 6.7 |
| F7-6 | 16.7 | 1.12, d, 6.7 |
| F8-1 | 98.7 | 4.96, d, 4.0 |
| F8-2 | 69.4 | 3.57, dd, 4.0, 10.1 |
| F8-3 | 70.9 | 3.76, dd, 3.0, 10.1 |
| F8-4 | 73.0 | 3.66, d, 3.0 |
| F8-5 | 68.1 | 4.23, q, 6.7 |
| F8-6 | 16.1 | 1.07, d, 6.7 |
| GA-1 | 100.4 | 5.16, d, 4.0 |
| GA-2 | 72.1 | 3.48, dd, 4.0, 9.8 |
| GA-3 | 74.0 | 3.59, t, 9.8 |
| GA-4 | 72.7 | 3.36, t, 9.8 |
| GA-5 | 73.7 | 3.81, d, 9.8 |
| GA-6 | 177.3 | |

Saccharide composition: L-fucose:D-glucuronic acid=8:1

Sulfate group: 4 molecules

The numbers for peak identification in $^1$H-NMR and $^{13}$C-NMR are as indicated in formula (V) below:

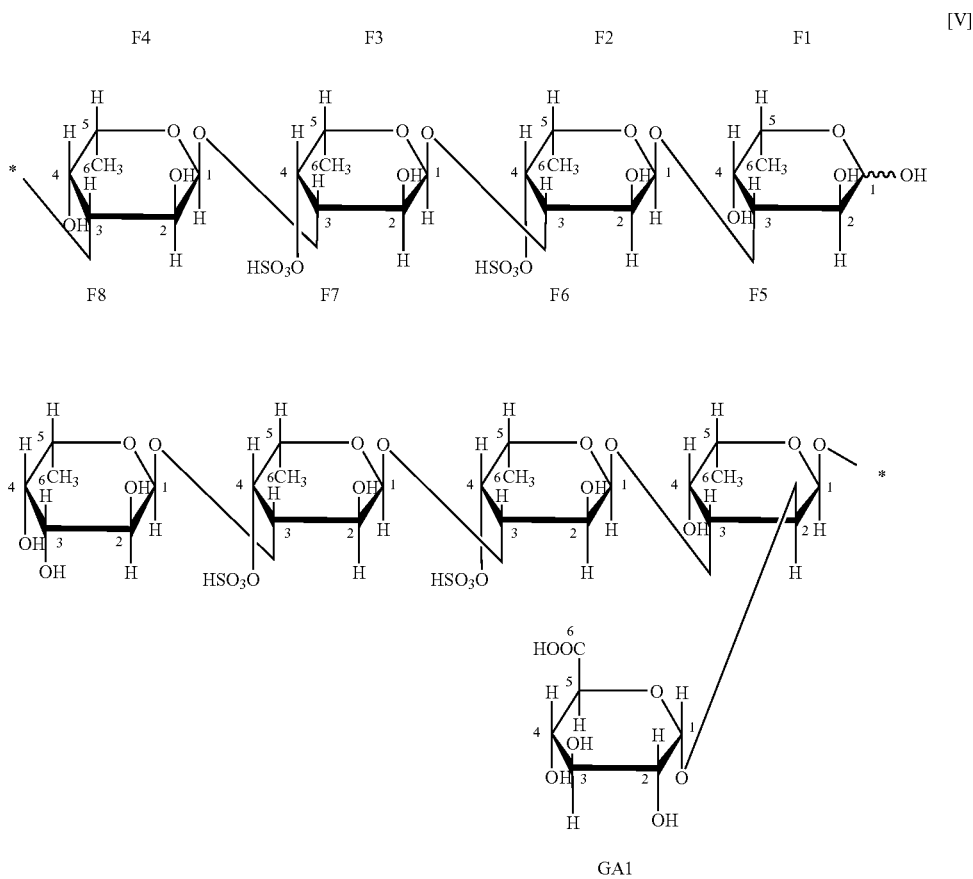

GA1

(d) Physical Properties of the Oligosaccharide 1-(4)

Figure 14:
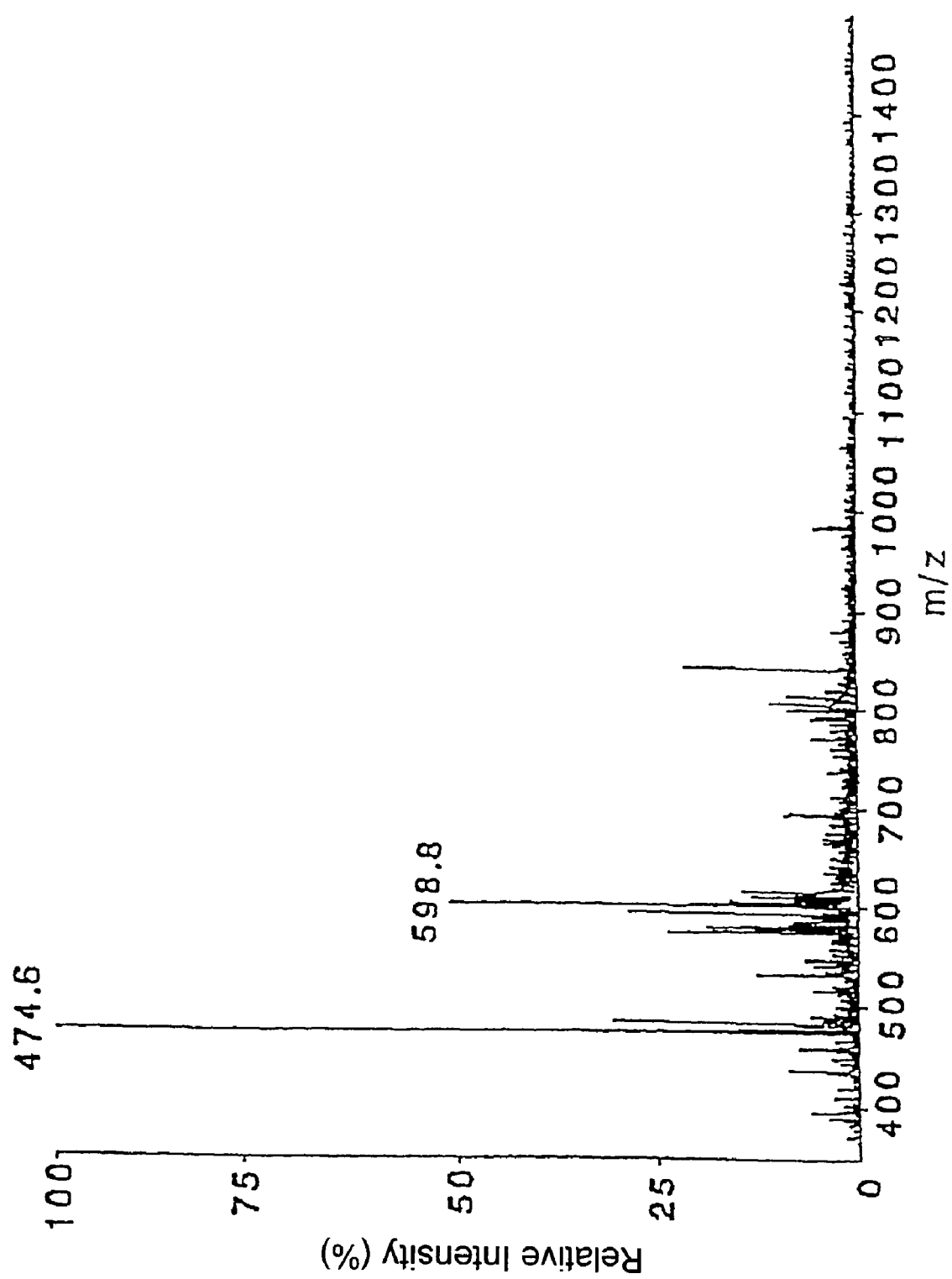
FIG. 14: a figure which illustrates the mass spectrum of the sulfated glucuronofucan oligosaccharide 1-(4) according to the present invention.

The results for mass spectrometric analysis are shown below. The mass spectrum of the sulfated glucuronofucan oligosaccharide 1-(4) of the present invention is illustrated in FIG. 14. In FIG. 14, the vertical axis represents the relative intensity and the horizontal axis represents the m/z value.

Molecular weight: 2376

MS m/z 598.8 $[M+Na^+-5H^+]^{4-}$, 474.6 $[M-5H^+]^{5-}$

Saccharide composition: L-fucose:D-glucuronic acid=11:2

Sulfate group: 5 molecules (e) Physical Properties of the Oligosaccharide 1-(5)

Figure 15:
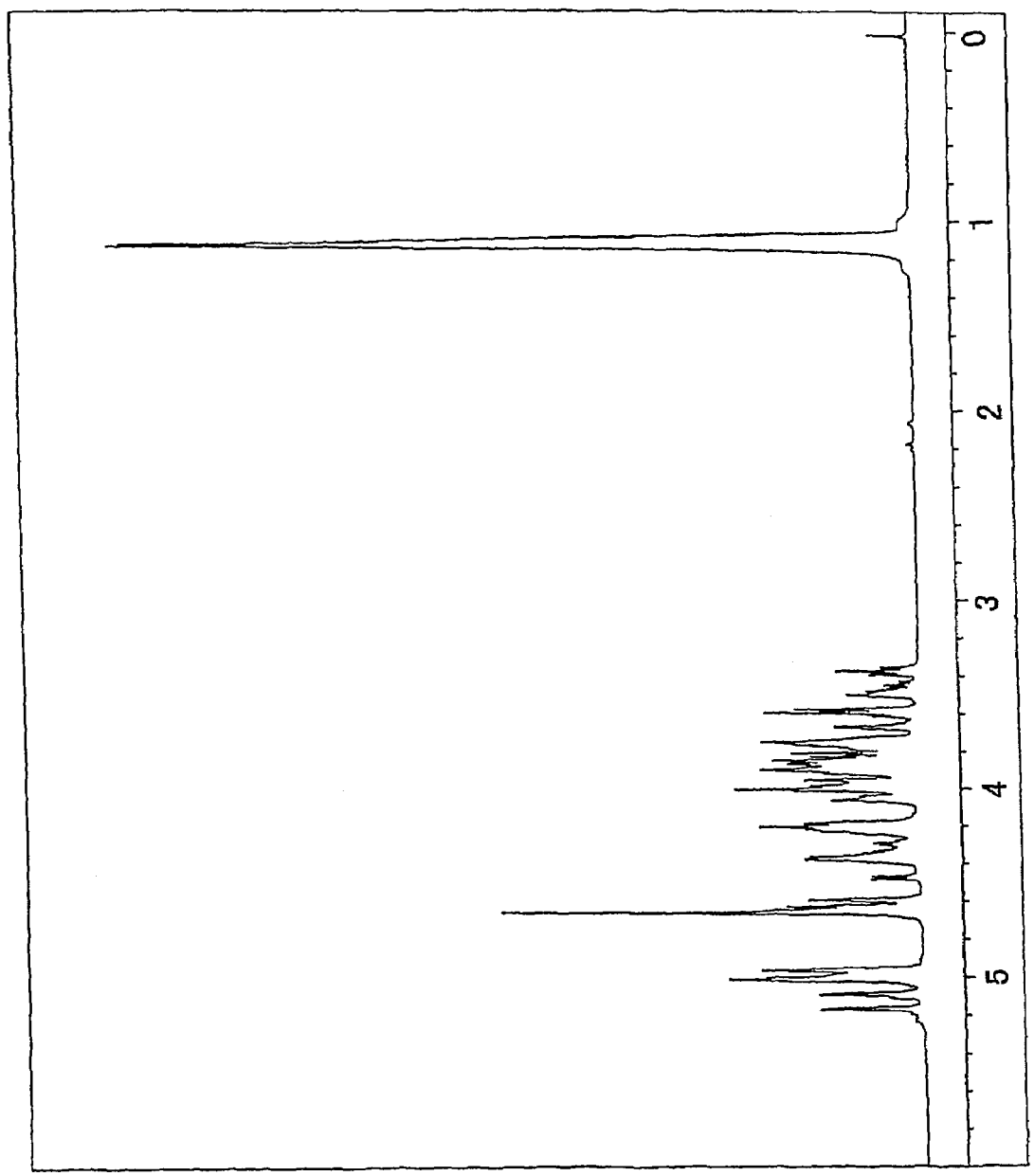
FIG. 15: a figure which illustrates the $^1$H-NMR spectrum of the sulfated glucuronofucan oligosaccharide 1-(5) according to the present invention.
Figure 16:
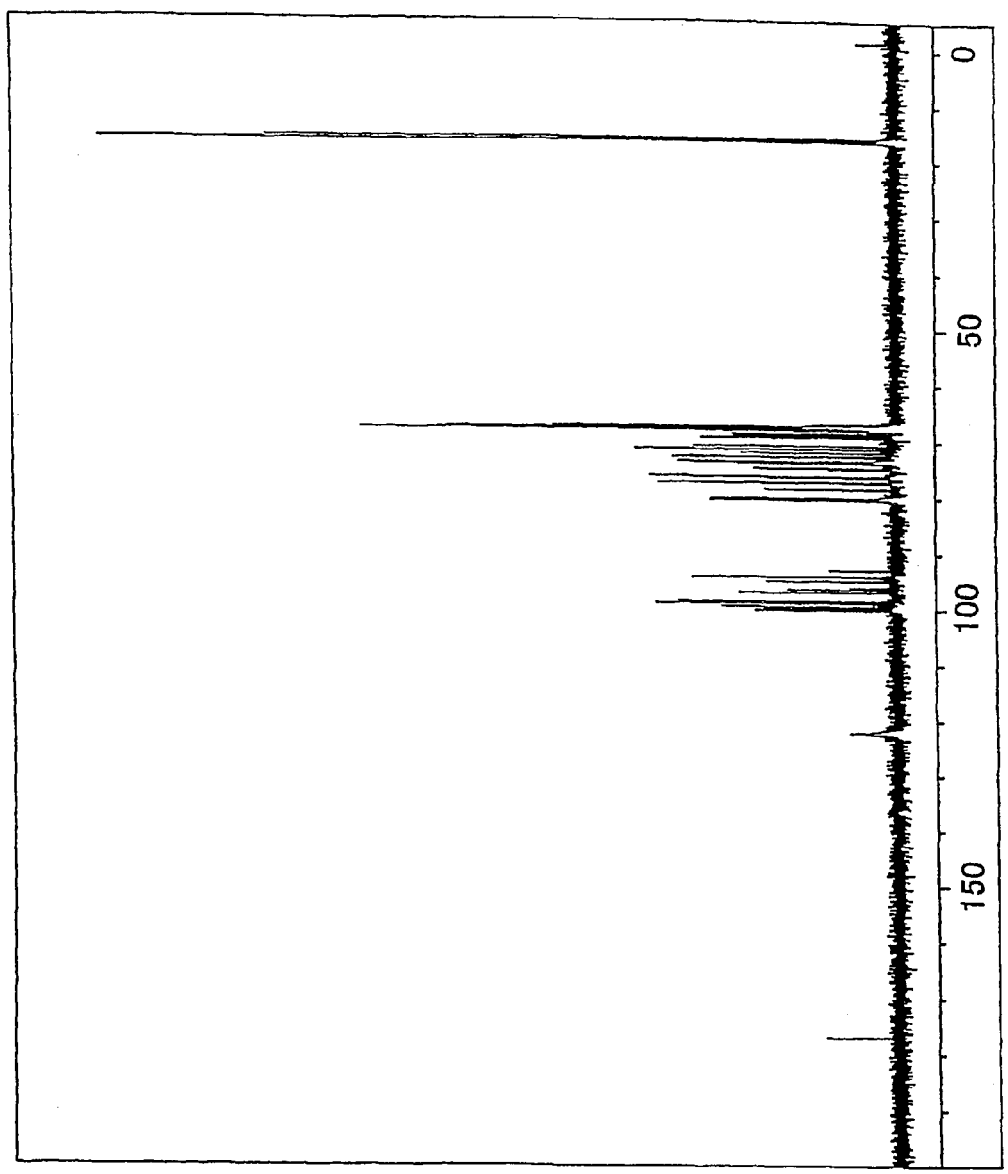
FIG. 16: a figure which illustrates the $^{13}$C-NMR spectrum of the sulfated glucuronofucan oligosaccharide 1-(5) according to the present invention.
Figure 17:
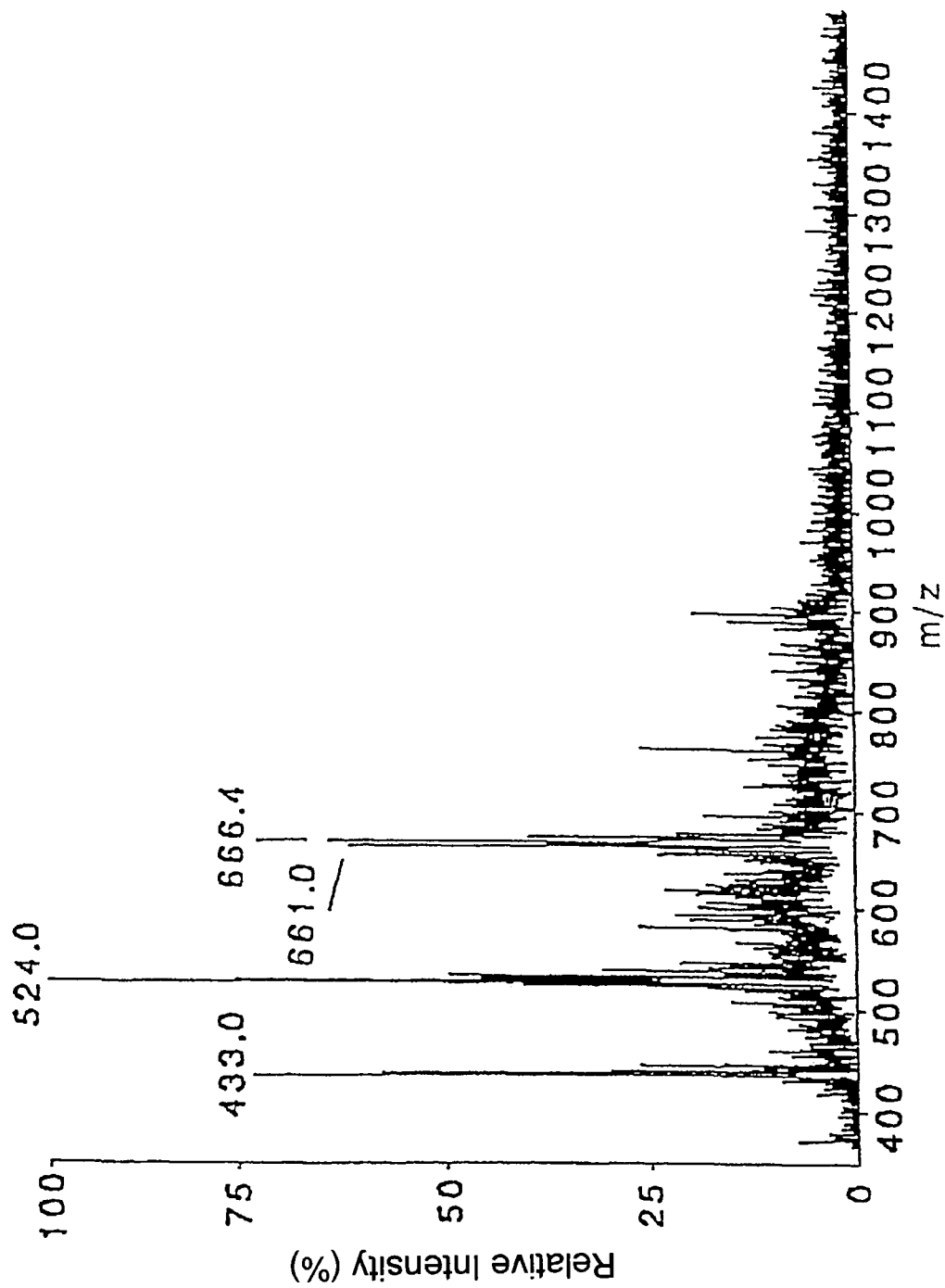
FIG. 17: a figure which illustrates the mass spectrum of the sulfated glucuronofucan oligosaccharide 1-(5) according to the present invention.

The results for mass spectrometric analysis are shown below. The $^1$H-NMR spectrum, $^{13}$C-NMR spectrum and mass spectrum of the sulfated glucuronofucan oligosaccharide 1-(5) of the present invention are illustrated in FIGS. 15, 16 and 17, respectively. In FIGS. 15 and 16, the vertical axes represent the signal intensity and the horizontal axes represent the chemical shift value (ppm). In FIG. 17, the vertical axis represents the relative intensity and the horizontal axis represents the m/z value.

Molecular weight: 2602

MS m/z 666.4 $[M+3Na^+-7H^+]^{4-}$, 661.0 $[M+2Na^+-6H^+]^{4-}$, 524.0 $[M+Na^+-6H^+]^{5-}$, 433.0 $[M-6H^+]^{6-}$

Results of $^1$H-NMR and $^{13}$C-NMR analyses are shown in Table 3.

TABLE 3

| | Chemical shift value (ppm) | |
|---|---|---|
| | $^{13}$C-NMR | $^1$H-NMR Chemical shift value, multiplicity, coupling constant |
| F1-1 | 96.8 | 4.48, d, 8.0 |
| F1-2 | 70.6 | 3.45, dd, 8.0, 9.5 |
| F1-3 | 78.3 | 3.58, m |
| F1-4 | 68.3 | 3.85, m |
| F1-5 | 71.2 | 3.66, q, 6.7 |
| F1-6 | 16.2 | 1.14, d, 6.7 |
| F2-1 | 96.3 | 4.99, d, 4.0 |
| F2-2 | 67.4 | 3.86, m |
| F2-3 | 77.1 | 3.98, m |
| F2-4 | 80.2 | 4.65, m |
| F2-5 | 67.0 | 4.30, q, 6.7 |
| F2-6 | 16.3 | 1.10, d, 6.7 |
| F3-1 | 99.7 | 5.00, d, 4.0 |
| F3-2 | 67.8 | 3.75, m |
| F3-3 | 77.0 | 3.90, m |
| F3-4 | 80.2 | 4.63, m |
| F3-5 | 67.4 | 4.34, q, 6.7 |
| F3-6 | 16.3 | 1.13, d, 6.7 |
| F4-1 | 99.2 | 4.96, d, 4.0 |
| F4-2 | 67.4 | 3.73, m |
| F4-3 | 74.5 | 3.86, m |
| F4-4 | 68.7 | 3.96, m |
| F4-5 | 67.8 | 4.22, q, 6.7 |
| F4-6 | 15.8 | 1.10, d, 6.7 |
| F5-1 | 94.7 | 5.01, d, 4.0 |
| F5-2 | 71.1 | 4.05, dd, 4.0, 10.0 |

TABLE 3-continued

| | Chemical shift value (ppm) | |
|---|---|---|
| $^{13}$C-NMR | | $^1$H-NMR Chemical shift value, multiplicity, coupling constant |
| F5-3 | 73.4 | 4.20, m |
| F5-4 | 67.8 | 4.01, m |
| F5-5 | 67.0 | 4.21, q, 6.7 |
| F5-6 | 15.8 | 1.12, d, 6.7 |
| F6-1 | 94.0 | 5.09, d, 4.0 |
| F6-2 | 67.0 | 3.90, m |
| F6-3 | 76.2 | 3.99, m |
| F6-4 | 79.9 | 4.60, m |
| F6-5 | 67.4 | 4.38, q, 6.7 |
| F6-6 | 16.4 | 1.13, d, 6.7 |
| F7-1 | 98.7 | 5.00, d, 4.0 |
| F7-2 | 67.8 | 3.75, m |
| F7-3 | 76.0 | 3.91, m |
| F7-4 | 79.8 | 4.65, m |
| F7-5 | 67.4 | 4.38, q, 6.7 |
| F7-6 | 16.4 | 1.13, d, 6.7 |
| F8-1 | 99.2 | 4.96, d, 4.0 |
| F8-2 | 67.4 | 3.73, m |
| F8-3 | 74.5 | 3.86, m |
| F8-4 | 68.7 | 3.96, m |
| F8-5 | 67.8 | 4.22, q, 6.7 |
| F8-6 | 15.8 | 1.10, d, 6.7 |
| F9-1 | 94.7 | 5.01, d, 4.0 |
| F9-2 | 71.1 | 4.05, dd, 4.0, 10.0 |
| F9-3 | 73.4 | 4.20, m |
| F9-4 | 67.8 | 4.01, m |
| F9-5 | 67.0 | 4.21, q, 6.7 |
| F9-6 | 15.8 | 1.12, d, 6.7 |
| F10-1 | 94.0 | 5.09, d, 4.0 |
| F10-2 | 67.0 | 3.90, m |
| F10-3 | 76.2 | 3.99, m |
| F10-4 | 79.9 | 4.60, m |
| F10-5 | 67.4 | 4.38, q, 6.7 |
| F10-6 | 16.4 | 1.13, d, 6.7 |
| F11-1 | 98.7 | 5.00, d, 4.0 |
| F11-2 | 67.8 | 3.75, m |
| F11-3 | 76.0 | 3.91, m |
| F11-4 | 79.8 | 4.65, m |
| F11-5 | 67.4 | 4.38, q, 6.7 |
| F11-6 | 16.4 | 1.13, d, 6.7 |
| F12-1 | 98.3 | 4.96, d, 4.0 |
| F12-2 | 69.1 | 3.58, m |
| F12-3 | 70.5 | 3.77, m |
| F12-4 | 72.6 | 3.67, d, 4.0 |
| F12-5 | 67.8 | 4.23, q, 6.7 |
| F12-6 | 15.8 | 1.08, d, 6.7 |
| GA1-1 | 100.0 | 5.16, d, 4.0 |
| GA1-2 | 71.8 | 3.49, dd, 4.0, 10.0 |
| GA1-3 | 73.6 | 3.60, t, 10.0 |
| GA1-4 | 72.4 | 3.37, t, 10.0 |
| GA1-5 | 73.2 | 3.82, d, 10.0 |
| GA1-6 | 176.9 | |
| GA2-1 | 100.0 | 5.16, d, 4.0 |
| GA2-2 | 71.8 | 3.49, dd, 4.0, 10.0 |
| GA2-3 | 73.6 | 3.60, t, 10.0 |
| GA2-4 | 72.4 | 3.37, t, 10.0 |
| GA2-5 | 73.2 | 3.82, d, 10.0 |
| GA2-6 | 176.9 | |

Saccharide composition: L-fucose:D-glucuronic acid=12:2

Sulfate group: 6 molecules

The numbers for peak identification in $^1$H-NMR and $^{13}$C-NMR are as indicated in formula (XI) below:

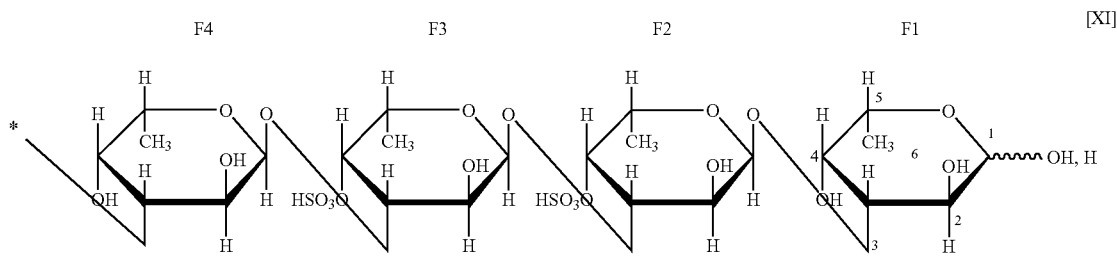

-continued

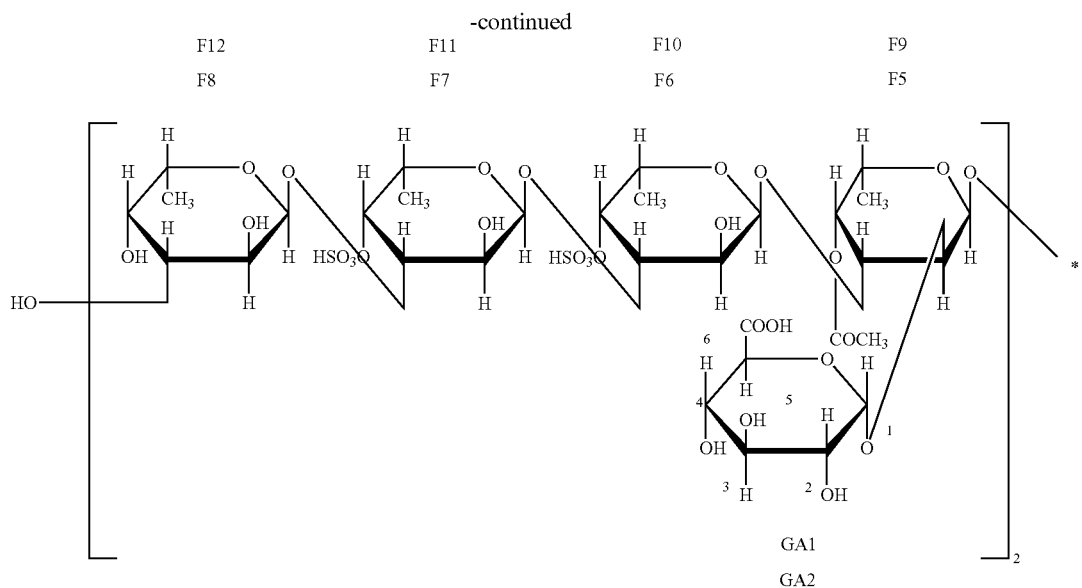

This substance is referred to as 12Fuc-6S-2GlcUA hereinafter.

(f) Physical Properties of the Oligosaccharide 1-(6)

Figure 18:
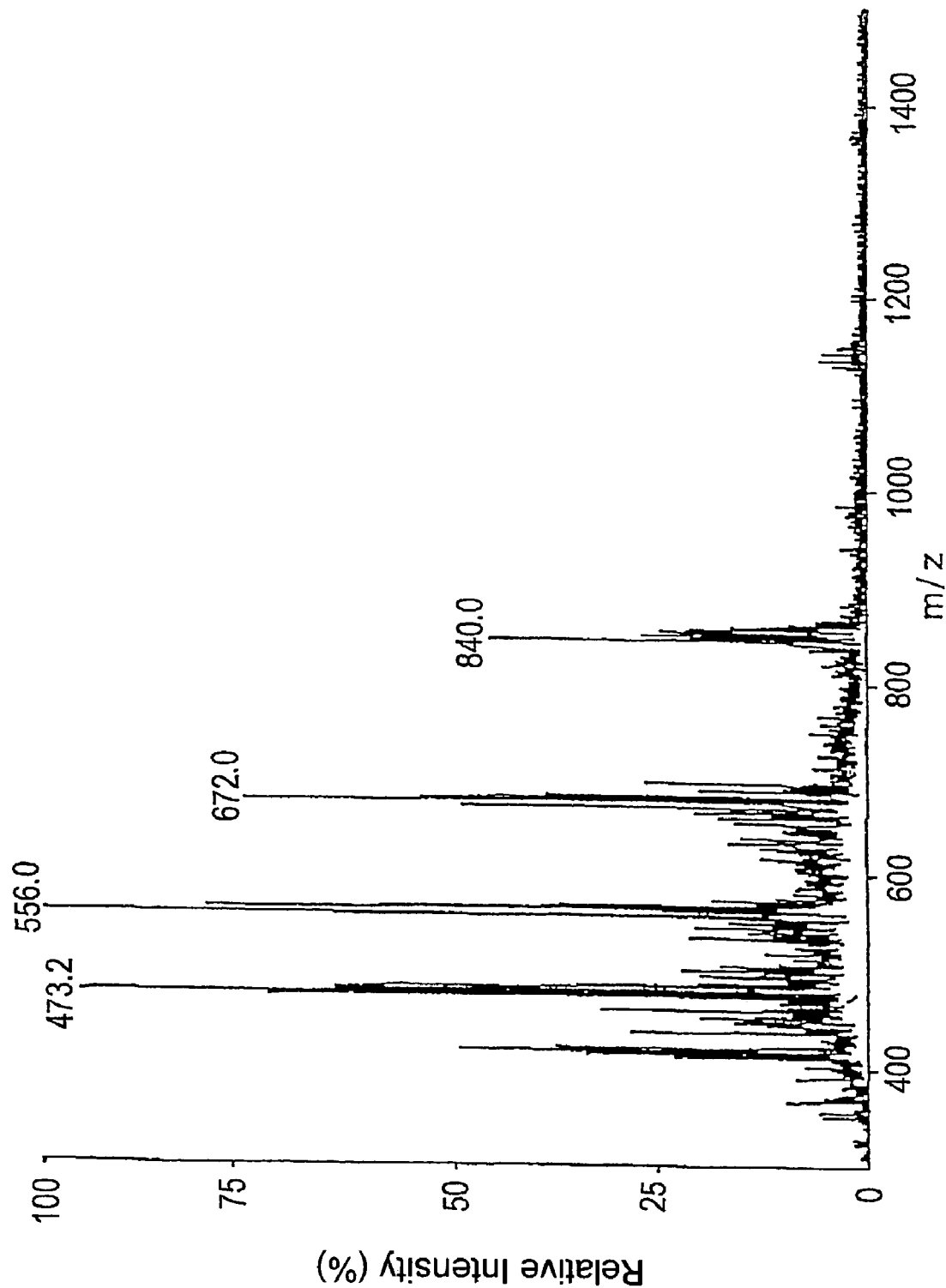
FIG. 18: a figure which illustrates the mass spectrum of the sulfated glucuronofucan oligosaccharide 1-(6) according to the present invention.

The results for mass spectrometric analysis are shown below. The mass spectrum of the sulfated glucuronofucan oligosaccharide 1-(6) of the present invention is illustrated in FIG. 18. In FIG. 18, the vertical axis represents the relative intensity and the horizontal axis represents the m/z value.

Molecular weight: 3296

MS m/z 840.0 $[M+3Na^+-7H^+]^{4-}$, 672.0 $[M+3Na^+-8H^+]^{5-}$, 556.0 $[M+2Na^+-8H^+]^{6-}$, 473.2 $[M+Na^+-8H^+]_{7-}$

Saccharide composition: L-fucose:D-glucuronic acid=15:3

Sulfate group: 7 molecules (g) Physical Properties of the Oligosaccharide 1-(7)

Figure 19:
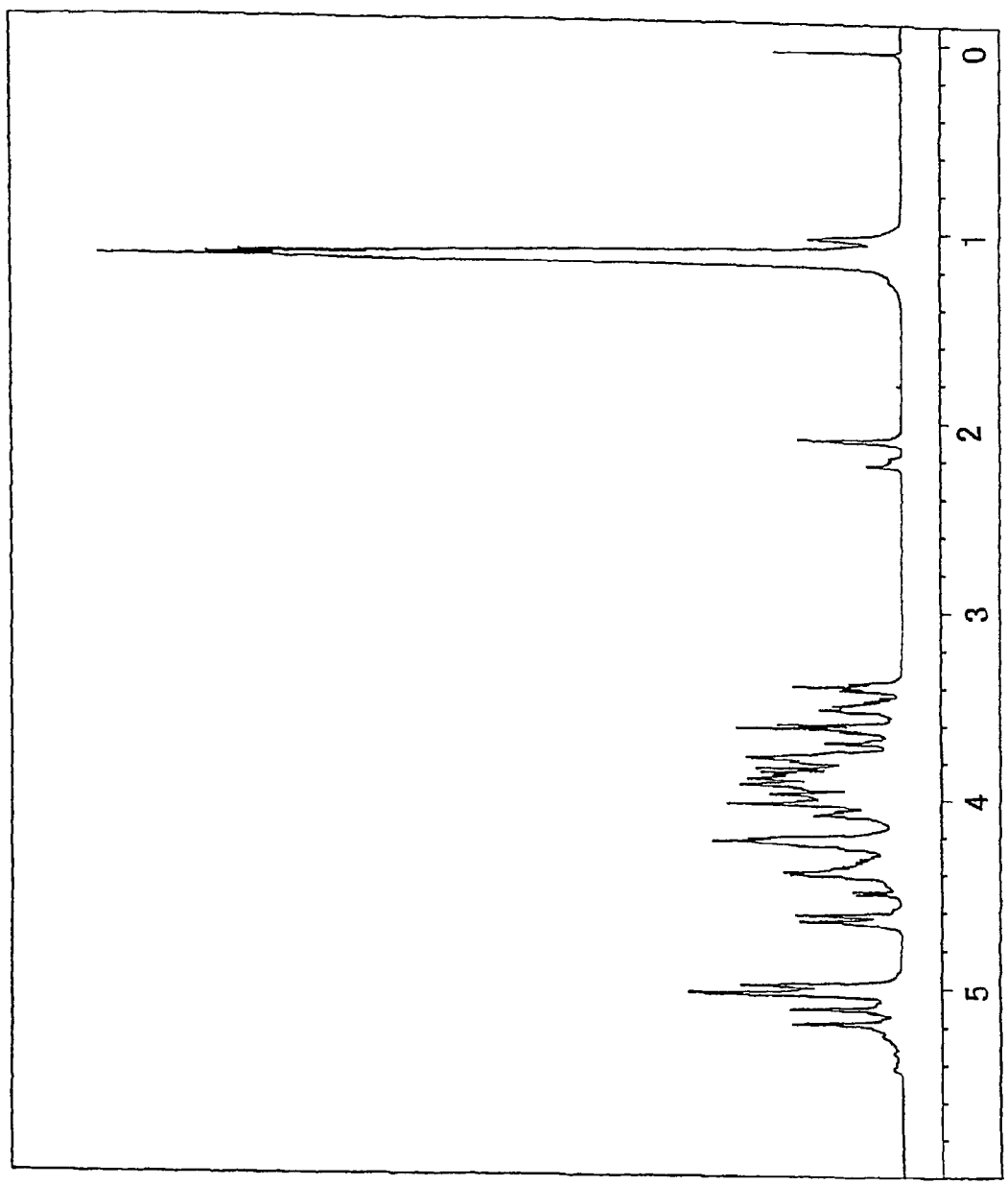
FIG. 19: a figure which illustrates the $^1$H-NMR spectrum of the sulfated glucuronofucan oligosaccharide 1-(7) according to the present invention.
Figure 20:
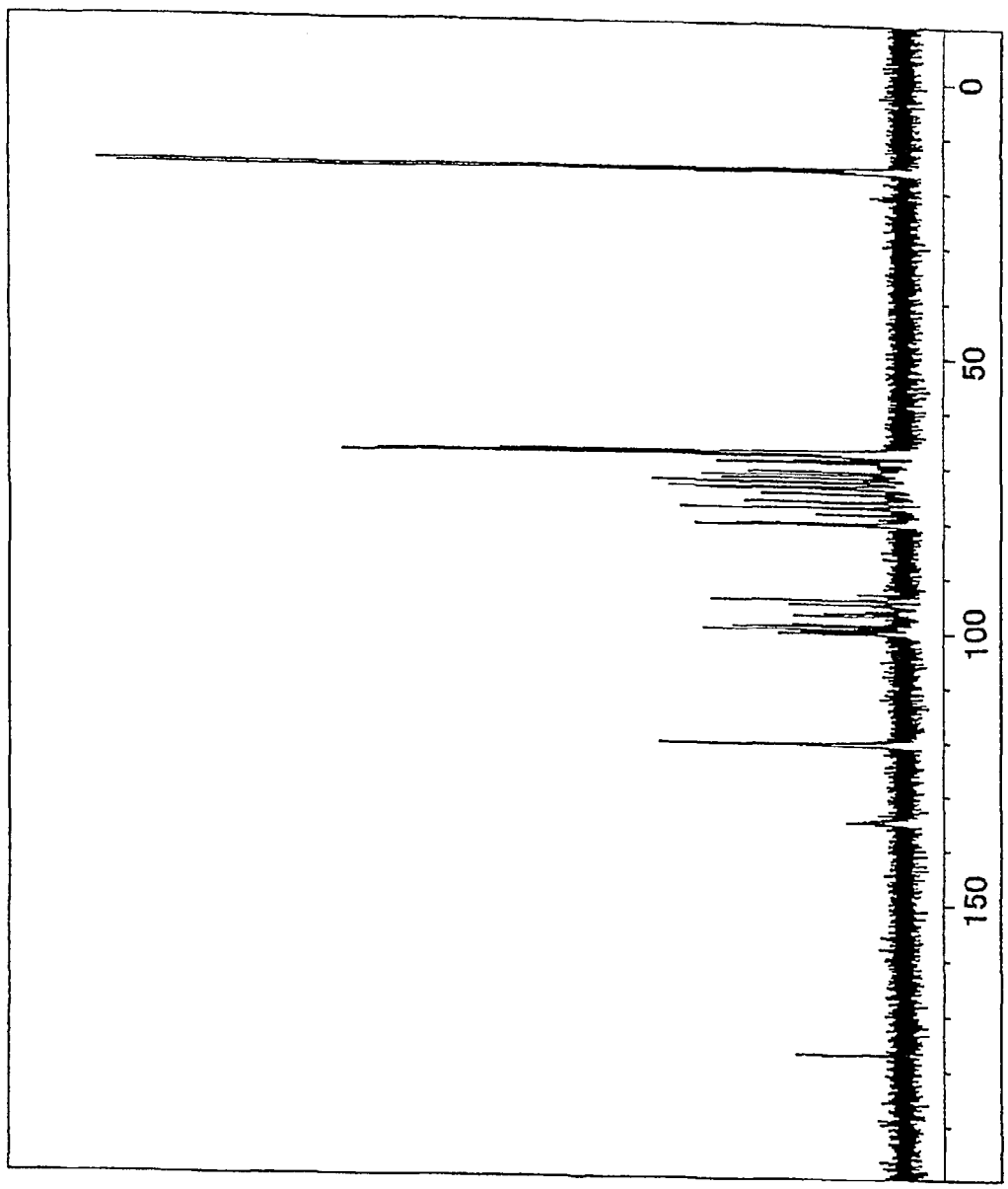
FIG. 20: a figure which illustrates the $^{13}$C-NMR spectrum of the sulfated glucuronofucan oligosaccharide 1-(7) according to the present invention.
Figure 21:
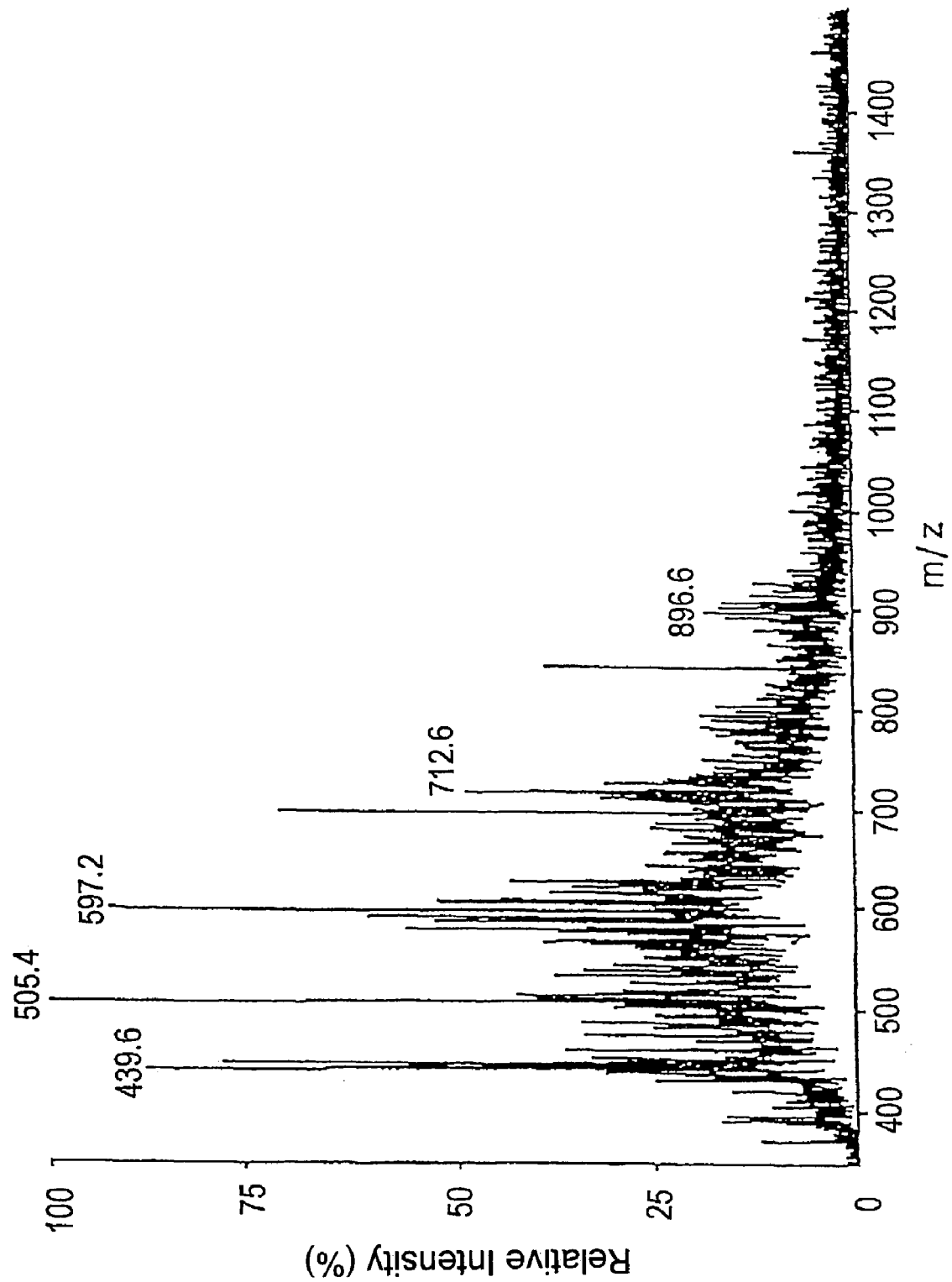
FIG. 21: a figure which illustrates the mass spectrum of the sulfated glucuronofucan oligosaccharide 1-(7) according to the present invention.

The results for mass spectrometric analysis are shown below. The $^1$H-NMR spectrum, $^{13}$C-NMR spectrum and mass spectrum of the sulfated glucuronofucan oligosaccharide 1-(7) of the present invention are illustrated in FIGS. 19, 20 and 21, respectively. In FIGS. 19 and 20, the vertical axes represent the signal intensity and the horizontal axes represent the chemical shift value (ppm). In FIG. 21, the vertical axis represents the relative intensity and the horizontal axis represents the m/z value.

Molecular weight: 3522

MS m/z 896.6 $[M+3Na^+-7H^+]^{4-}$, 712.6 $[M+2Na^+-7H^+]^{5-}$, 597.2 $[M+3Na^+-9H^+]^{6-}$, 505.4 $[M+Na^+-8H^+]^{7-}$, 439.6 $[M-8H^+]^{8-}$

Results of $^1$H-NMR and $^{13}$C-NMR analyses are shown in Table 4.

TABLE 4

| | Chemical shift value (ppm) | |
|---|---|---|
| | $^{13}$C-NMR | $^1$H-NMR Chemical shift value, multiplicity, coupling constant |
| F1-1 | 96.8 | 4.46, d, 8.0 |
| F1-2 | 70.6 | 3.43, dd, 8.0, 9.5 |

TABLE 4-continued

| | Chemical shift value (ppm) | |
|---|---|---|
| | $^{13}$C-NMR | $^1$H-NMR Chemical shift value, multiplicity, coupling constant |
| F1-3 | 78.3 | 3.57, m |
| F1-4 | 68.3 | 3.83, m |
| F1-5 | 71.2 | 3.65, q, 6.7 |
| F1-6 | 16.2 | 1.12, d, 6.7 |
| F2-1 | 96.3 | 4.98, d, 4.0 |
| F2-2 | 67.3 | 3.84, m |
| F2-3 | 77.1 | 3.96, m |
| F2-4 | 79.9 | 4.65, m |
| F2-5 | 67.1 | 4.29, q, 6.7 |
| F2-6 | 16.3 | 1.09, d, 6.7 |
| F3-1 | 99.7 | 4.98, d, 4.0 |
| F3-2 | 67.8 | 3.73, m |
| F3-3 | 77.0 | 3.88, m |
| F3-4 | 80.2 | 4.61, m |
| F3-5 | 67.1 | 4.33, q, 6.7 |
| F3-6 | 16.3 | 1.11, d, 6.7 |
| F4-1 | 99.3 | 4.94, d, 4.0 |
| F4-2 | 67.3 | 3.71, m |
| F4-3 | 74.5 | 3.84, m |
| F4-4 | 68.7 | 3.93, m |
| F4-5 | 67.8 | 4.20, q, 6.7 |
| F4-6 | 15.9 | 1.07, d, 6.7 |
| F5-1 | 94.7 | 4.99, d, 4.0 |
| F5-2 | 71.2 | 4.03, m |
| F5-3 | 73.4 | 4.18, m |
| F5-4 | 67.8 | 3.99, m |
| F5-5 | 67.1 | 4.19, q, 6.7 |
| F5-6 | 15.9 | 1.09, d, 6.7 |
| F6-1 | 94.0 | 5.07, d, 4.0 |
| F6-2 | 67.1 | 3.88, m |
| F6-3 | 76.2 | 3.98, m |
| F6-4 | 79.8 | 4.58, m |
| F6-5 | 67.4 | 4.36, q, 6.7 |
| F6-6 | 16.4 | 1.11, d, 6.7 |
| F7-1 | 98.7 | 4.98, d, 4.0 |
| F7-2 | 67.8 | 3.73, m |
| F7-3 | 76.0 | 3.90, m |
| F7-4 | 79.8 | 4.64, m |
| F7-5 | 67.1 | 4.36, q, 6.7 |
| F7-6 | 16.4 | 1.11, d, 6.7 |
| F8-1 | 99.3 | 4.94, d, 4.0 |

TABLE 4-continued

| | Chemical shift value (ppm) | |
|---|---|---|
| $^{13}$C-NMR | | $^1$H-NMR Chemical shift value, multiplicity, coupling constant |
| F8-2 | 67.3 | 3.71, m |
| F8-3 | 74.5 | 3.84, m |
| F8-4 | 68.7 | 3.93, m |
| F8-5 | 67.8 | 4.20, q, 6.7 |
| F8-6 | 15.9 | 1.07, d, 4.0 |
| F9-1 | 94.7 | 4.99, d, 4.0 |
| F9-2 | 71.2 | 4.03, m |
| F9-3 | 73.4 | 4.18, m |
| F9-4 | 67.8 | 3.99, m |
| F9-5 | 67.1 | 4.19, q, 6.7 |
| F9-6 | 15.9 | 1.09, d, 6.7 |
| F10-1 | 94.0 | 5.07, d, 4.0 |
| F10-2 | 67.1 | 3.88, m |
| F10-3 | 76.2 | 3.98, m |
| F10-4 | 79.8 | 4.58, m |
| F10-5 | 67.4 | 4.36, q, 6.7 |
| F10-6 | 16.4 | 1.11, d, 6.7 |
| F11-1 | 98.7 | 4.98, d, 4.0 |
| F11-2 | 67.8 | 3.73, m |
| F11-3 | 76.0 | 3.90, m |
| F11-4 | 79.8 | 4.64, m |
| F11-5 | 67.1 | 4.36, q, 6.7 |
| F11-6 | 16.4 | 1.11, d, 6.7 |
| F12-1 | 99.3 | 4.94, d, 4.0 |
| F12-2 | 67.3 | 3.71, m |
| F12-3 | 74.5 | 3.84, m |
| F12-4 | 68.7 | 3.93, m |
| F12-5 | 67.8 | 4.20, q, 6.7 |
| F12-6 | 15.9 | 1.07, d, 6.7 |
| F13-1 | 94.7 | 4.99, d, 4.0 |
| F13-2 | 71.2 | 4.03, m |
| F13-3 | 73.4 | 4.18, m |
| F13-4 | 67.8 | 3.99, m |
| F13-5 | 67.1 | 4.19, q, 6.7 |
| F13-6 | 15.9 | 1.09, d, 6.7 |
| F14-1 | 94.0 | 5.07, d, 4.0 |
| F14-2 | 67.1 | 3.88, m |
| F14-3 | 76.2 | 3.98, m |
| F14-4 | 79.8 | 4.58, m |
| F14-5 | 67.4 | 4.36, q, 6.7 |
| F14-6 | 16.4 | 1.11, d, 6.7 |
| F15-1 | 98.7 | 4.98, d, 4.0 |
| F15-2 | 67.8 | 3.73, m |
| F15-3 | 76.0 | 3.90, m |
| F15-4 | 79.8 | 4.64, m |
| F15-5 | 67.1 | 4.36, q, 6.7 |
| F15-6 | 16.4 | 1.11, d, 6.7 |
| F16-1 | 98.3 | 4.97, d, 4.0 |
| F16-2 | 69.1 | 3.57, m |
| F16-3 | 70.6 | 3.75, m |
| F16-4 | 72.6 | 3.66, m |
| F16-5 | 67.8 | 4.23, q, 6.7 |
| F16-6 | 15.8 | 1.06, d, 6.7 |
| GA1-1 | 100.1 | 5.15, d, 4.0 |
| GA1-2 | 71.8 | 3.47, dd, 4.0, 10.0 |
| GA1-3 | 73.6 | 3.58, t, 10.0 |
| GA1-4 | 72.4 | 3.36, t, 10.0 |
| GA1-5 | 73.2 | 3.81, d, 10.0 |
| GA1-6 | 177.0 | |
| GA2-1 | 100.1 | 5.15, d, 4.0 |
| GA2-2 | 71.8 | 3.47, dd, 4.0, 10.0 |
| GA2-3 | 73.6 | 3.58, t, 10.0 |
| GA2-4 | 72.4 | 3.36, t, 10.0 |
| GA2-5 | 73.2 | 3.81, d, 10.0 |
| GA2-6 | 177.0 | |
| GA3-1 | 100.1 | 5.15, d, 4.0 |
| GA3-2 | 71.8 | 3.47, dd, 4.0, 10.0 |
| GA3-3 | 73.6 | 3.58, t, 10.0 |
| GA3-4 | 72.4 | 3.36, t, 10.0 |
| GA3-5 | 73.2 | 3.81, d, 10.0 |
| GA3-6 | 177.0 | |

Saccharide composition: L-fucose:D-glucuronic acid=16:3

Sulfate group: 8 molecules

The numbers for peak identification in $^1$H-NMR and $^{13}$C-NMR are as indicated in formula (XII) below:

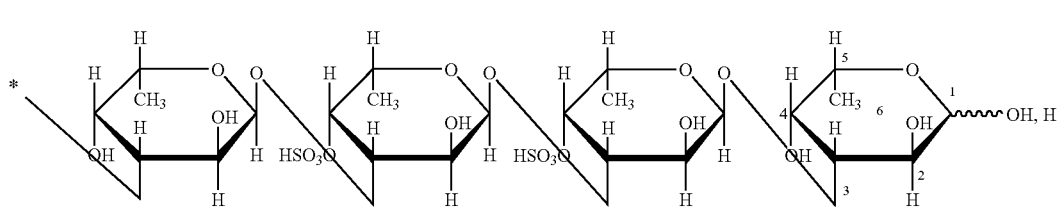

-continued

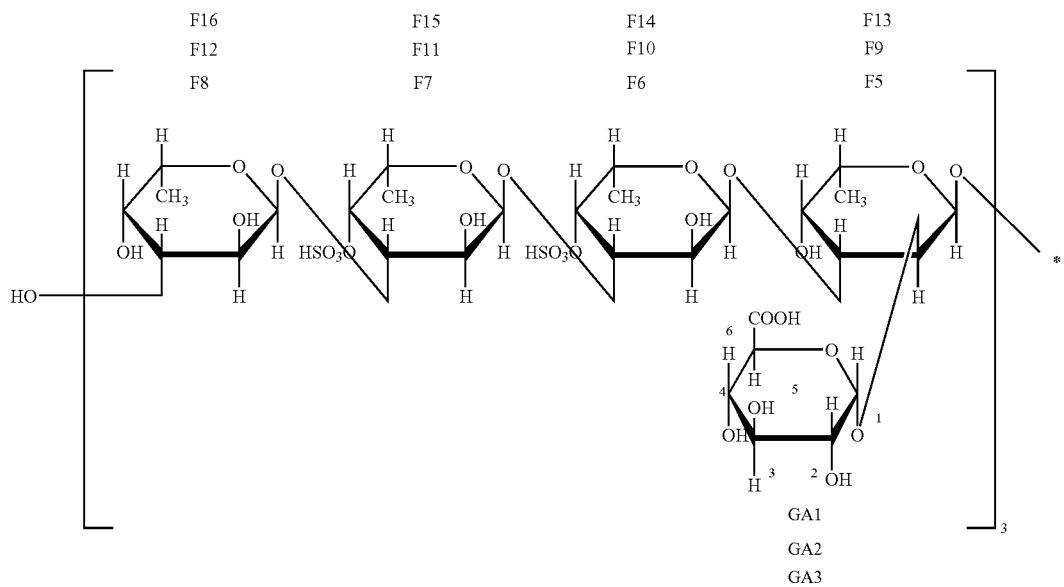

This substance is referred to as 16Fuc-8S-3GlcUA hereinafter.

(h) Physical Properties of the Oligosaccharide 1-(8)

Figure 22:
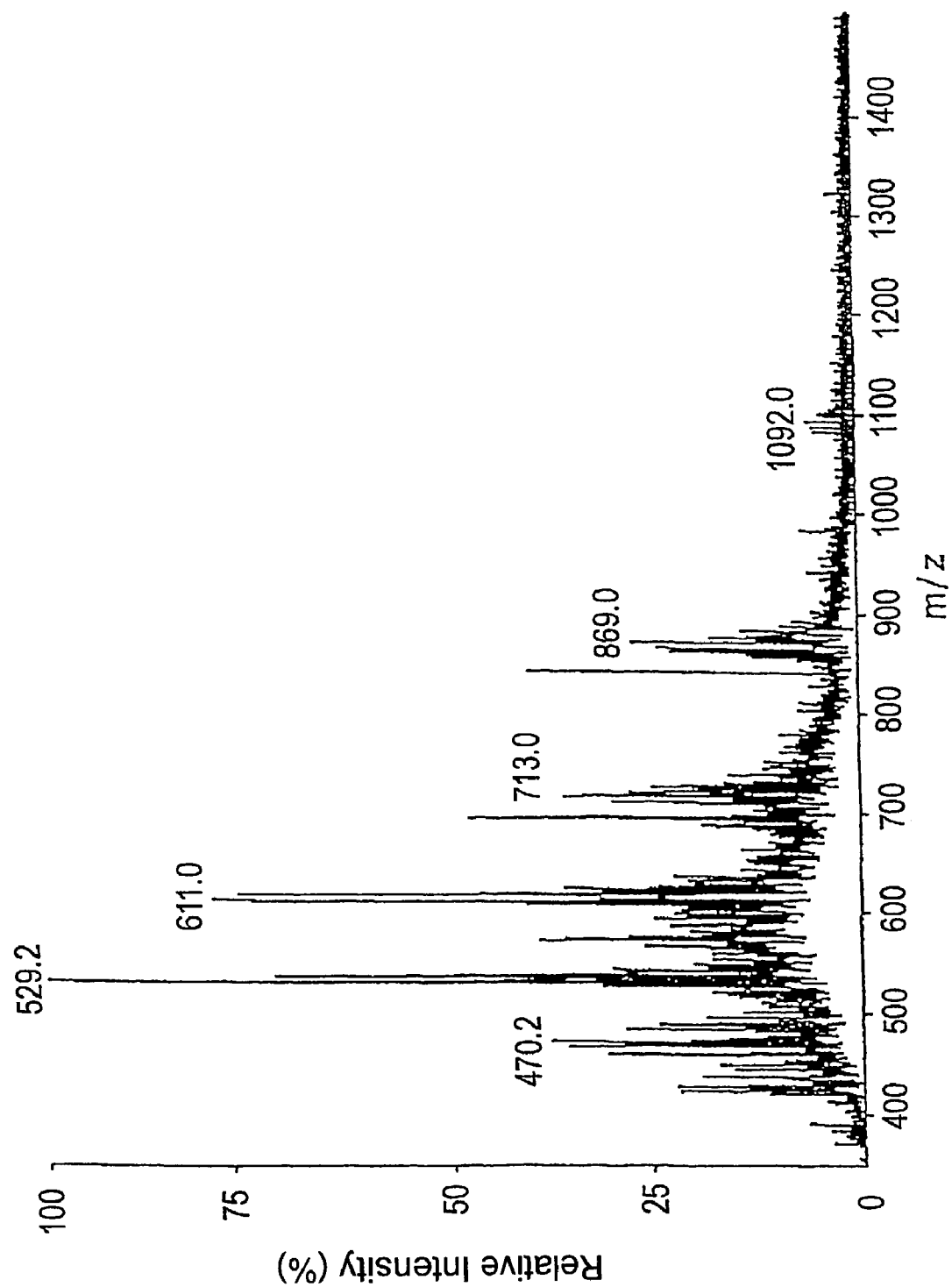
FIG. 22: a figure which illustrates the mass spectrum of the sulfated glucuronofucan oligosaccharide 1-(8) according to the present invention.

The results for mass spectrometric analysis are shown below. The mass spectrum of the sulfated glucuronofucan oligosaccharide 1-(8) of the present invention is illustrated in FIG. 22. In FIG. 22, the vertical axis represents the relative intensity and the horizontal axis represents the m/z value.

Molecular weight: 4216

MS m/z 1092.0 $[M+7Na^+-11H^+]^{4-}$, 869.0 $[M+6Na^+-11H^+]^{5-}$, 713.0 $[M+3Na^+-9H^+]^{6-}$, 611.0 $[M+3Na^+-10H^+]^{7-}$, 529.2 $[M+Na^+-9H^+]^{8-}$, 470.2 $[M+Na^+-10H^+]^{9-}$

Saccharide composition: L-fucose:D-glucuronic acid=19:4

Sulfate group: 9 molecules

Example 3

(1) The sulfated glucuronofucan oligosaccharides according to the present invention were prepared by allowing the partially purified enzyme solution as described in Example 1 to act on the crude sulfated glucuronofucan fraction as described in Referential Example 1(1). Briefly, 3 g of the crude sulfated glucuronofucan fraction was dissolved in 1 l of 10 mM imidazole-hydrochloride buffer (pH 6.6) containing 250 mM sodium chloride and 20 mM calcium chloride as well as 1 g of bovine serum albumin. 29 mU of the partially purified enzyme as described in Example 1 was then added thereto. The mixture was reacted at 30° C. for 3 days. A supernatant obtained by centrifuging the reaction mixture was subjected to an ultrafiltration device equipped with hollow fibers with exclusion molecular weight of 10,000 to collect a fraction of oligosaccharides having molecular weight of 10,000 or less. This fraction was designated as a sulfated glucuronofucan enzymatic digestion product fraction 2.

(2) The sulfated glucuronofucan enzymatic digestion product fraction 2 obtained in Example 3(1) was desalted using a desalting apparatus (Micro Acilyzer G3, Asahi Kasei). Imidazole and sodium chloride were added to the desalted sulfated glucuronofucan enzymatic digestion product fraction 2 at final concentrations of 5 mM and 10 mM, respectively. The resulting mixture was loaded onto a 1-l DEAE-Cellulofine A-800 column equilibrated with 5 mM imidazole-hydrochloride buffer (pH 7.0) containing 10 mM sodium chloride. After adequately washing with the same buffer, elution was then carried out with a gradient of 10 mM to 600 mM sodium chloride. The total sugar content and the total uronic acid content of each of the eluted fractions were measured according to the phenol-sulfuric acid method and the carbazole-sulfuric acid method, respectively. As a result, the eluted fractions formed at least five distinct peaks. The fractions in each peak were combined, concentrated to 40 ml using an evaporator, loaded onto a Cellulofine GCL-25 column equilibrated with 10% ethanol and eluted with 10% ethanol for desalting. The oligosaccharides 2-(1) to (5) were obtained as described above.

(3) Structural Analyses of Oligosaccharides

The desalted oligosaccharides 2-(1) to (5) obtained in Example 3(2) were subjected to analyses of saccharides at the reducing ends and saccharide compositions according to the fluorescence labeling method using 2-aminopyridine. As a result, the saccharide at the reducing end for each of the oligosaccharides was determined to be L-fucose. Regarding the saccharide composition, the oligosaccharide 2-(1) consisted only of fucose whereas the oligosaccharides 2-(2) to (5) consisted of fucose and glucuronic acid. Next, determination of the sulfuric acid content (measured according to the turbidimetric method using barium chloride) and the uronic acid content (measured according to the carbazole-sulfuric acid method), mass spectrometric analysis using a mass spectrometer API-III (Perkin-Elmer Sciex) and NMR analysis using a nuclear magnetic resonance apparatus JNM-α500 (Nippon Denshi) were carried out. Samples to be analyzed were subjected to structural analyses after exchange for heavy water according to a conventional method. Bonds of constituting saccharides were analyzed using the HMBC method, a method for $^1$H-detection of heteronuclei. The DQF-COSY method and the HOHAHA method were used for identification in $^1$H-NMR. The HSQC method was used for identification in $^{13}$C-NMR.

Physical properties of the oligosaccharides 2-(1) to (5) are shown below.

(a) Physical Properties of the Oligosaccharide 2-(1)

As a result of the above-mentioned analyses, it was demonstrated that this substance was identical to the oligosaccharide 1-(1).

(b) Physical Properties of the Oligosaccharide 2-(2)

As a result of the above-mentioned analyses, it was demonstrated that this substance was identical to the oligosaccharide 1-(3).

(c) Physical Properties of the Oligosaccharide 2-(3)

Figure 23:
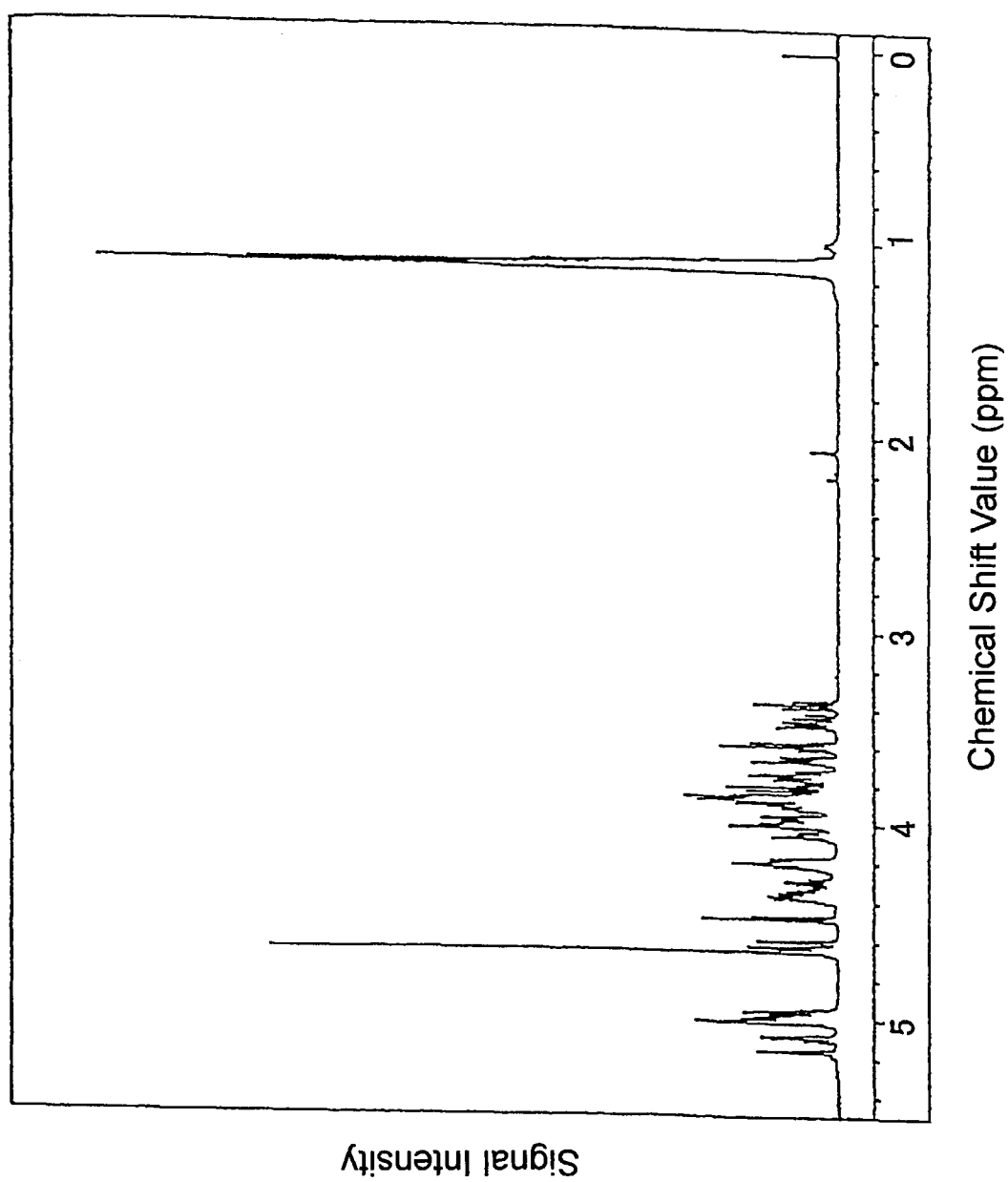
FIG. 23: a figure which illustrates the $^1$H-NMR spectrum of the sulfated glucuronofucan oligosaccharide 2-(3) according to the present invention.
Figure 24:
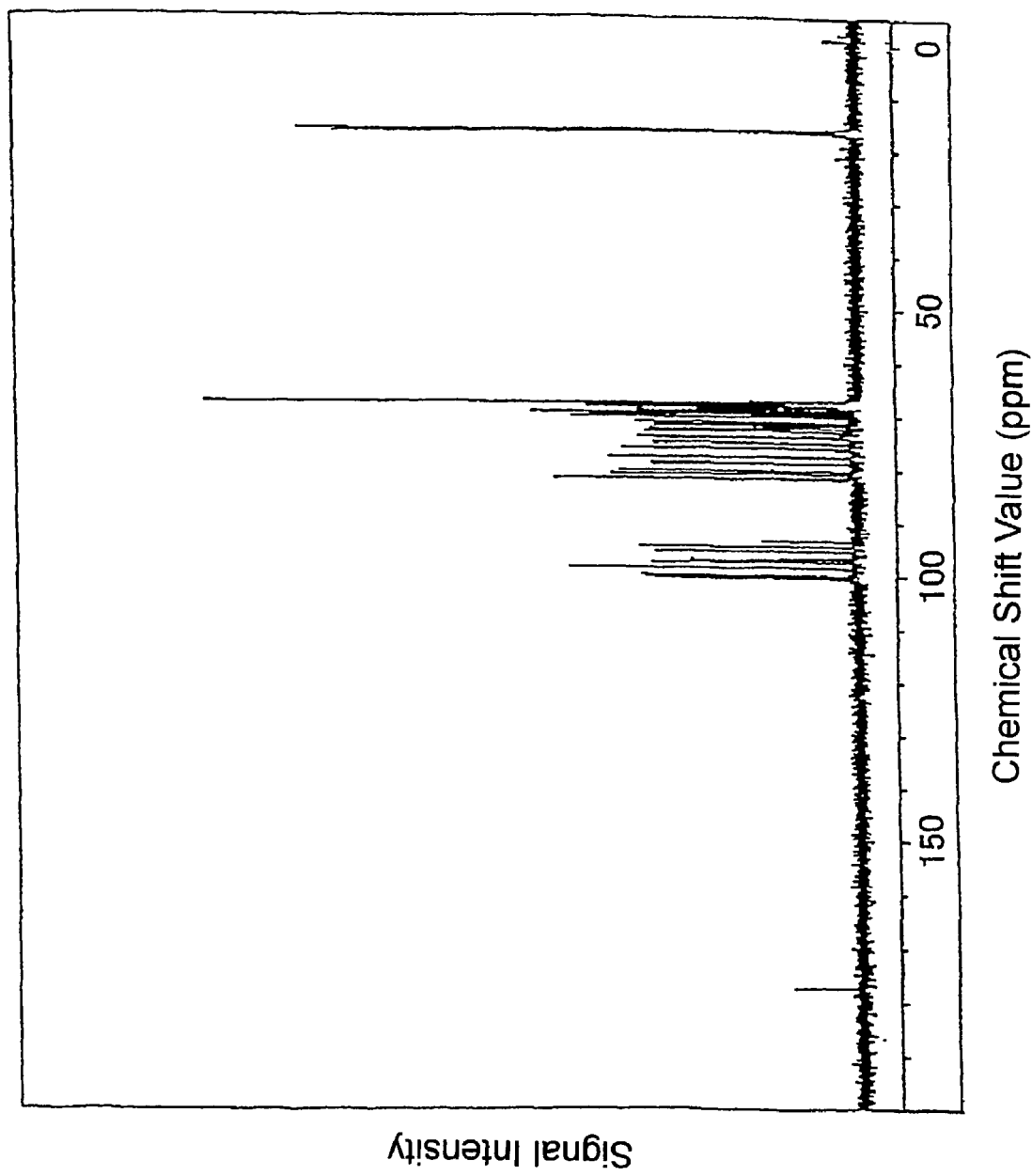
FIG. 24: a figure which illustrates the $^{13}$C-NMR spectrum of the sulfated glucuronofucan oligosaccharide 2-(3) according to the present invention.
Figure 25:
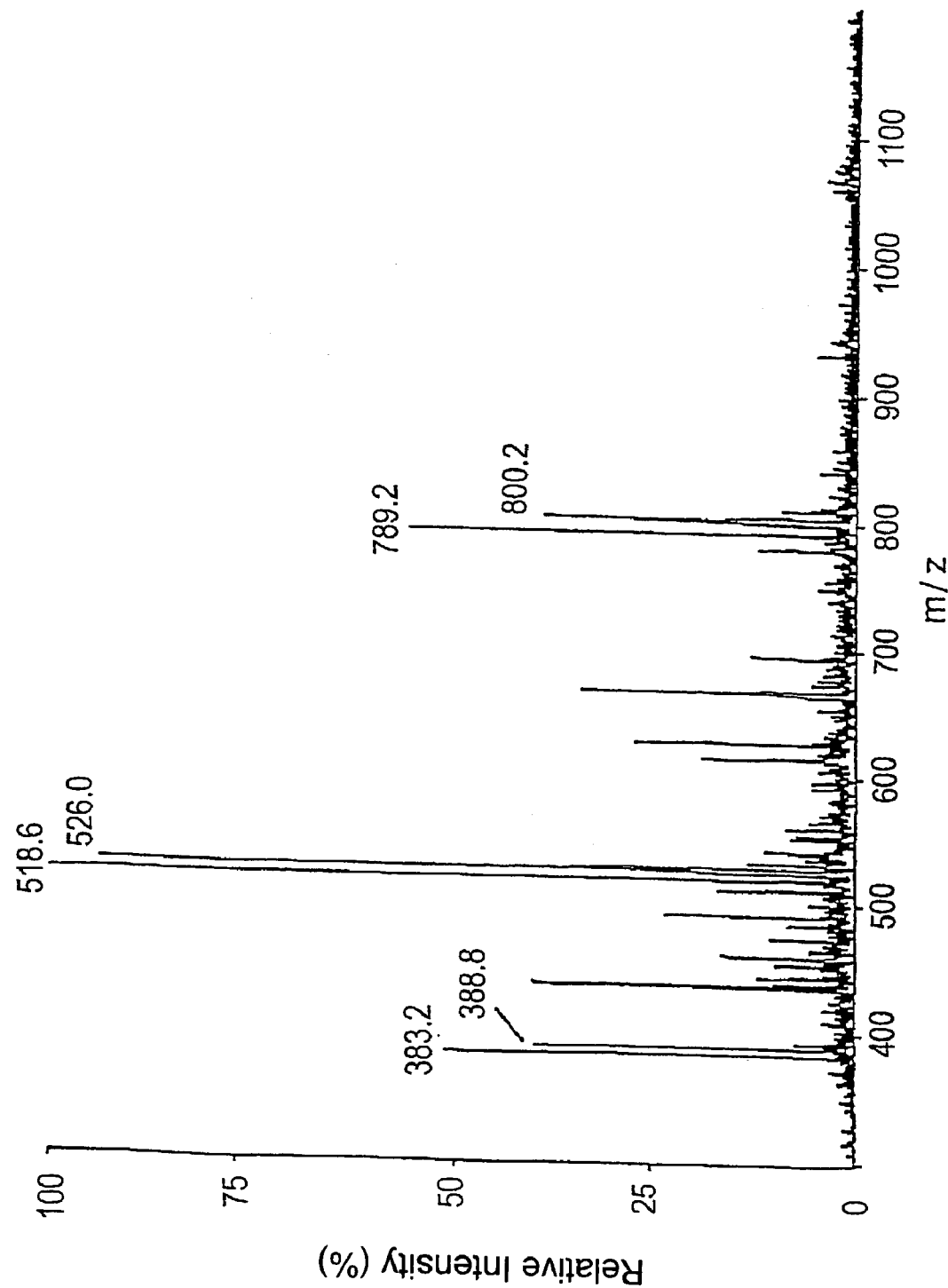
FIG. 25: a figure which illustrates the mass spectrum of the sulfated glucuronofucan oligosaccharide 2-(3) according to the present invention.

The results for mass spectrometric analysis and identification in NMR analysis are shown below. The $^1$H-NMR spectrum, $^{13}$C-NMR spectrum and mass spectrum of the sulfated glucuronofucan oligosaccharide 2-(3) of the present invention are illustrated in FIGS. 23, 24 and 25, respectively. In FIGS. 23 and 24, the vertical axes represent the signal intensity and the horizontal axes represent the chemical shift value (ppm). In FIG. 25, the vertical axis represents the relative intensity and the horizontal axis represents the m/z value.

Molecular weight: 1536

MS m/z 800.2 $[M+3Na^+-5H^+]^{2-}$, 789.2 $[M+2Na^+-4H^+]^{2-}$, 526.0 $[M+2Na^+-5H^+]^{3-}$, 518.6 $[M+Na^+-4H^+]^{3-}$, 388.8 $[M+Na^+-5H^+]^{4-}$, 383.2 $[M-4H^+]^{4-}$

Results of $^1$H-NMR and $^{13}$C-NMR analyses are shown in Table 5.

TABLE 5

| | Chemical shift value (ppm) | |
|---|---|---|
| | | $^1$H-NMR |
| | $^{13}$C-NMR | Chemical shift value, multiplicity, coupling constant |
| F1-1 | 97.1 | 4.47, d, 7.9 |
| F1-2 | 70.9 | 3.44, d-d, 7.9, 9.8 |
| F1-3 | 78.6 | 3.58, d-d, 2.8, 9.8 |
| F1-4 | 68.7 | 3.85, d, 2.8 |
| F1-5 | 71.5 | 3.66, q, 6.8 |

TABLE 5-continued

| | Chemical shift value (ppm) | |
|---|---|---|
| | | $^1$H-NMR |
| | $^{13}$C-NMR | Chemical shift value, multiplicity, coupling constant |
| F1-6 | 16.6 | 1.13, d, 6.8 |
| F2-1 | 96.6 | 4.99, d, 4.0 |
| F2-2 | 67.7 | 3.85, d-d, 4.0, 8.6 |
| F2-3 | 77.6 | 3.98, d-d, 3.1, 8.6 |
| F2-4 | 80.6 | 4.65, d, 3.1 |
| F2-5 | 67.3 | 4.30, q, 6.8 |
| F2-6 | 16.6 | 1.13, d, 6.8 |
| F3-1 | 100.1 | 4.99, d, 4.0 |
| F3-2 | 68.2 | 3.75, d-d, 4.0, 11.3 |
| F3-3 | 77.4 | 3.90, d-d, 2.7, 11.3 |
| F3-4 | 80.6 | 4.62, d, 2.7 |
| F3-5 | 67.4 | 4.34, q, 6.8 |
| F3-6 | 16.7 | 1.12, d, 6.8 |
| F4-1 | 99.6 | 4.96, d, 4.0 |
| F4-2 | 67.8 | 3.73, d-d, 4.0, 10.4 |
| F4-3 | 74.9 | 3.86, d-d, 3.1, 10.4 |
| F4-4 | 69.1 | 3.95, d, 3.1 |
| F4-5 | 68.1 | 4.21, q, 6.8 |
| F4-6 | 16.2 | 1.09, d, 6.8 |
| F5-1 | 95.1 | 5.01, d, 4.0 |
| F5-2 | 71.4 | 4.05, d-d, 4.0, 10.4 |
| F5-3 | 73.7 | 4.18, d-d, 3.1, 10.4 |
| F5-4 | 68.1 | 4.00, d, 3.1 |
| F5-5 | 67.3 | 4.19, q, 6.4 |
| F5-6 | 16.2 | 1.13, d, 6.4 |
| F6-1 | 94.2 | 5.08, d, 4.0 |
| F6-2 | 67.6 | 3.85, m |
| F6-3 | 75.8 | 4.00, m |
| F6-4 | 80.0 | 4.59, d, 2.4 |
| F6-5 | 67.4 | 4.37, q, 6.8 |
| F6-6 | 16.8 | 1.14, d, 6.8 |
| F7-1 | 98.3 | 5.01, d, 4.0 |
| F7-2 | 69.5 | 3.66, d-d, 4.0, 10.7 |
| F7-3 | 70.0 | 3.87, d-d, 2.5, 10.7 |
| F7-4 | 81.6 | 4.48, d, 2.5 |
| F7-5 | 67.4 | 4.37, q, 6.8 |
| F7-6 | 16.8 | 1.11, d, 6.8 |
| GA1-1 | 100.3 | 5.16, d, 4.0 |
| GA1-2 | 72.1 | 3.47, d-d, 4.0, 9.8 |
| GA1-3 | 74.0 | 3.59, t, 9.8 |
| GA1-4 | 72.7 | 3.37, d-d, 9.8, 10.4 |
| GA1-5 | 73.6 | 3.81, d, 10.4 |
| GA1-6 | 177.3 | — |

Saccharide composition: L-fucose:D-glucuronic acid=7:1

Sulfate group: 4 molecules

The numbers for peak identification in $^1$H-NMR and $^{13}$C-NMR are as indicated in formula (VI) below:

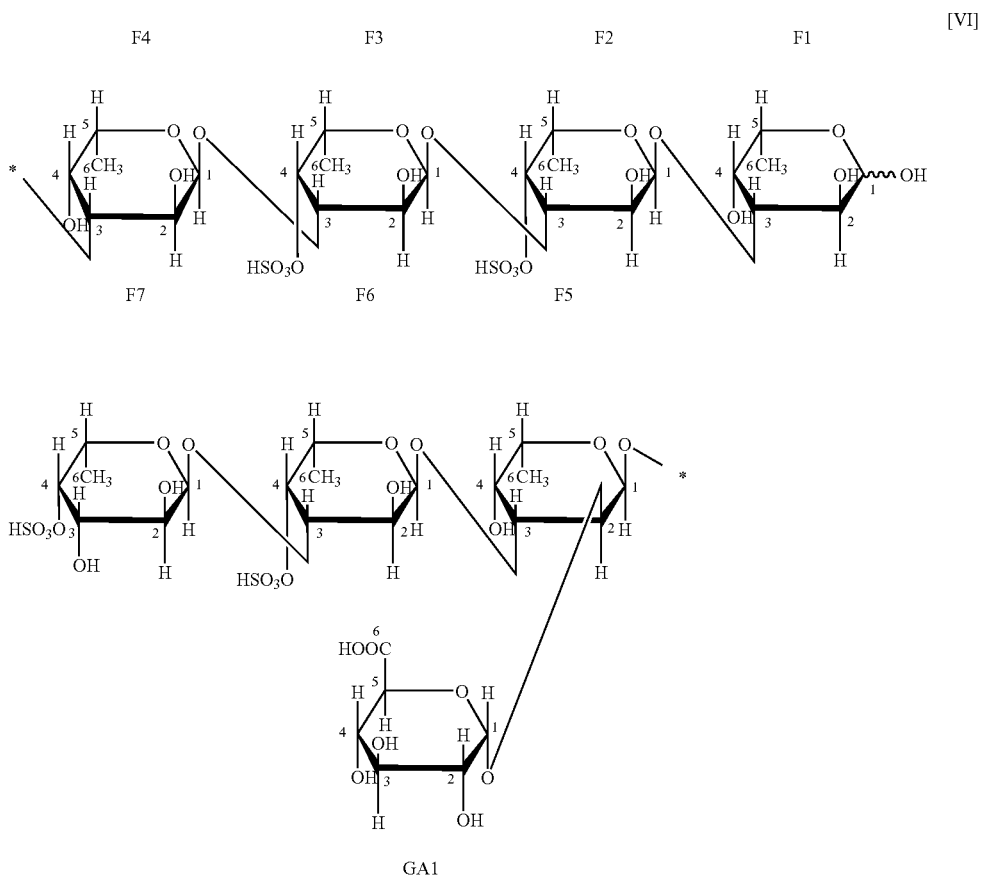

(d) Physical Properties of the Oligosaccharide 2-(4)

As a result of the above-mentioned analyses, it was demonstrated that this substance was identical to the oligosaccharide 1-(5).

(e) Physical Properties of the Oligosaccharide 2-(5)

Figure 26:
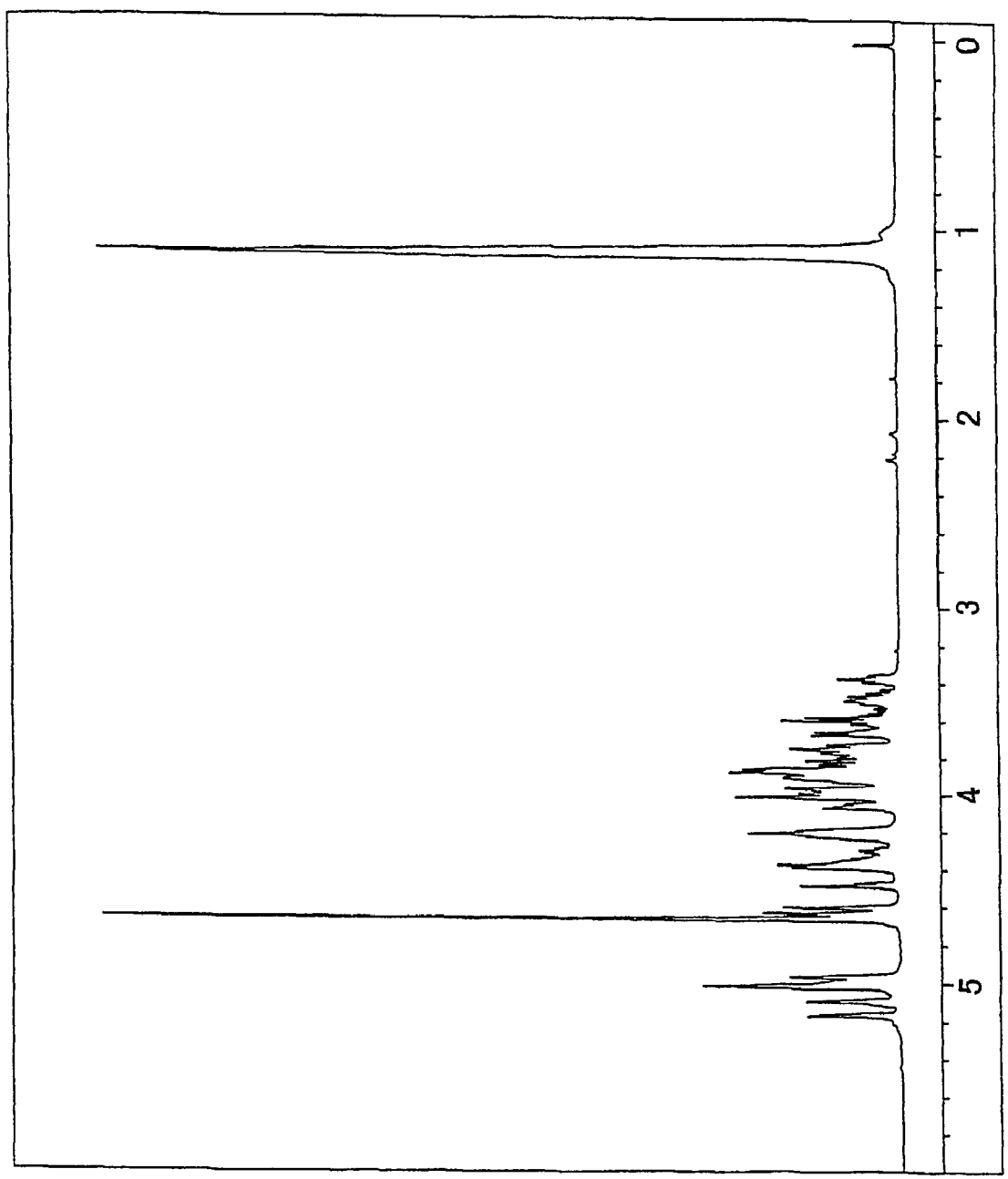
FIG. 26: a figure which illustrates the $^1$H-NMR spectrum of the sulfated glucuronofucan oligosaccharide 2-(5) according to the present invention.
Figure 27:
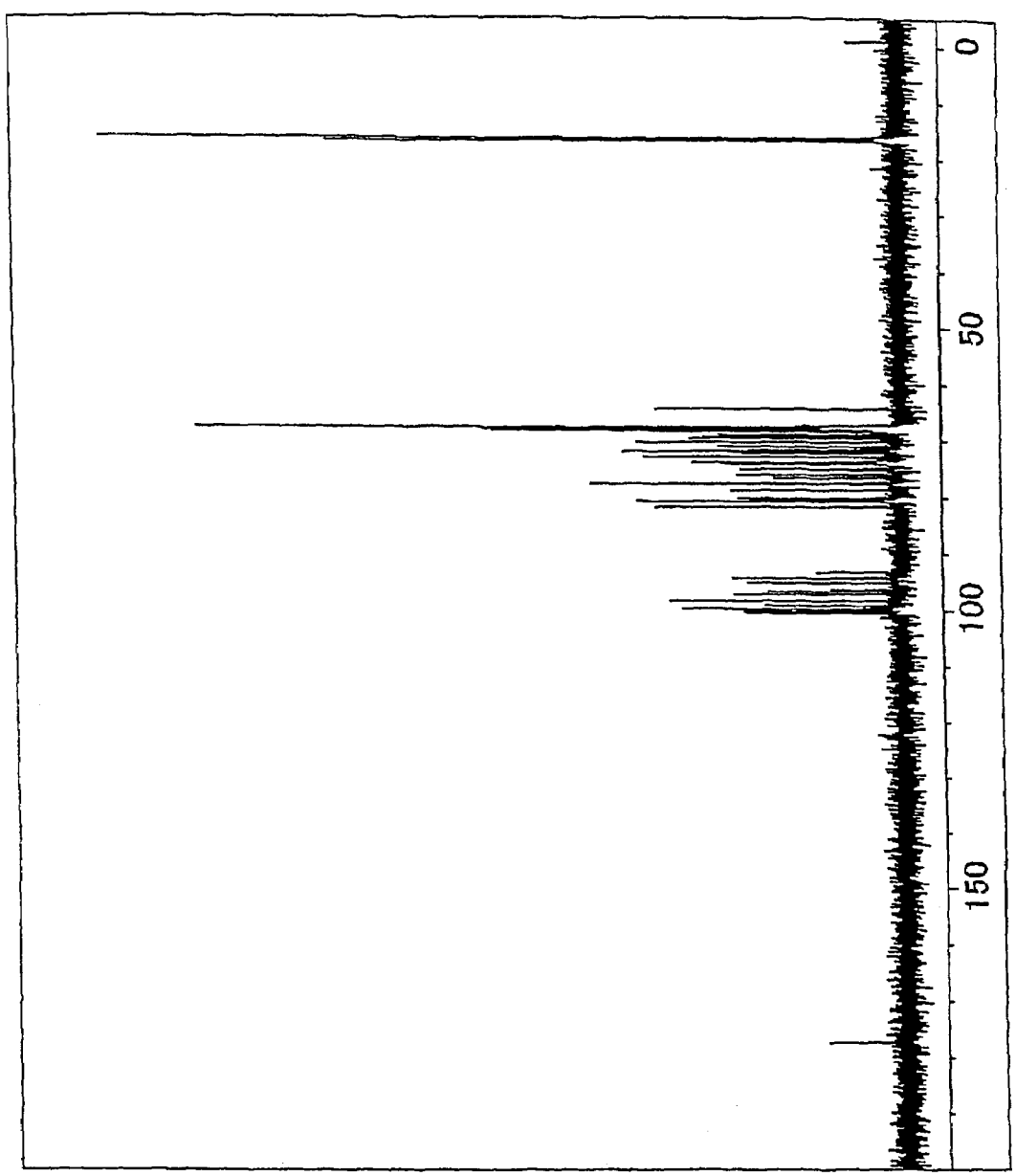
FIG. 27: a figure which illustrates the $^{13}$C-NMR spectrum of the sulfated glucuronofucan oligosaccharide 2-(5) according to the present invention.
Figure 28:
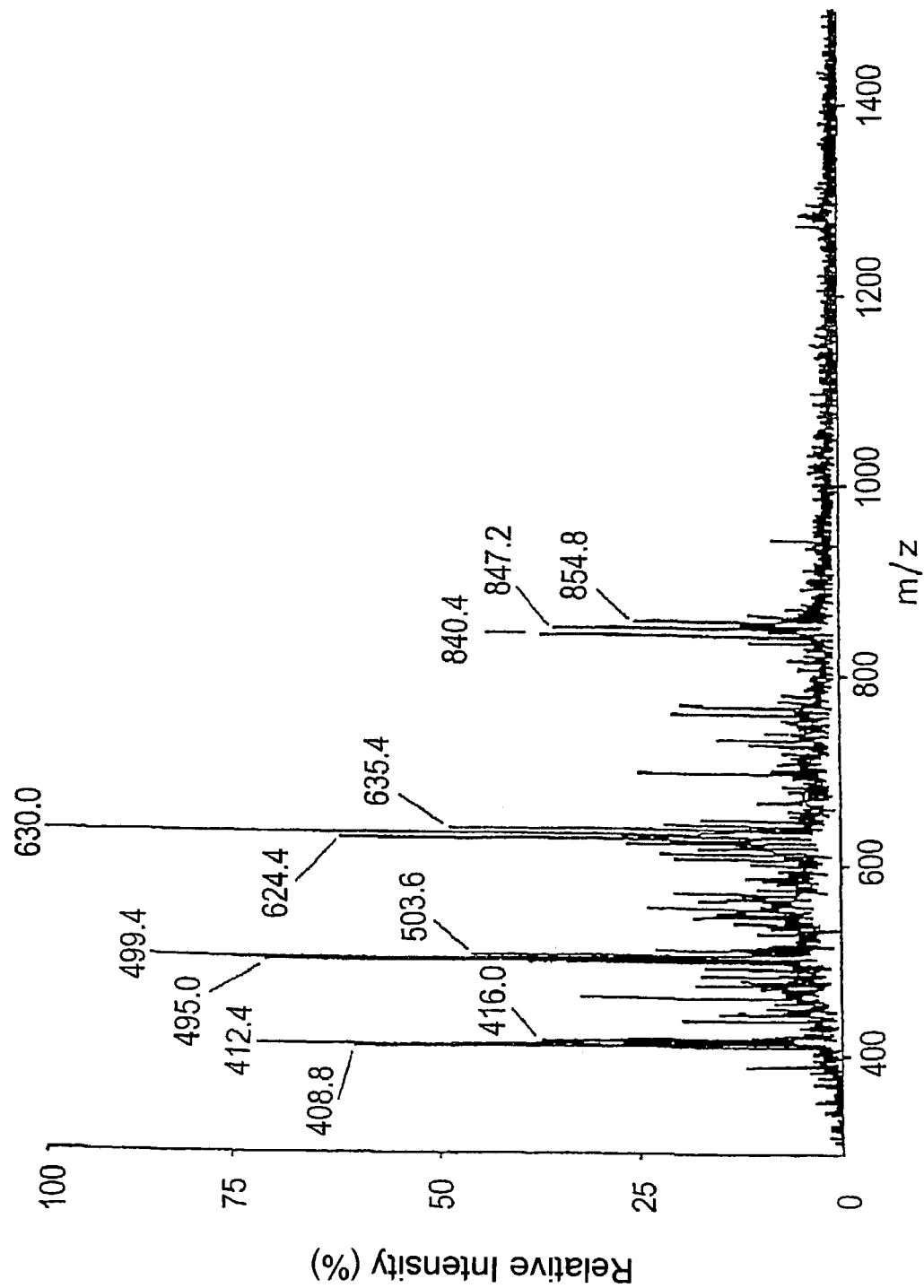
FIG. 28: a figure which illustrates the mass spectrum of the sulfated glucuronofucan, oligosaccharide 2-(5), according to the present invention.

The results for mass spectrometric analysis are shown below. The $^1$H-NMR spectrum, $^{13}$C-NMR spectrum and mass spectrum of the sulfated glucuronofucan oligosaccharide 2-(5) of the present invention are illustrated in FIGS. 26, 27 and 28, respectively. In FIGS. 26 and 27, the vertical axes represent the signal intensity and the horizontal axes represent the chemical shift value (ppm). In FIG. 28, the vertical axis represents the relative intensity and the horizontal axis represents the m/z value.

Molecular weight: 2456

MS m/z 854.8 $[M+5Na^+-8H^+]^{3-}$, 847.2 $[M+4Na^+-7H^+]^{3-}$, 840.4 $[M+3Na^+-6H^+]^{3-}$, 635.4 $[M+4Na^+-8H^+]^{4-}$, 630.0 $[M+3Na^+-7H^+]^{4-}$, 624.4 $[M+2Na^+-6H^+]^{4-}$, 503.6 $[M+3Na^+-8H^+]^{5-}$, 499.4 $[M+2Na^+-7H^+]^{5-}$, 495.0 $[M+Na^+-6H^+]^{5-}$, 416.0 $[M+2Na^+-8H^+]^{6-}$, 412.4 $[M+Na^+-7H^+]^{6-}$, 408.8 $[M-6H^+]^{6-}$

Results of $^1$H-NMR and $^{13}$C-NMR analyses are shown in Table 6.

TABLE 6

| | Chemical shift value (ppm) | |
|---|---|---|
| | $^{13}$C-NMR | $^1$H-NMR Chemical shift value, multiplicity, coupling constant |
| F1-1 | 97.1 | 4.48, d, 8.0 |
| F1-2 | 70.9 | 3.45, dd, 8.0, 9.5 |
| F1-3 | 78.6 | 3.59, m |
| F1-4 | 68.7 | 3.87, m |
| F1-5 | 71.5 | 3.67, q, 6.7 |
| F1-6 | 16.6 | 1.15, d, 6.7 |
| F2-1 | 96.6 | 4.99, d, 4.0 |
| F2-2 | 67.6 | 3.87, m |
| F2-3 | 77.5 | 3.99, m |
| F2-4 | 80.6 | 4.66, m |
| F2-5 | 67.4 | 4.30, q, 6.7 |
| F2-6 | 16.6 | 1.10, d, 6.7 |
| F3-1 | 100.1 | 5.00, d, 4.0 |
| F3-2 | 68.1 | 3.78, m |
| F3-3 | 77.5 | 3.88, m |
| F3-4 | 80.6 | 4.63, m |
| F3-5 | 67.6 | 4.35, q, 6.7 |
| F3-6 | 16.7 | 1.13, d, 6.7 |
| F4-1 | 99.6 | 4.97, d, 4.0 |
| F4-2 | 67.8 | 3.73, m |
| F4-3 | 74.8 | 3.87, m |
| F4-4 | 69.1 | 3.96, m |
| F4-5 | 68.1 | 4.22, q, 6.7 |
| F4-6 | 16.2 | 1.10, d, 6.7 |
| F5-1 | 95.1 | 5.02, d, 4.0 |
| F5-2 | 71.4 | 4.06, dd, 4.0, 10.0 |
| F5-3 | 73.7 | 4.20, m |

TABLE 6-continued

| | Chemical shift value (ppm) | |
|---|---|---|
| | $^{13}$C-NMR | $^{1}$H-NMR Chemical shift value, multiplicity, coupling constant |
| F5-4 | 68.1 | 4.01, m |
| F5-5 | 67.4 | 4.21, q, 6.7 |
| F5-6 | 16.2 | 1.12, d, 6.7 |
| F6-1 | 94.3 | 5.09, d, 4.0 |
| F6-2 | 67.4 | 3.88, m |
| F6-3 | 75.8 | 4.00, m |
| F6-4 | 80.0 | 4.60, m |
| F6-5 | 67.6 | 4.38, q, 6.7 |
| F6-6 | 16.8 | 1.13, d, 6.7 |
| F7-1 | 99.1 | 5.02, d, 4.0 |
| F7-2 | 68.2 | 3.76, m |
| F7-3 | 76.4 | 4.00, m |
| F7-4 | 80.5 | 4.66, m |
| F7-5 | 67.6 | 4.38, q, 6.7 |
| F7-6 | 16.7 | 1.13, d, 6.7 |
| F8-1 | 99.6 | 4.97, d, 4.0 |
| F8-2 | 67.8 | 3.73, m |
| F8-3 | 74.8 | 3.87, m |
| F8-4 | 69.1 | 3.96, m |
| F8-5 | 68.1 | 4.22, q, 6.7 |
| F8-6 | 16.2 | 1.10, d, 6.7 |
| F9-1 | 95.0 | 5.02, d, 4.0 |
| F9-2 | 71.4 | 4.06, dd, 4.0, 10.0 |
| F9-3 | 73.7 | 4.20, m |
| F9-4 | 68.1 | 4.01, m |
| F9-5 | 67.4 | 4.21, q, 6.7 |
| F9-6 | 16.2 | 1.12, d, 6.7 |
| F10-1 | 94.2 | 5.09, d, 4.0 |
| F10-2 | 67.4 | 3.88, m |
| F10-3 | 75.8 | 4.00, m |

TABLE 6-continued

| | Chemical shift value (ppm) | |
|---|---|---|
| | $^{13}$C-NMR | $^{1}$H-NMR Chemical shift value, multiplicity, coupling constant |
| F10-4 | 80.0 | 4.60, m |
| F10-5 | 67.6 | 4.38, q, 6.7 |
| F10-6 | 16.8 | 1.13, d, 6.7 |
| F11-1 | 98.3 | 5.02, d, 4.0 |
| F11-2 | 69.5 | 3.67, m |
| F11-3 | 70.0 | 3.88, m |
| F11-4 | 81.6 | 4.49, m |
| F11-5 | 67.6 | 4.38, q, 6.7 |
| F11-6 | 16.7 | 1.12, d, 6.7 |
| GA1-1 | 100.4 | 5.17, d, 4.0 |
| GA1-2 | 72.1 | 3.49, dd, 4.0, 10.0 |
| GA1-3 | 74.0 | 3.60, t, 10.0 |
| GA1-4 | 72.7 | 3.37, t, 10.0 |
| GA1-5 | 73.6 | 3.82, d, 10.0 |
| GA1-6 | 177.3 | |
| GA2-1 | 100.3 | 5.17, d, 4.0 |
| GA2-2 | 72.1 | 3.49, dd, 4.0, 10.0 |
| GA2-3 | 74.0 | 3.60, t, 10.0 |
| GA2-4 | 72.7 | 3.37, t, 10.0 |
| GA2-5 | 73.6 | 3.82, t, 10.0 |
| GA2-6 | 177.3 | |

Saccharide composition: L-fucose:D-glucuronic acid=11:2

Sulfate group: 6 molecules

The numbers for peak identification in $^{1}$H-NMR and $^{13}$C-NMR are as indicated in formula (XIII) below:

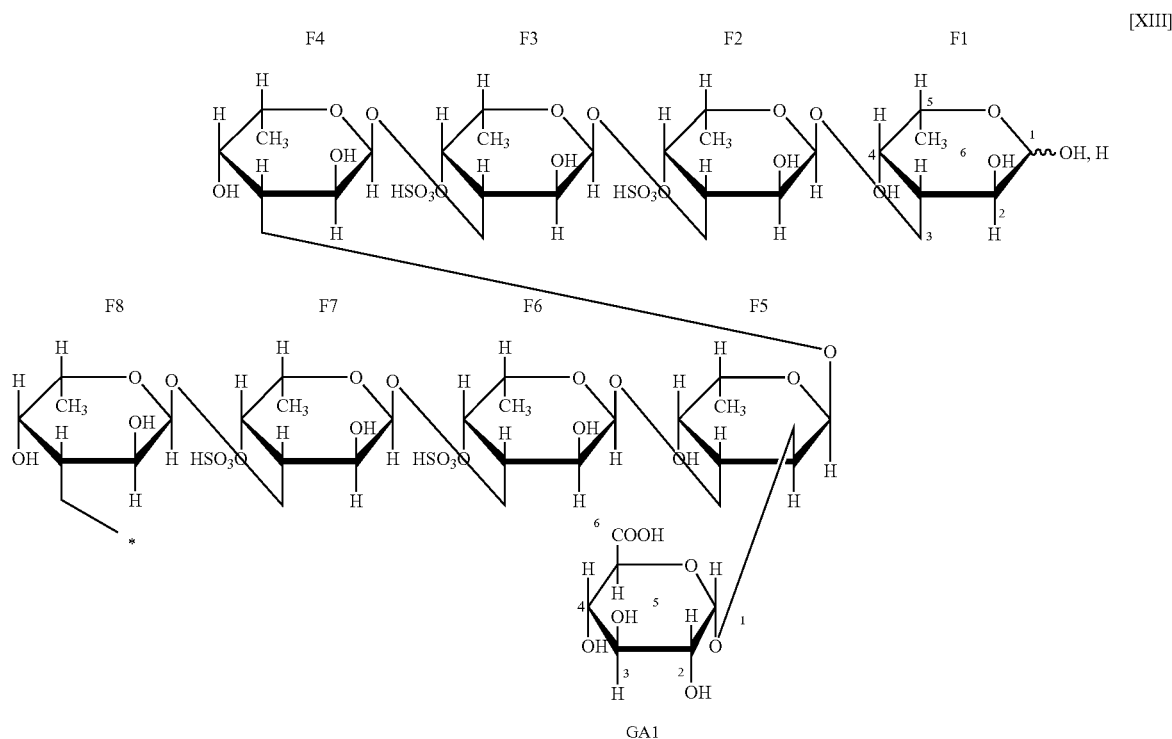

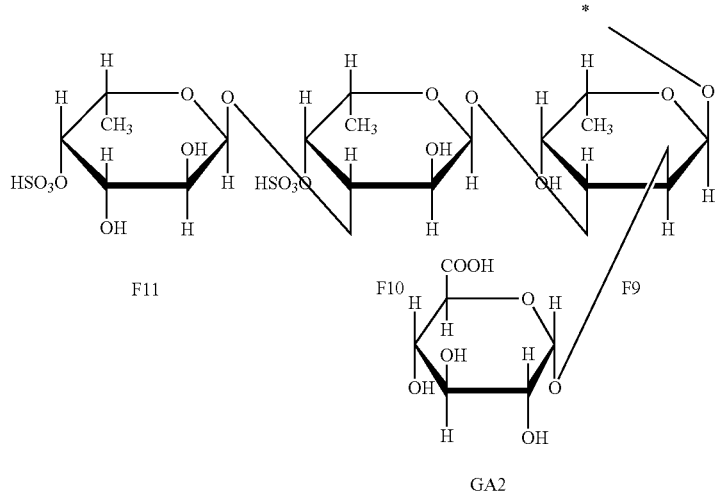

This substance is referred to as 11Fuc-6S-2GlcUA hereinafter.

For the enzymatic reaction products obtained in Examples 2 and 3 above, for example, the difference in mass between the oligosaccharides 1-(1) and 1-(3), 1-(3) and 1-(5), or 1-(5) and 1-(7) corresponds to the mass of four fucose molecules, two sulfate group molecules and one glucuronic acid molecule. The difference in mass between the oligosaccharides 1-(2) and 1-(4), 1-(4) and 1-(6), 1-(6) and 1-(8), 2-(1) and 2-(2), 2-(2) and 2-(4) or 2-(3) and 2-(5) corresponds to the same mass. Based on the above, it was considered that the crude or partially purified enzyme solution obtained in Example 1 contained an enzyme that cleaves a sulfated glucuronofucan to result in a repeating unit. Specifically, the repeating unit is a unit consisting of four fucose molecules, two sulfate group molecules and one glucuronic acid molecule, or -3F-3(4S)F1-3(4S)F1-3(GU1-2)F1-(wherein F, S and GU represent α-L-fucose, sulfate group and α-D-glucuronic acid, respectively). However, an oligosaccharide consisting of four fucose molecules, two sulfate group molecules and one glucuronic acid molecule was not found in the reaction products, while an oligosaccharide having a similar structure which consisted of four fucose molecules and two sulfate group molecules was generated. These results suggested that the partially purified enzyme solution obtained in Example 1(1) was a mixture containing at least a glucuronidase and a fucosidase.

Example 4

(1) Preparation of Sulfated Glucuronofucan-Cellulofine

In order to prepare an affinity resin for separating the enzyme(s) contained in the partially purified enzyme solution obtained in Example 1(1), the crude sulfated glucuronofucan fraction as described in Referential Example 1(1) was immobilized to Amino-Cellulofine (Seikagaku Corporation). The immobilization was carried out according to the instructions by Seikagaku Corporation. Specifically, 1.5 g of the crude sulfated glucuronofucan fraction was dissolved in 80 ml of water, the pH was adjusted to 4.5 using hydrochloric acid, 50 ml of Amino-Cellulofine and 3 g of 1-ethyl-3-(dimethylaminopropyl)-calbodiimide hydrochloride were added thereto, the mixture was stirred at 4° C. for 20 hours, filtrated and washed adequately with water, and sulfated glucuronofucan-Cellulofine was obtained.

(2) Separation of α-D-glucuronidase and endo-α-L-fucosidase using Sulfated Glucuronofucan-Cellulofine After the partially purified enzyme solution obtained in Example 1(1) was dialyzed adequately against 10 mM imidazole-hydrochloride buffer (pH 7.5) containing 50 mM sodium chloride and 10 mM calcium chloride, it was loaded onto 50-ml sulfated glucuronofucan-Cellulofine equilibrated with the same buffer. After washing with the same buffer, elution was then carried out with a gradient of 50 mM to 1 M sodium chloride. Measurement of "the activities of degrading a sulfated glucuronofucan" of the eluted fractions revealed that the recovery rate of the activity was about 2%. However, when an eluted fraction having "the activity of degrading a sulfated glucuronofucan" slightly remaining therein was mixed with a fraction not adsorbed to the sulfated glucuronofucan-Cellulofine, "the activity of degrading a sulfated glucuronofucan" of the mixture was almost equivalent to that of the sample loaded onto the column.

The above-mentioned non-adsorbed fraction could not convert the sulfated glucuronofucan into smaller molecules at all if it was used alone. The eluted fraction having a slight "activity of degrading a sulfated glucuronofucan" could not completely convert the sulfated glucuronofucan into smaller molecules if it was used alone. Then, it was shown that the non-adsorbed fraction and the eluted fraction degraded the sulfated glucuronofucan in manners different each other and that the non-adsorbed fraction could act on the sulfated glucuronofucan only after the eluted fraction had been allowed to act thereon. These results suggested that the eluted fraction cleaved the side chain of the sulfated glucuronofucan, a portion which does not result in a large change in molecular weight of the sulfated glucuronofucan (e.g., α-D-glucuronyl bond or sulfate ester bond), while the non-adsorbed fraction cleaved the main chain (i.e., α-L-fucosyl bond).

Example 5

(1) Labeling of Oligosaccharides According to Method of Fluorescence Labeling with 2-Aminopyridine (PA-labeling)

The following experiments were carried out in order to examine the action mechanisms of the non-adsorbed fraction and the eluted fraction as described in Example 4(2).

50 pmole each of the dried preparations of the sulfated glucuronofucan oligosaccharides 1-(1) to (8) and 2-(3) and 2-(5) was subjected to fluorescence labeling with 2-aminopyridine (PA-labeling) at the reducing end using Glyco-TAG and GlycoTAG Reagent Kit (both from Takara Shuzo) to prepare PA-labeled oligosaccharides.

(2) Activities of the non-adsorbed fraction and the eluted fraction as described in Example 4(2) on the ten PA-labeled oligosaccharides as described in Example 5(1) were examined using the following reaction system:

Reaction System
50 μl of 50 mM imidazole-hydrochloride buffer (pH 6.6)
23 μl of water
5 μl of 4 M sodium chloride
2 μl of 1 M calcium chloride
5 μl of 5 mg/ml bovine serum albumin
10 μl of 2 pmole/μl PA-labeled oligosaccharide
5 μl of water, or the non-adsorbed fraction or the eluted fraction as described in Example 4(2)

All of the components were mixed together, the mixture was reacted at 30° C. for 3 hours and treated at 100° C. for 10 minutes, and a supernatant obtained by centrifugation was subjected to analysis using HPLC under the following conditions to determine the activity on each PA-labeled oligosaccharide:

Instrument: L-6200 (Hitachi);
Column: OHpak SB-803 (8×300 mm; Showa Denko);
Eluent: 0.2 M sodium chloride containing 5 mM sodium azide and 10% dimethyl sulfoxide;
Detection: excitation wavelength at 320 nm and emission wavelength at 400 nm using fluorescence detector F-1150 (Hitachi);
Flow rate: 1 ml/minute; and
Column temperature: 50° C.

The presence or absence of an activity of the non-adsorbed fraction or the eluted fraction as described in Example 4(2) on each of the PA-labeled sulfated glucuronofucan oligosaccharides as well as the retention time on SB803 column for each PA-labeled oligosaccharide before or after the action, which were demonstrated as a result of the above-mentioned analyses, are shown in Table 7.

TABLE 7

| PA-labeled oligo-saccharide | Presence of activity | | Retention time of eluted fraction | |
|---|---|---|---|---|
| | Non-adsorbed fraction | Eluted fraction | Before action | After action |
| 1-(1) | − | − | 9.74 | 9.72 |
| 1-(2) | − | + | 9.09 | 9.22 |
| 1-(3) | − | + | 8.94 | 9.06 |
| 1-(4) | − | + | 8.76 | 8.91 |
| 1-(5) | − | + | 8.56 | 8.65 |
| 1-(6) | − | + | 8.50 | 8.60 |
| 1-(7) | − | + | 8.40 | 8.48 |
| 1-(8) | − | + | 8.31 | 8.40 |
| 2-(3) | − | + | 8.92 | 9.04 |
| 2-(5) | − | + | 8.56 | 8.68 |

As shown in Table 7, the non-adsorbed fraction in Example 4(2) could act on none of the PA-labeled oligosaccharides. On the other hand, the eluted fraction in Example 4(2) acted on the sulfated glucuronofucan oligosaccharides other than the sulfated glucuronofucan oligosaccharide 1-(1). These results strongly suggested that the eluted fraction in Example 4(2) contained an enzyme that cleaves glucuronic acid in a sulfated glucuronofucan oligosaccharide. For example, cleavage of one fucose molecule from the oligosaccharide 1-(3) results in generation of the oligosaccharide 2-(3). It is considered that this reaction results in change in retention time from 8.94 minutes to 8.92 minutes. A reaction of the eluted fraction of Example 4(2) to the oligosaccharide 1-(3) resulted in change in retention time from 8.94 minutes to 9.06 minutes. Accordingly, it was considered that this reaction was not a reaction in which fucose is cleaved. Similarly, it was considered that the reaction with the eluted fraction in Example 4(2) was not a reaction in which a sulfate ester is cleaved based on comparison between the oligosaccharides 2-(5) and 1-(4) or 2-(3) and 1-(2). Furthermore, it was suggested that the reaction with the eluted fraction in Example 4(2) was not a reaction in which a sulfated fucose is cleaved based on comparison between the oligosaccharides 1-(5) and 1-(4), 1-(7) and 1-(6) or 1-(3) and 1-(2).

(3) In order to confirm that the eluted fraction as described in Example 4(2) has an α-D-glucuronidase activity, the eluted fraction as described in Example 4(2) was allowed to act on the sulfated glucuronofucan oligosaccharide 1-(3) as described in Example 2, and the change in mass was analyzed. First, the following reaction system was constructed:

Reaction System
32.1 ml of 50 mM imidazole-hydrochloride buffer (pH 6.6)
2.0 ml of 4 M sodium chloride
0.8 ml of 1 M calcium chloride
4.0 ml of 5 mg/ml bovine serum albumin
10 mg of the sulfated glucuronofucan oligosaccharide 1-(3) as described in Example 2
1.0 ml of the eluted fraction as described in Example 4(2)

All of the components were mixed together, the mixture was reacted at 30° C. for 5 days, loaded onto a Cellulofine GCL-25 column (4×90 cm) equilibrated with 10% ethanol for desalting, and fractionated such that each fraction contained 9.1 ml of the eluate. The total sugar content and the total uronic acid content of each of the fractionated fractions were measured according to the phenol-sulfuric acid method and the carbazole-sulfuric acid method, respectively. As a result, a fraction strongly positive for the color development in the phenol-sulfuric acid method was negative for the color development in the carbazole-sulfuric acid method. Thus, it was strongly suggested that glucuronic acid was cleaved from the sulfated glucuronofucan oligosaccharide 1-(3) which contained glucuronic acid. Furthermore, in order to confirm that glucuronic acid was cleaved, the fraction strongly positive for the color development in the phenol-sulfuric acid method was subjected to mass spectrometric analysis. As a result, the fraction contained a substance having a mass of 1506, which is consistent with the mass of a substance which is generated by cleaving glucuronic acid from the sulfated glucuronofucan oligosaccharide 1-(3). Since a substance having a mass of 1682 corresponding to the mass of the sulfated glucuronofucan oligosaccharide 1-(3) was not detected, it was shown that the deglucuronylation reaction proceeded completely.

Based on the above-mentioned results, it was shown that the eluted fraction as described in Example 4(2) contained α-D-glucuronidase. It was considered that the substance having a mass of 1506 consistent with that of a substance generated by cleaving glucuronic acid from the sulfated glucuronofucan oligosaccharide 1-(3) had a structure of formula (VII) below:

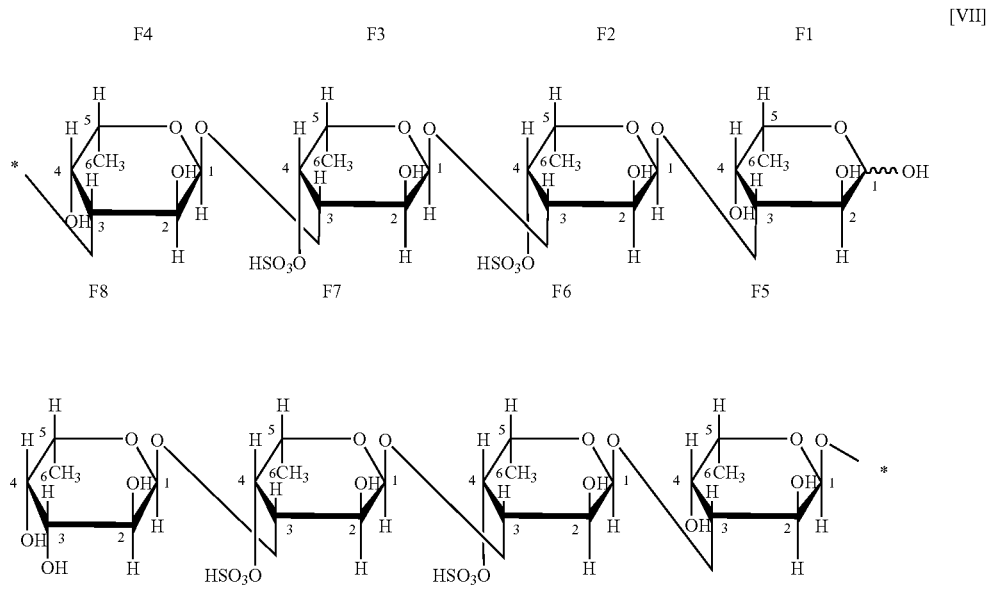

This substance is referred to as 8Fuc-4S hereinafter.

Then, optimal conditions for a reaction of the α-D-glucuronidase of the present invention on the PA-labeled sulfated glucuronofucan oligosaccharide 1-(3) obtained in Example 5(1) were examined. The activity of the α-D-glucuronidase of the present invention was determined using the following reaction system:

Reaction System

50 μl of 50 mM imidazole-hydrochloride buffer (pH 7.0) containing 100 mM sodium chloride 21 μl of water 4 μl of 1 M calcium chloride 10 μl of 3 mg/ml bovine serum albumin 10 μl of the PA-labeled sulfated glucuronofucan oligosaccharide 1-(3) obtained in Example 5(1) at a concentration 4 pmole/μl 5 μl of α-D-glucuronidase solution All of the components were mixed together, the mixture was reacted at 22° C. for 3 hours and treated at 100° C. for 10 minutes, and a supernatant obtained by centrifugation was subjected to analysis using HPLC under the following conditions:

Instrument: L-6200 (Hitachi);

Column: L-column (4.6×250 mm; Chemicals Inspection and Testing Institute);

Eluent: 50 mM acetate-triethylamine buffer (pH 5.0) containing 0.3% butanol;

Detection: excitation wavelength at 320 nm and emission wavelength at 400 nm using fluorescence detector F-1150 (Hitachi);

Flow rate: 1 ml/minute; and

Column temperature: 40° C.

One unit of the α-D-glucuronidase of the present invention is defined as an amount of the enzyme that cleaves glucuronyl bonds in 1 μmole of the PA-labeled sulfated glucuronofucan oligosaccharide 1-(3) obtained in Example 5(1) in 1 minute in the above-mentioned reaction system. The amount of cleaved glucuronyl bond was calculated according to the following equation:

$$DGA/180 \times 0.005 = U/\text{ml} \quad \text{Equation 2}$$

DGA: amount of cleaved PA-labeled sulfated glucuronofucan oligosaccharide 1-(3) obtained in Example 5(1) (μmole);

180: reaction time (minutes); and 0.005: volume of enzyme solution (ml).

(4) Fluorescence Labeling with 2-Aminopyridine (PA-labeling) of 8Fuc-4S in Example 5(3)

50 mmole of 8Fuc-4S as described in Example 5(3) was subjected to fluorescence labeling with 2-aminopyridine (PA-labeling) at the reducing end using GlycoTAG and GlycoTAG Reagent Kit (both from Takara Shuzo) to prepare a PA-labeled oligosaccharide. This substance is referred to as 8Fuc-4S-PA hereinafter.

(5) Examination of Activities of the Non-adsorbed Fraction and the Eluted Fraction as Described in Example 4(2) using 8Fuc-4S-PA Activities of the non-adsorbed fraction and the eluted fraction as described in Example 4(2) on 8Fuc-4S-PA as described in Example 5(4) were determined using the following reaction system:

Reaction System

50 μl of 50 mM imidazole-hydrochloride buffer (pH 6.6)

23 μl of water

5 μl of 4 M sodium chloride

2 μl of 1 M calcium chloride

5 μl of 5 mg/ml bovine serum albumin

10 μl of 2 pmole/μl 8Fuc-4S-PA

5 μl of water, or the non-adsorbed fraction or the eluted fraction as described in Example 4(2).

All of the components were mixed together, the mixture was reacted at 30° C. for 3 hours and treated at 100° C. for 10 minutes, and a supernatant obtained by centrifugation was subjected to analysis using HPLC under the conditions as described in Example 5(3).

As a result, the non-adsorbed fraction as described in Example 4(2) degraded 8Fuc-4S-PA whereas the eluted fraction as described in Example 4(2) did not degrade 8Fus-4S-PA. The product obtained by degrading 8Fuc-4S-PA using the non-adsorbed fraction as described in Example 4(2) was eluted at the same position as that of the PA-labeled sulfated glucuronofucan oligosaccharide 1-(1) obtained in Example 5(1). These results are consistent with the fact that a large amount of a substance identical to the sulfated glucuronofucan oligosaccharide 1-(1) was obtained in Examples 2 and 3. Accordingly, it was shown that the non-adsorbed fraction as described in Example 4(2) contained an endo-α-L-fucosidase which acts on a deacetylated deglucuronylated sulfated glucuronofucan, a sulfated glucuronofucan oligosaccharide and the like.

Based on the above-mentioned results, it was shown that the sulfated glucuronofucan-Cellulofine prepared in Example 4 is a resin useful for separating the α-D-glucuronidase and the endo-α-L-fucosidase of the present invention. (6) Optimal conditions for a reaction of the endo-α-L-fucosidase of the present invention on 8Fuc-4S-PA were examined. The activity of the endo-α-L-fucosidase of the present invention was determined by measuring the activity using the following reaction system:

Reaction System

50 μl of 50 mM acetate buffer (pH 5.5) containing 40 mM sodium chloride
23 μl of water
2 μl of 1 M calcium chloride
10 μl of 3 mg/ml bovine serum albumin
10 μl of 4 pmole/μl 8Fuc-4S-PA
5 μl of endo-α-L-fucosidase solution The reaction was carried out at 30° C. for 3 hours and the reaction mixture was analyzed as described above.

One unit of the endo-α-L-fucosidase of the present invention is defined as an amount of the enzyme that cleaves fucosyl bonds in 1 mmol of 8Fuc-4S-PA in 1 minute in an endo-type manner in the above-mentioned reaction system. The amount of cleaved fucosyl bond was calculated according to the following equation:

$$DPA/180 \times 0.005 = U/ml \qquad \text{Equation 3}$$

DGA: amount of cleaved 8Fuc-4S-PA (μmole);
180: reaction time (minutes); and
0.005: volume of enzyme solution (ml).

Example 6

The non-adsorbed fraction or the eluted fraction as described in Example 4(2) was subjected to gel filtration using a Sephacryl S-200 column (4.4×100 cm) equilibrated with 10 mM imidazole-hydrochloride buffer (pH 7.5) containing 100 mM sodium chloride, 10 mM calcium chloride and 5 mM sodium azide, and fractionated such that each fraction contained 13.5 ml of the eluate. For the non-adsorbed fraction as described in Example 4(2), the α-D-glucuronidase activities of eluted fractions were determined as described in Example 5(2) using the PA-labeled sulfated glucuronofucan oligosaccharide 1-(3) as a substrate. For the eluted fraction as described in Example 4(2), the endo-α-L-fucosidase activities of eluted fractions were determined as described in Example 5(5). The molecular weight of the α-D-glucuronidase of the present invention as determined by gel filtration was about 120,000 to 180,000. The molecular weight of the endo-α-L-fucosidase of the present invention was determined to be about 150,000 to 200,000.

Example 7

The crude sulfated glucuronofucan fraction as described in Referential Example 1(1) was purified using DEAE-Cellulofine A-800. Briefly, 5 g of the crude sulfated glucuronofucan fraction as described in Referential Example 1(1) dissolved in 20 mM imidazole-hydrochloride buffer (pH 8.0) containing 50 mM sodium chloride and 10% ethanol was loaded onto a 5-l DEAE-Cellulofine A-800 column equilibrated with the same buffer. After washing with the same buffer followed by 20 mM imidazole-hydrochloride buffer (pH 8.0) containing 100 mM sodium chloride and 10% ethanol, elution was then carried out with a gradient of 100 mM to 2 M sodium chloride such that each fraction contained 500 ml of the eluate. The total sugar content was measured according to the phenol-sulfuric acid method. Fractions eluted using an elution salt concentration of about 500 mM which were considered to contain the main component of the sulfated glucuronofucan were collected, desalted using an ultrafiltration device equipped with hollow fibers with exclusion molecular weight of 100,000 and lyophilized to obtain 0.9 g of a purified sulfated glucuronofucan fraction. Adjustment of the glucuronic acid content of the purified sulfated glucuronofucan fraction was examined. First, the following reaction system was constructed:

Reaction System 5 ml of 50 mM imidazole-hydrochloride buffer (pH 6.6)
0.5 ml of 4 M sodium chloride
0.5 ml of 1 M calcium chloride
0.25 ml of 5 mg/ml bovine serum albumin
3.35 ml of the eluted fraction as described in Example 4(2)
2.4 ml of 1.25% aqueous solution of the purified sulfated glucuronofucan fraction All of the components were mixed together, and the mixture was reacted at 25° C. and sampled over time. The samples were adequately dialyzed to remove cleaved glucuronic acid. The fucose content, the glucuronic acid content and the ratio thereof for each dialyzed sample are shown in Table 8.

TABLE 8

| Reaction time (hour) | Fucose content (mM) | Glucuronic acid content (mM) | Molar ratio of fucose:glucuronic acid |
|---|---|---|---|
| 0 | 6.1 | 1.4 | 4.4:1 |
| 1 | 6.3 | 1.3 | 4.9:1 |
| 2 | 6.9 | 1.2 | 5.8:1 |
| 5 | 6.5 | 0.90 | 7.2:1 |
| 10 | 6.9 | 0.70 | 9.9:1 |
| 20 | 6.3 | 0.65 | 9.7:1 |

These results show that the ratio of fucose to glucuronic acid can be adjusted by cleaving and removing glucuronic acid from a sulfated glucuronofucan using the eluted fraction as described in Example 4(2).

Example 8

(1) Effect of Calcium Salt Concentration on Enzymatic Reaction

Reduction of the "activity of degrading a sulfated glucuronofucan" according to the present invention was observed when the concentration of calcium chloride contained in the reaction system was decreased upon measurement of the activity. Then, the relationship between the relative activity of the α-D-glucuronidase or the endo-α-L-fucosidase of the present invention and the concentration of calcium chloride contained in the reaction system was examined. As a result, it was shown that both enzymes were activated by calcium chloride. Furthermore, similar activation was observed using calcium acetate.

(2) Effect of Protein on Enzymatic Reaction

Reduction of the "activity of degrading a sulfated glucuronofucan" according to the present invention was observed when bovine serum albumin was eliminated from the reaction system upon measurement of the activity. Then, the relationship between the relative activity of the α-D-glucuronidase or the endo-α-L-fucosidase of the present invention and the concentration of bovine serum albumin contained in the reaction system was examined. As a result, it was shown that both enzymes were activated by bovine serum albumin. Furthermore, similar activation was observed using proteins produced by *Fucophilus fucoidanolyticus* strain SI-1234 of the present invention.

(3) Effect of Sodium Chloride on Enzymatic Reaction

Reduction of the "activity of degrading a sulfated glucuronofucan" according to the present invention was observed when sodium chloride was eliminated from the reaction system upon measurement of the activity. Then, the relationship between the relative activity of the α-D-glucuronidase or the endo-α-L-fucosidase of the present invention and the concentration of sodium chloride contained in the reaction system was examined. As a result, it was shown that both enzymes were not activated by sodium chloride when an oligosaccharide having a low molecular weight was used as a substrate. Based on these results, it was confirmed that sodium chloride activates each of the enzymes when a sulfated glucuronofucan having a high molecular weight is used as a substrate for the enzyme.

Example 9

*Fucophilus fucoidanolyticus* strain SI-1234 was inoculated into 600 ml of a medium consisting of artificial seawater (pH 8.0) (Jamarine Laboratory) containing the crude sulfated glucuronofucan fraction derived from *Cladosiphon okamuranus* Tokida prepared as described in Referential Example 1(1) and peptone at concentrations of 0.2% and 1%, respectively, which had been autoclaved at 120° C. for 20 minutes, and cultured at 24° C. for 72 hours to prepare a seed culture. 18 l of a medium consisting of artificial seawater (pH 8.0) (Jamarine Laboratory) containing 200 g of peptone and antifoaming agent (KM70, Shin-Etsu Chemical) was autoclaved at 120° C. for 20 minutes in a 30-l jar fermentor. 40 g of the crude sulfated glucuronofucan fraction prepared from *Cladosiphon okamuranus* Tokida as described in Referential Example 1(1) was dissolved in 2 l of artificial seawater, and treated at 95° C. for 1 hour. The seed culture was inoculated into a mixture of the medium and the solution and cultured at 125 rpm at 24° C. for 72 hours. The pH of the medium during cultivation was automatically adjusted to 7 or above. After cultivation, the culture was centrifuged to separate cells from a culture supernatant.

It was confirmed that, when the sulfated glucuronofucan to be added to the main culture medium was heated at a temperature of about 95° C. as described above, a higher rate of utilization of the sulfated glucuronofucan by *Fucophilus fucoidanolyticus* strain SI-1234 was achieved and larger amounts of the fucoidan deacetylase, the α-D-glucuronidase and the endo-α-L-fucosidase of the present invention were produced in a unit medium volume than those observed when the sulfated glucuronofucan was heat-sterilized at about 120° C.

The cells obtained by culturing as described above were suspended in 1 l of 10 mM imidazole-hydrochloride buffer (pH 7.0) containing 100 mM sodium chloride and 10 mM calcium chloride, sonicated and centrifuged to obtain an extract. The extract was adequately dialyzed against the same buffer and centrifuged to obtain a supernatant containing the fucoidan deacetylase, the α-D-glucuronidase and the endo-α-L-fucosidase of the present invention.

The "activity of degrading a sulfated glucuronofucan", the fucoidan deacetylase activity, the α-D-glucuronidase activity and the endo-α-L-fucosidase activity contained in the thus obtained supernatant were determined as described in Referential Example 1(2), Example 14, Example 5(3) and Example 5(6), respectively. As a result, it was confirmed that 6 mU/ml of "activity of degrading a sulfated glucuronofucan", 1 mU/ml of the fucoidan deacetylase, 130 μU/ml of the α-D-glucuronidase and 6 μU/ml of the endo-α-L-fucosidase were produced in the culture.

Example 10

(1) The effect of the sulfated glucuronofucan fraction on hair growth was examined.

A 2-days old male C3H/He mouse was purchased from Japan SLC together with its mother, and used for experiments at the age of 5 days. The mouse was sacrificed by bleeding. Whiskers were collected along with hypodermal tissues using scissors and tweezers. The whiskers with associated hair follicles were isolated in a Petri dish under a microscope according to the method of Ogawa et al. (J. Invest. Dermatol., 103:306–309, 1994). 14 to 16 whiskers were collected from right and left sides of a mouse. A 20-fold strengthened solution was prepared by dissolving the crude sulfated glucuronofucan fraction derived from *Cladosiphon okamuranus* Tokida as described in Referential Example 1(1) in RPMI-1640 medium. The solution was added to a culture system at a volume ratio of 1:20. The same volume of the medium was added to a control. A tissue culture dish Falcon 3037 (Becton Dickinson Labware) was used to culture the whisker. 0.7 ml of RPMI-1640 medium supplemented with 20% FCS was placed in the central well, a sterile stainless mesh (Ikeda Rika) and lens paper (TC Case) were placed thereon, and the whisker was then cultured on the paper. The crude sulfated glucuronofucan fraction derived from *Cladosiphon okamuranus* Tokida was added to the medium beforehand. The cultivation was carried out at 35° C. in the presence of 5% $CO_2$ for 6 days. The length of the whisker of the order of 0.1 mm was measured under a microscope using calipers before start and after completion of cultivation. Measurement was carried out using 3 to 5 whiskers for each sample at a given concentration. The increase in length was expressed as mean±standard error. Student's t test was used for significant test. P value versus the control group was determined. The results are shown in Table 9.

TABLE 9

| Added sample | Conc. (mg/ml) | Number of subjects | Elongation of whisker (mean ± standard error (mm) | P value |
|---|---|---|---|---|
| C. okamuranus | 0.01 | 5 | 0.90 ± 0.25 | 0.17 |
| Control | 0 | 6 | 0.38 ± 0.23 | |

As shown in Table 9, it was confirmed that the sulfated glucuronofucan fraction derived from *Cladosiphon okamuranus* Tokida was effective in elongating mouse whiskers as compared with the control.

Example 11

(1) Preparation of Enzyme

The cell extract of *Fucophilus fucoidanolyticus* strain SI-1234 prepared as described in Example 9 was adequately dialyzed against 10 mM imidazole-hydrochloride buffer (pH 7.5) containing 100 mM sodium chloride and 10 mM calcium chloride. A supernatant as a crude enzyme solution containing the α-D-glucuronidase and the endo-α-L-fucosidase of the present invention was obtained by centrifugation. The crude enzyme solution was loaded onto a 500-ml DEAE-Cellulofine A-800 column equilibrated with the same buffer. After washing with the same buffer, elution was carried out with a gradient of 100 mM to 400 mM sodium chloride such that each fraction contained 67 ml of the eluate to collect a fraction having an activity of degrading a sulfated glucuronofucan. The fraction was concentrated using an ultrafiltration device equipped with hollow fibers with fractionation molecular weight of 10,000. The concentrate was subjected to buffer exchange for 10 mM imidazole-hydrochloride buffer (pH 7.5) containing 50 mM sodium chloride and 10 mM calcium chloride. The resulting enzyme solution was loaded onto 50 ml of the sulfated glucuronofucan-Cellulofine column as described in Example 4(1) which had been equilibrated with the same buffer. After washing with the same buffer, elution was carried out with a gradient of 50 mM to 600 mM sodium chloride such that each fraction contained 10 ml of the eluate. The activity of degrading a sulfated glucuronofucan was determined for each fraction. As a result, a slight activity was detected in the eluted fraction, whereas no activity was found in the non-adsorbed fraction. However, the activity of degrading a sulfated glucuronofucan observed for a mixture of the non-adsorbed fraction and the eluted fraction was almost equivalent to that of the sample loaded onto the column.

Non-adsorbed fractions were combined and concentrated to 100 ml using an ultrafiltration device to obtain a non-adsorbed fraction concentrate. On the other hand, activities of degrading sulfated glucuronofucan of eluted fractions were determined using the concentrated non-adsorbed fraction. An active fraction was concentrated to 200 ml using an ultrafiltration device to obtain an eluted fraction concentrate. The enzymes were further purified for preparing sulfated glucuronofucan oligosaccharides. First, a reaction system for determining the activity of each fraction was constructed.

The non-adsorbed fraction or the eluted fraction cannot act on a sulfated glucuronofucan to efficiently produce oligosaccharides if it is used alone. However, if the enzymes are used in combination, they can degrade a sulfated glucuronofucan to efficiently convert it into smaller molecules. An activity of degrading a sulfated glucuronofucan in the presence of the enzymes was numerically expressed according to the method for measuring the activity as described below.

The activity of the non-adsorbed fraction was determined as follows. Briefly, 10 µl of 1% solution of the crude sulfated glucuronofucan fraction, 53 µl of 50 mM imidazole-hydrochloride buffer (pH 6.6), 5 µl of 4 M sodium chloride, 2 µl of 1 M calcium chloride, 10 µl of 5 mg/ml bovine serum albumin, 1 µl of the eluted fraction concentrate and 19 µl of an enzyme solution from the non-adsorbed fraction whose activity was to be determined were mixed together. After reacting at 30° C. for 3 hours, the reaction mixture was treated at 100° C. for 10 minutes. After centrifugation, 90 µl of the supernatant was analyzed using HPLC to determine the degree of conversion into smaller molecules. As controls, a reaction mixture obtained by a reaction in which the buffer used for dissolving the enzyme solution from the non-adsorbed fraction was used in place of the enzyme solution and a reaction mixture obtained by a reaction in which water was used in place of the crude sulfated glucuronofucan fraction were similarly analyzed using HPLC.

One unit of an activity of degrading a sulfated glucuronofucan is defined as an amount of an enzyme that cleaves fucosyl bonds in 1 µmol of a sulfated glucuronofucan in 1 minute in the above-mentioned reaction system. The amount of cleaved fucosyl bond was calculated according to the following equation:

$$\{(10\times1000\times1/100)MG\}\times\{(MG/M)-1\}\times\{1/(180\times0.019)\}=U/ml$$

Equation 4

10×1000×1/100: crude sulfated glucuronofucan fraction added to the reaction system (µg);
MG: the average molecular weight of the sulfated glucuronofucan in the control reaction mixture;
M: the average molecular weight of the reaction product;
(MG/M)−1: the number of sites cleaved by the enzyme in one sulfated glucuronofucan molecule;
180: the reaction time (minutes); and
0.019: the volume of the enzyme solution (ml).

The HPLC was carried out as follows.
Instrument: L-6200 (Hitachi);
Column: OHpak SB-806HQ (8×300 mm; Showa Denko);
Eluent: 50 mM sodium chloride containing 5 mM sodium azide;
Detection: differential refractive index detector (Shodex R1-71, Showa Denko);
Flow rate: 1 ml/minute; and
Column temperature: 25° C.

The following procedure was carried out in order to determine the average molecular weight of the reaction product. Commercially available pullulan (STANDARD P-82, Showa Denko) of which the molecular weight was known was analyzed under the same conditions as those for the above-mentioned HPLC analysis. The relationship between the molecular weight of pullulan and retention time was expressed as a curve, which was used as a standard curve for determining the molecular weight of the reaction product.

The activity of the eluted fraction was determined as follows. Briefly, 10 µl of 1% solution of the crude sulfated glucuronofucan fraction, 53 µl of 50 mM imidazole-hydrochloride buffer (pH 6.6), 5 µl of 4 M sodium chloride, 2 µl of 1 M calcium chloride, 10 µl of 5 mg/ml bovine serum albumin, 19 µl of the non-adsorbed fraction concentrate and 1 µl of an enzyme solution from the eluted fraction whose activity was to be determined were mixed together. After reacting at 30° C. for 3 hours, the reaction mixture was treated at 100° C. for 10 minutes. After centrifugation, 90 µl of the supernatant was analyzed using HPLC to determine the degree of conversion into smaller molecules. As controls, a reaction mixture obtained by a reaction in which the buffer used for dissolving the enzyme solution from the eluted fraction was used in place of the enzyme solution and a reaction mixture obtained by a reaction in which water was used in place of the crude sulfated glucuronofucan fraction were similarly analyzed using HPLC.

One unit of an activity of degrading a sulfated glucuronofucan is defined as an amount of an enzyme that cleaves fucosyl bonds in 1 µmol of a sulfated glucuronofucan in 1 minute in the above-mentioned reaction system. The amount of cleaved fucosyl bond was calculated according to the following equation:

$$\{(10\times1000\times1/100)MG\}\times\{(MG/M)-1\}\times\{1/(180\times0.001)\}=\text{U/ml} \quad \text{Equation 5}$$

10×1000×1/100: crude sulfated glucuronofucan fraction added to the reaction system (µg);
MG: the average molecular weight of the sulfated glucuronofucan in the control reaction mixture;
M: the average molecular weight of the reaction product;
(MG/M)−1: the number of sites cleaved by the enzyme in one sulfated glucuronofucan molecule;
180: the reaction time (minutes); and
0.001: the volume of the enzyme solution (ml).

The non-adsorbed fraction concentrate was purified as follows. 4 M sodium chloride was added to the non-adsorbed fraction concentrate to adjust the sodium chloride concentration to 250 mM. The mixture was loaded onto a 30-ml Phenyl-Cellulofine column equilibrated with the same buffer. After washing with the same buffer, elution was then carried out with a gradient of 250 mM to 0 mM sodium chloride followed by 10 mM imidazole-hydrochloride buffer (pH 7.5) containing 10 mM calcium chloride and then 10 mM imidazole-hydrochloride buffer (pH 7.5) containing 10% ethanol and 10 mM calcium chloride to collect a fraction with an activity of degrading a sulfated glucuronofucan as determined according to the method as described above. Each fraction contained 10 ml of the eluate.

The thus obtained fraction having an activity of degrading a sulfated glucuronofucan was fractionated on a Sephacryl S-200 column (4.4×100 cm) using 10 mM imidazole-hydrochloride buffer (pH 7.5) containing 100 mM sodium chloride, 10 mM calcium chloride and 5 mM sodium azide as an eluent to collect fractions with activities of degrading a sulfated glucuronofucan as determined according to the method as described above as purified non-adsorbed fractions. Each fraction contained 13.5 ml of the eluate.

Furthermore, the eluted fraction concentrate was purified as follows. The eluted fraction concentrate was subjected to exchange for 10 mM imidazole-hydrochloride buffer (pH 7.5) containing 100 mM sodium chloride and 10 mM calcium chloride using an ultrafiltration device equipped with hollow fibers with fractionation molecular weight of 10,000. The resulting solution was loaded onto 45-ml DEAE-Cellulofine column equilibrated with the same buffer. After washing with the same buffer, elution was carried out with a gradient of 100 mM to 400 mM sodium chloride to collect a fraction with an activity of degrading a sulfated glucuronofucan as determined according to the method as described above. Each fraction contained 10 ml of the eluate.

The thus obtained fraction having an activity of degrading a sulfated glucuronofucan was fractionated on a Sephacryl S-200 column (4.4×100 cm) using 10 mM imidazole-hydrochloride buffer (pH 7.5) containing 100 mM sodium chloride, 10 mM calcium chloride and 5 mM sodium azide as an eluent to collect fractions with activities of degrading a sulfated glucuronofucan as determined according to the method as described above as purified eluted fractions. Each fraction contained 13.5 ml of the eluate.

(2) Preparation of Sulfated Glucuronofucan Oligosaccharides

Sulfated glucuronofucan oligosaccharides were prepared using the purified non-adsorbed fraction and the purified eluted fraction.

Briefly, 10 g of the crude sulfated glucuronofucan fraction was dissolved in 1 l of 10 mM imidazole-hydrochloride buffer (pH 6.6) containing 250 mM sodium chloride, 20 mM calcium chloride, 5 mM sodium azide and 1 g of bovine serum albumin. 100 mU of the purified eluted fraction and 600 mU of the purified non-adsorbed fraction were then added thereto. The mixture was reacted at 30° C. for 10 days. A supernatant obtained by centrifuging the reaction mixture was subjected to an ultrafiltration device equipped with hollow fibers with exclusion molecular weight of 10,000 to collect a fraction of oligosaccharides having molecular weight of 10,000 or less. This fraction was designated as a sulfated glucuronofucan enzymatic digestion product fraction 3.

(3) Purification of Sulfated Glucuronofucan Oligosaccharides

The sulfated glucuronofucan enzymatic digestion product fraction 3 was desalted using a desalting apparatus (Micro Acilyzer G3, Asahi Kasei). Imidazole and sodium chloride were added to the desalted sulfated glucuronofucan enzymatic digestion product fraction 3 at final concentrations of 5 mM and 10 mM, respectively. The resulting mixture was loaded onto a 1-l DEAE-Cellulofine A-800 column equilibrated with 5 mM imidazole-hydrochloride buffer (pH 7.0) containing 10 mM sodium chloride. After adequately washing with the same buffer, elution was then carried out with a gradient of 10 mM to 400 mM sodium chloride. The total sugar content and the total uronic acid content of each of the eluted fractions were measured according to the phenol-sulfuric acid method and the carbazole-sulfuric acid method, respectively. As a result, the eluted fractions formed at least five distinct peaks. The fractions in each peak were combined, concentrated to 40 ml using an evaporator, loaded onto a Cellulofine GCL-25 column equilibrated with 10% ethanol and eluted with 10% ethanol for desalting. The sulfated glucuronofucan oligosaccharides, or the oligosaccharides, 3-(1) to (5) of the present invention were obtained as described above.

(4) Structural Analyses of Oligosaccharides

The desalted oligosaccharides 3-(1) to (5) were subjected to analyses of saccharides at the reducing ends and saccharide compositions according to the fluorescence labeling method using 2-aminopyridine. As a result, the saccharide at the reducing end for each of the oligosaccharides was determined to be fucose. Regarding the saccharide composition, the oligosaccharide 3-(2) consisted only of fucose whereas the oligosaccharides 3-(1) and 3-(3) to (5) consisted of fucose and glucuronic acid. Next, determination of the sulfuric acid content (measured according to the turbidimetric method using barium chloride) and the uronic acid content (measured according to the carbazole-sulfuric acid method), mass spectrometric analysis using a mass spectrometer API-III (Perkin-Elmer Sciex) and NMR analysis using a nuclear magnetic resonance apparatus JNM-α500 (Nippon Denshi) were carried out. Samples to be analyzed were subjected to structural analyses after exchange for heavy water according to a conventional method. Bonds of constituting saccharides were analyzed using the HMBC method, a method for $^1$H-detection of heteronuclei. The DQF-COSY method and the HOHAHA method were used for identification in $^1$H-NMR. The HSQC method was used for identification in $^{13}$C-NMR. Physical properties of the oligosaccharides 3-(2) to (5) are shown below.

(a) Physical Properties of the Oligosaccharide 3-(2)

As a result of the above-mentioned analyses, it was demonstrated that this substance was identical to the oligosaccharide 1-(1).

(b) Physical Properties of the Oligosaccharide 3-(3)

Figure 29:
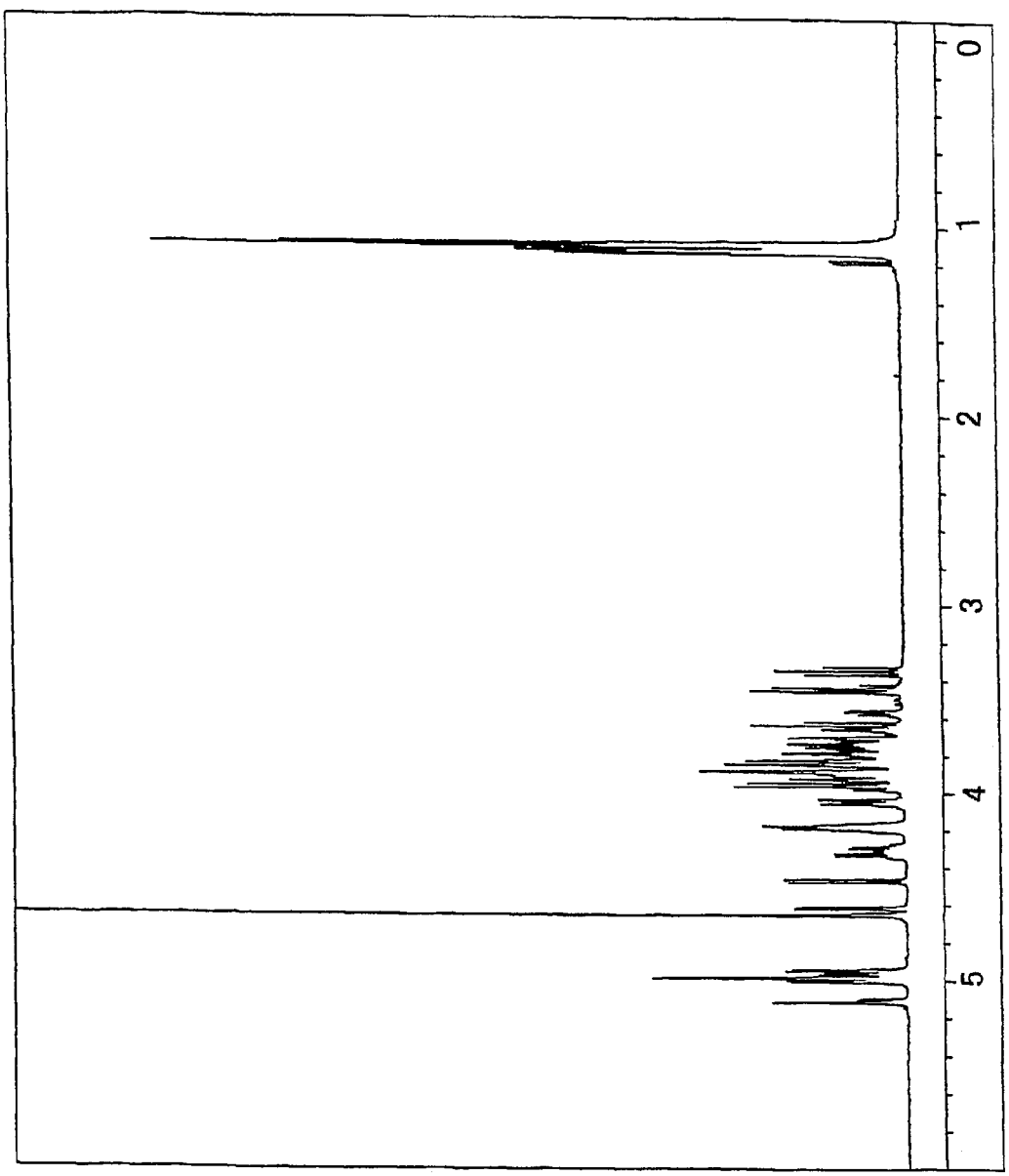
FIG. 29: a figure which illustrates the $^1$H-NMR spectrum of the sulfated glucuronofucan oligosaccharide 3-(3) according to the present invention.
Figure 30:
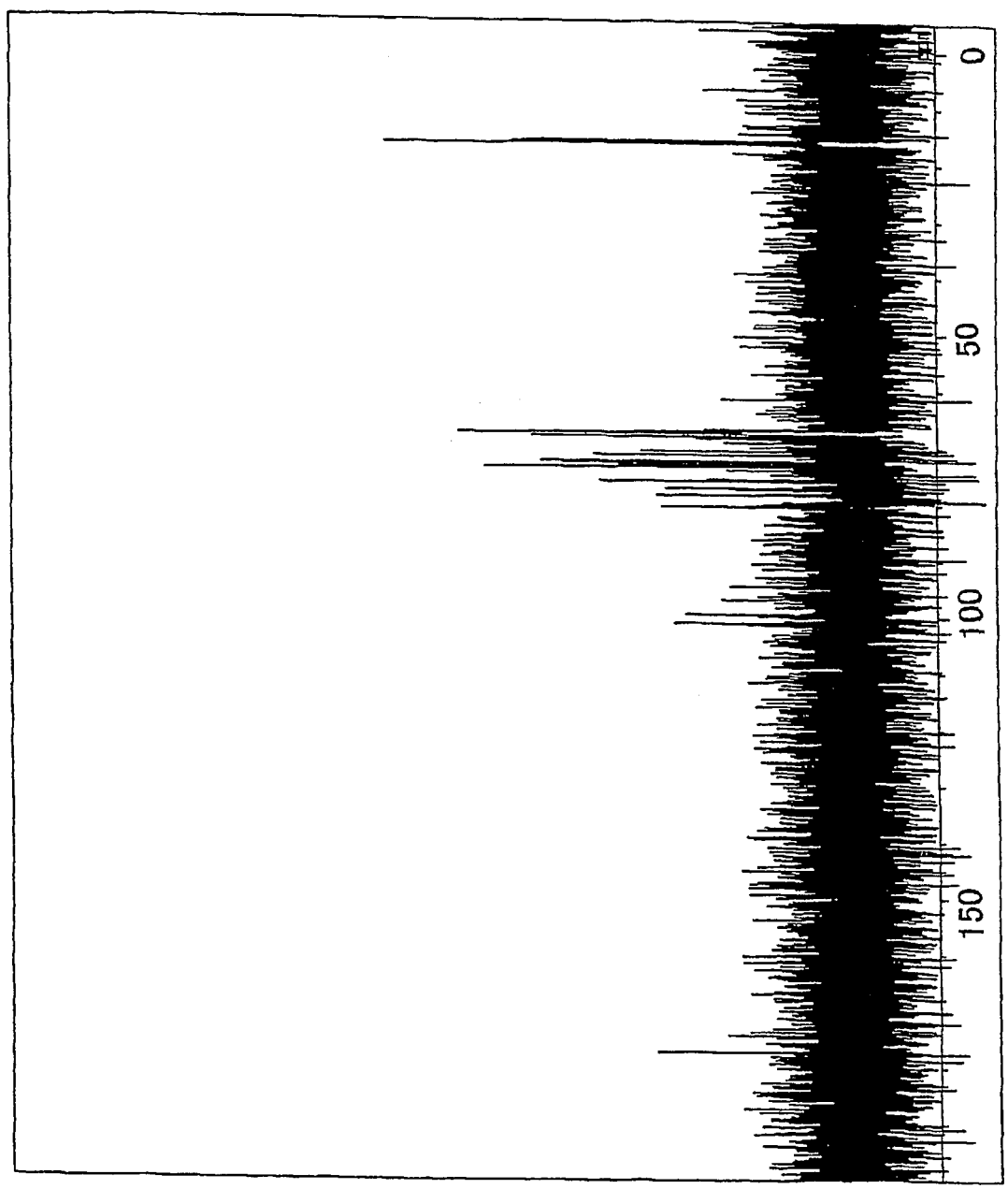
FIG. 30: a figure which illustrates the $^{13}$C-NMR spectrum of the sulfated glucuronofucan oligosaccharide 3-(3) according to the present invention.
Figure 31:
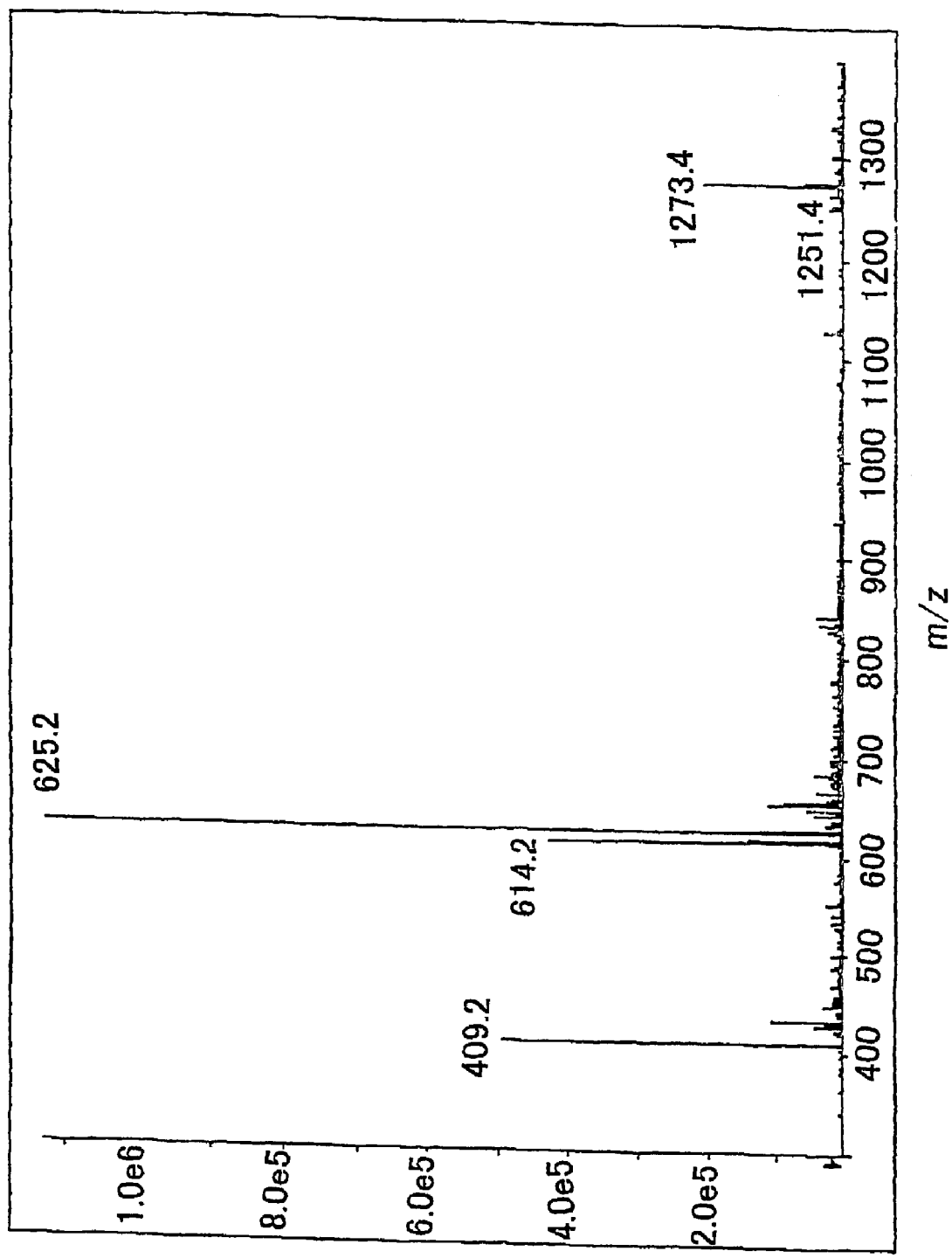
FIG. 31: a figure which illustrates the mass spectrum of the sulfated glucuronofucan, oligosaccharide 3-(3), according to the present invention.

The results for mass spectrometric analysis and identification in NMR analysis are shown below. The $^1$H-NMR spectrum, $^{13}$C-NMR spectrum and mass spectrum of the sulfated glucuronofucan oligosaccharide 3-(3) of the present invention are illustrated in FIGS. 29, 30 and 31, respectively. In FIGS. 29 and 30, the vertical axes represent the signal intensity and the horizontal axes represent the chemical shift value (ppm). In FIG. 31, the vertical axis represents the relative intensity and the horizontal axis represents the m/z value.

Molecular weight: 1230

MS m/z 1273.4 $[M+2Na^+-3H^+]^-$, 625.2 $[M+Na^+-3H^+]^{2-}$, 409.2 $[M-3H^+]^{3-}$

Results of $^1$H-NMR and $^{13}$C-NMR analyses are shown in Table 10.

TABLE 10

| | Chemical shift value (ppm) | |
|---|---|---|
| | $^{13}$C-NMR | $^1$H-NMR Chemical shift value, multiplicity, coupling constant |
| F1-1 | 96.9 | 4.47, d, 8.0 |
| F1-2 | 70.7 | 3.44, dd, 8.0, 10.0 |
| F1-3 | 78.4 | 3.57, dd, 3.0, 10.0 |
| F1-4 | 68.5 | 3.85, d, 3.0 |
| F1-5 | 71.3 | 3.66, q, 6.5 |
| F1-6 | 16.5 | 1.13, d, 6.5 |
| F2-1 | 96.2 | 4.96, d, 4.0 |
| F2-2 | 67.1 | 3.81, dd, 4.0, 10.0 |
| F2-3 | 75.6 | 3.90, dd, 3.0, 10.0 |

TABLE 10-continued

| | Chemical shift value (ppm) | |
|---|---|---|
| | $^{13}$C-NMR | $^1$H-NMR Chemical shift value, multiplicity, coupling constant |
| F2-4 | 69.2 | 3.93, d, 3.0 |
| F2-5 | 66.8 | 4.06, q, 6.5 |
| F2-6 | 16.5 | 1.09, d, 6.5 |
| F3-1 | 96.5 | 4.98, d, 4.0 |
| F3-2 | 67.4 | 3.84, dd, 4.0, 11.0 |
| F3-3 | 77.5 | 3.97, dd, 2.5, 11.0 |
| F3-4 | 80.4 | 4.65, d, 2.5 |
| F3-5 | 67.2 | 4.29, q, 6.5 |
| F3-6 | 16.5 | 1.13, d, 6.5 |
| F4-1 | 100.0 | 4.98, d, 4.0 |
| F4-2 | 68.0 | 3.75, dd, 4.0, 11.0 |
| F4-3 | 77.2 | 3.89, dd, 2.5, 11.0 |
| F4-4 | 80.4 | 4.61, d, 2.5 |
| F4-5 | 67.5 | 4.33, q, 6.5 |
| F4-6 | 16.5 | 1.11, d, 6.5 |
| F5-1 | 99.5 | 4.95, d, 4.0 |
| F5-2 | 67.7 | 3.73, dd, 4.0, 11.0 |
| F5-3 | 74.0 | 3.84, m |
| F5-4 | 68.2 | 3.89, m |
| F5-5 | 68.0 | 4.19, m |
| F5-6 | 16.0 | 1.09, d, 7.0 |
| F6-1 | 94.4 | 5.00, d, 4.0 |
| F6-2 | 75.9 | 3.77, dd, 4.0, 10.5 |
| F6-3 | 70.0 | 4.05, dd, 3.5, 10.5 |
| F6-4 | 73.1 | 3.70, d, 3.5 |
| F6-5 | 67.6 | 4.17, q, 6.5 |
| F6-6 | 16.0 | 1.09, d, 6.5 |
| GA1-1 | 99.5 | 5.11, d, 4.0 |
| GA1-2 | 71.3 | 3.45, dd, 4.0, 10.0 |
| GA1-3 | 73.3 | 3.64, t, 10.0 |
| GA1-4 | 72.0 | 3.35, t, 10.0 |
| GA1-5 | 72.6 | 3.96, d, 10.0 |
| GA1-6 | 176.7 | |

Saccharide composition: L-fucose:D-glucuronic acid=6:1

Sulfate group: 2 molecules

The numbers for peak identification in $^1$H-NMR and $^{13}$C-NMR are as indicated in formula (XIV) below:

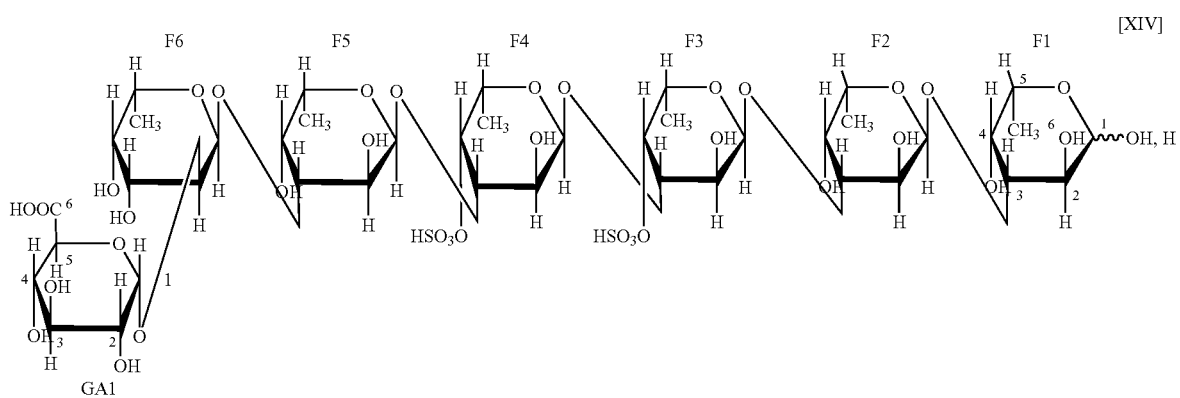

[XIV]

This substance is referred to as 6Fuc-2S-1G1cUA hereinafter.

(c) Physical Properties of the Oligosaccharide 3-(4)

Figure 32:
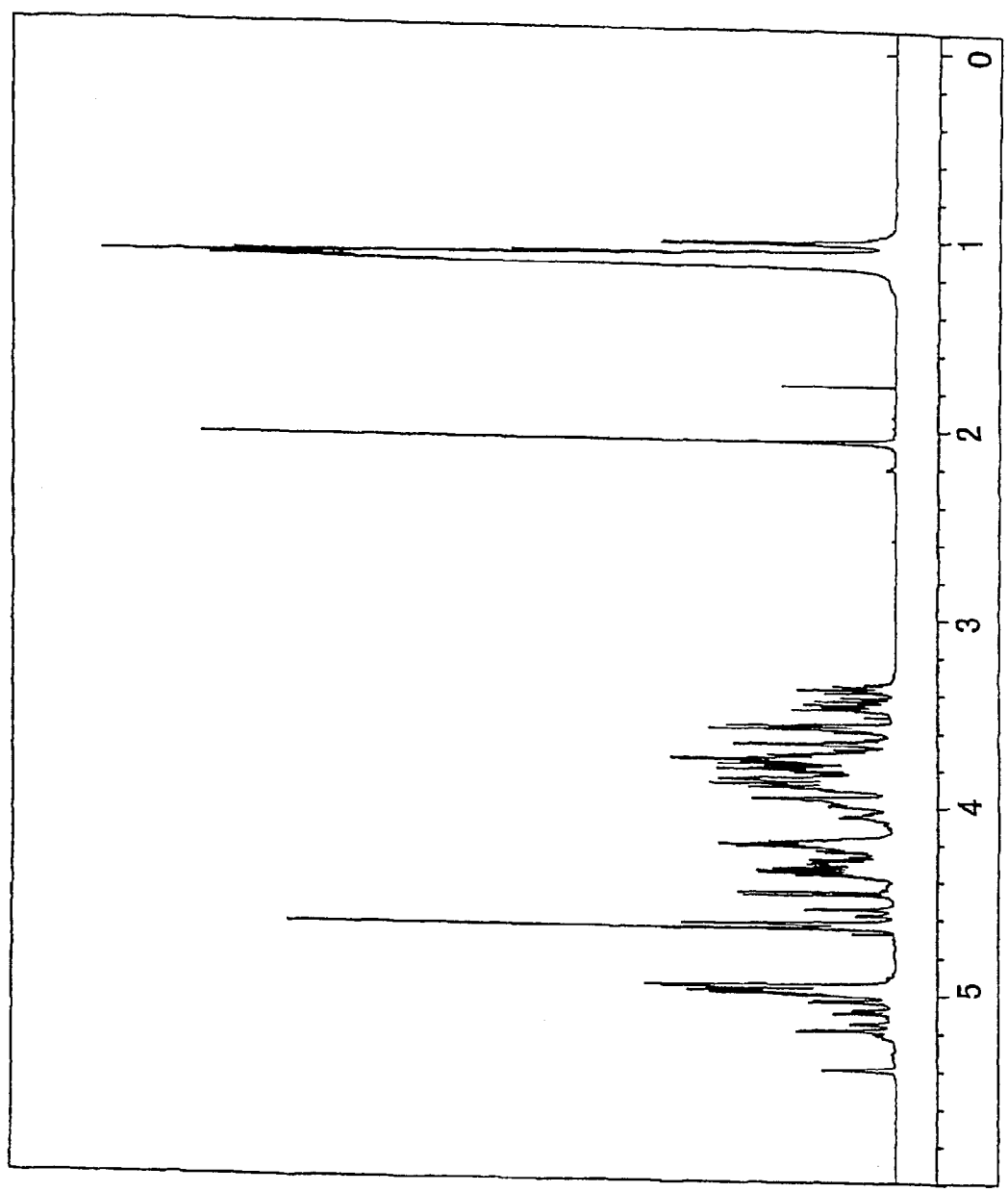
FIG. 32: a figure which illustrates the $^1$H-NMR spectrum of the sulfated glucuronofucan oligosaccharide 3-(4) according to the present invention.
Figure 33:
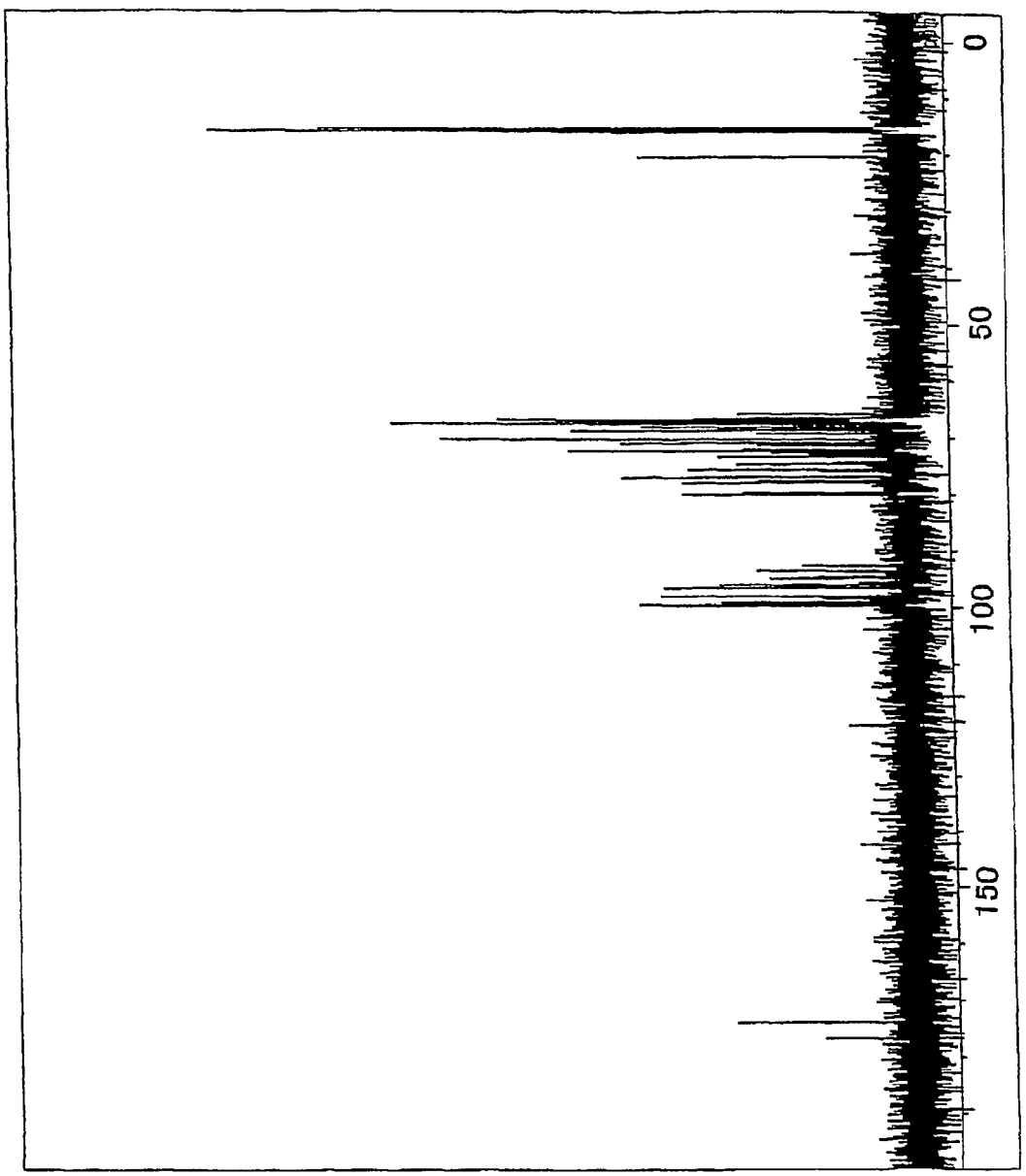
FIG. 33: a figure which illustrates the $^{13}$C-NMR spectrum of the sulfated glucuronofucan oligosaccharide 3-(4) according to the present invention.
Figure 34:
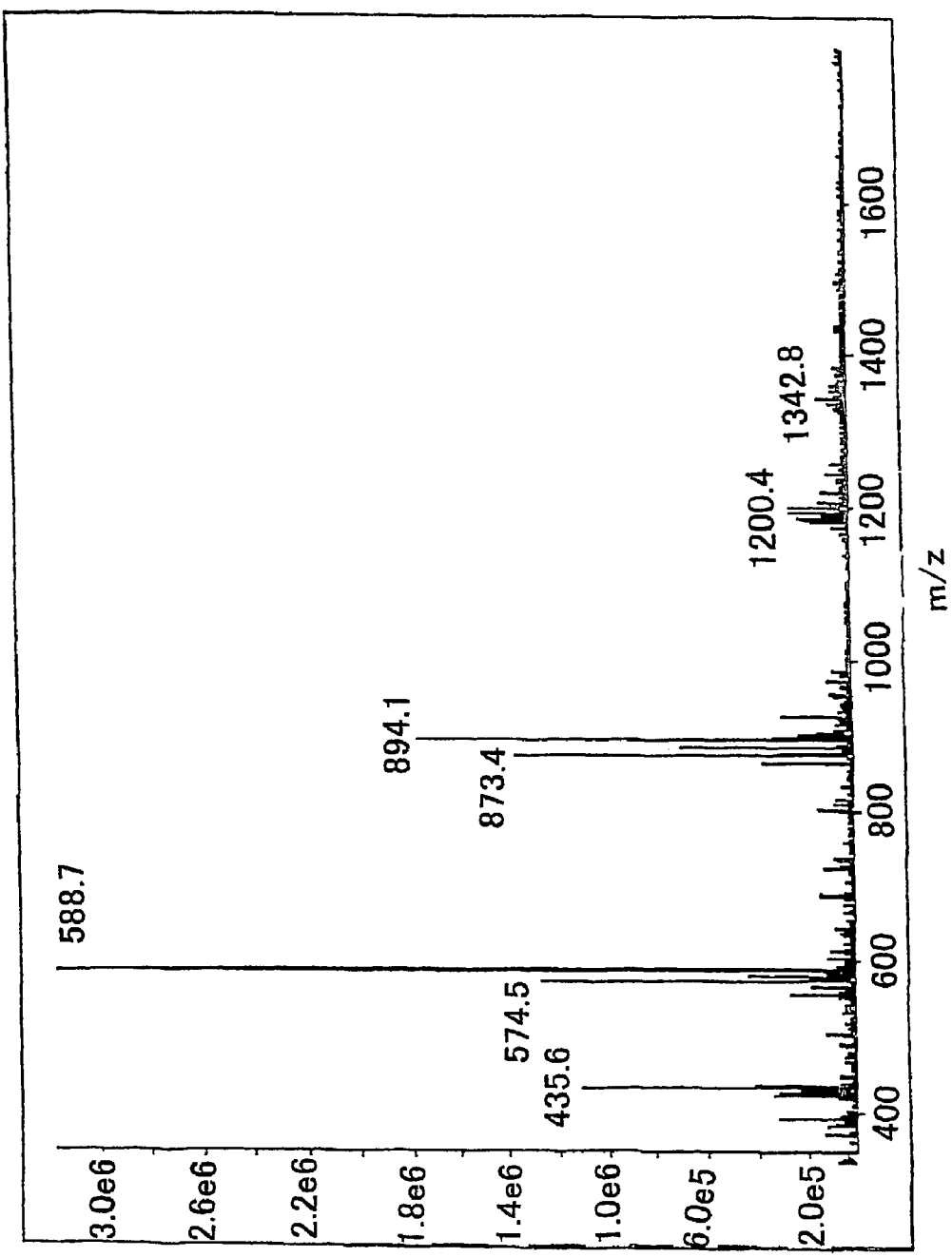
FIG. 34: a figure which illustrates the mass spectrum of the sulfated glucuronofucan, oligosaccharide 3-(4), according to the present invention.

The results for mass spectrometric analysis and identification in NMR analysis are shown below. The $^1$H-NMR spectrum, $^{13}$C-NMR spectrum and mass spectrum of the sulfated glucuronofucan oligosaccharide 3-(4) of the present invention are illustrated in FIGS. 32, 33 and 34, respectively. In FIGS. 32 and 33, the vertical axes represent the signal intensity and the horizontal axes represent the chemical shift value (ppm). In FIG. 34, the vertical axis represents the relative intensity and the horizontal axis represents the m/z value.

Molecular weight: 1724

MS m/z 894.1 $[M+3Na^+-5H^+]^{2-}$, 588.7 $[M+2Na^+-5H^+]^{3-}$, 435.6 $[M+Na^+-5H^+]^{4-}$

Results of $^1$H-NMR and $^{13}$C-NMR analyses are shown in Table 11.

TABLE 11

| | Chemical shift value (ppm) | |
|---|---|---|
| | | $^1$H-NMR Chemical shift value, multiplicity, |
| | $^{13}$C-NMR | coupling constant |
| F1-1 | 96.4 | 4.47, d, 7.9 |
| F1-2 | 70.2 | 3.44, dd, 7.9, 9.9 |
| F1-3 | 77.9 | 3.57, m |
| F1-4 | 68.0 | 3.85, m |
| F1-5 | 70.8 | 3.66, q, 6.7 |
| F1-6 | 15.9 | 1.13, d, 6.7 |
| F2-1 | 95.9 | 4.98, d, 4.0 |
| F2-2 | 67.0 | 3.85, m |
| F2-3 | 76.9 | 3.98, m |
| F2-4 | 79.9 | 4.65, m |
| F2-5 | 66.7 | 4.29, q, 6.7 |
| F2-6 | 15.9 | 1.13, d, 6.7 |
| F3-1 | 99.4 | 5.00, d, 4.0 |
| F3-2 | 67.5 | 3.75, dd, 4.0, 10.4 |
| F3-3 | 76.8 | 3.89, dd, 2.8, 10.4 |
| F3-4 | 80.0 | 4.62, d, 2.8 |
| F3-5 | 66.9 | 4.35, q, 6.7 |
| F3-6 | 16.0 | 1.11, d, 6.7 |
| F4-1 | 99.0 | 4.96, d, 4.0 |
| F4-2 | 67.1 | 3.74, dd, 4.0, 10.4 |
| F4-3 | 74.7 | 3.88, dd, 3.1, 10.4 |
| F4-4 | 68.6 | 3.96, d, 3.1 |
| F4-5 | 67.4 | 4.21, q, 6.7 |

TABLE 11-continued

| | Chemical shift value (ppm) | |
|---|---|---|
| | | $^1$H-NMR Chemical shift value, multiplicity, |
| | $^{13}$C-NMR | coupling constant |
| F4-6 | 15.5 | 1.10, d, 6.7 |
| F5-1 | 94.7 | 5.04, d, 4.0 |
| F5-2 | 70.8 | 4.20, dd, 4.0, 10.4 |
| F5-3 | 70.7 | 4.32, dd, 2.5, 10.4 |
| F5-4 | 69.2 | 5.40, d, 2.5 |
| F5-5 | 65.7 | 4.36, q, 6.7 |
| F5-6 | 15.3 | 1.02, d, 6.7 |
| CH$_3$ of acetyl group | 20.5 | 2.06, s |
| CO of acetyl group | 173.9 | |
| F6-1 | 93.4 | 4.98, d, 4.0 |
| F6-2 | 66.6 | 3.78, dd, 4.0, 10.4 |
| F6-3 | 77.5 | 3.82, dd, 2.5, 10.4 |
| F6-4 | 79.8 | 4.55, d, 2.5 |
| F6-5 | 66.5 | 4.35, q, 6.7 |
| F6-6 | 16.0 | 1.13, d, 6.7 |
| F7-1 | 99.7 | 4.96, d, 4.0 |
| F7-2 | 67.6 | 3.71, dd, 4.0, 10.4 |
| F7-3 | 75.6 | 3.89, dd, 2.8, 10.4 |
| F7-4 | 79.6 | 4.64, d, 2.8 |
| F7-5 | 66.7 | 4.25, q, 6.7 |
| F7-6 | 16.2 | 1.11, d, 6.7 |
| F8-1 | 97.9 | 4.96, d, 4.0 |
| F8-2 | 68.7 | 3.57, dd, 4.0, 10.4 |
| F8-3 | 70.2 | 3.76, dd, 3.1, 10.4 |
| F8-4 | 72.3 | 3.66, d, 3.1 |
| F8-5 | 67.4 | 4.20, q, 6.7 |
| F8-6 | 15.4 | 1.08, d, 6.7 |
| GA1-1 | 99.5 | 5.19, d, 4.0 |
| GA1-2 | 71.3 | 3.47, dd, 4.0, 9.8 |
| GA1-3 | 73.3 | 3.58, t, 9.8 |
| GA1-4 | 72.0 | 3.37, t, 9.8 |
| GA1-5 | 72.6 | 3.81, d, 9.8 |
| GA1-6 | 176.7 | |

Saccharide composition: L-fucose:D-glucuronic acid 8:1

Sulfate group: 4 molecules

Acetyl group: 1 molecule

The numbers for peak identification in $^1$H-NMR and $^{13}$C-NMR are as indicated in formula (IX) below:

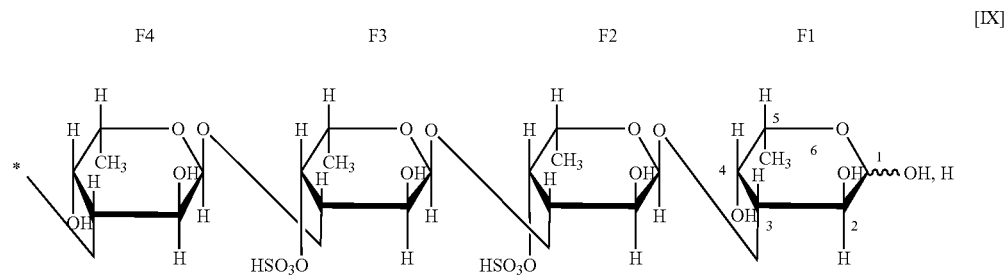

-continued

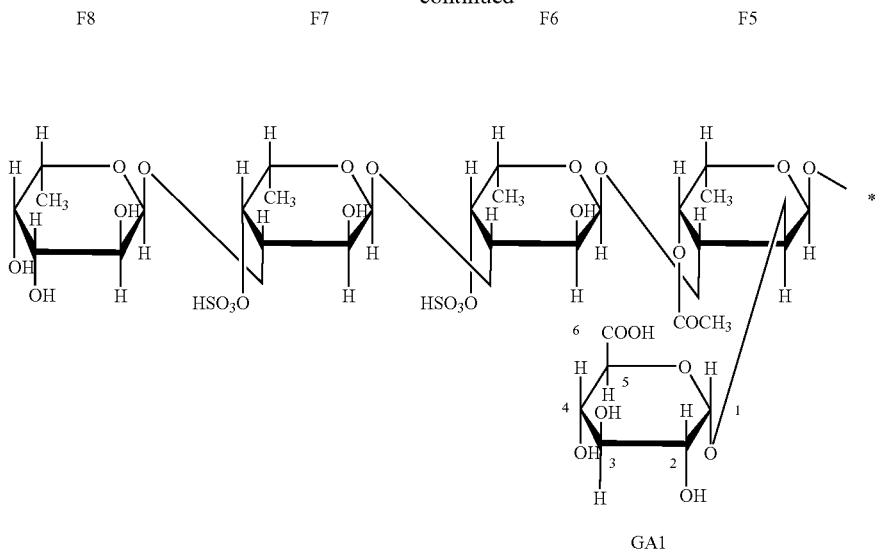

GA1

This substance is referred to as 8Fuc-4S-1G1cUA-1 acetyl hereinafter.

(d) Physical Properties of the Oligosaccharide 3-(5)

Figure 35:
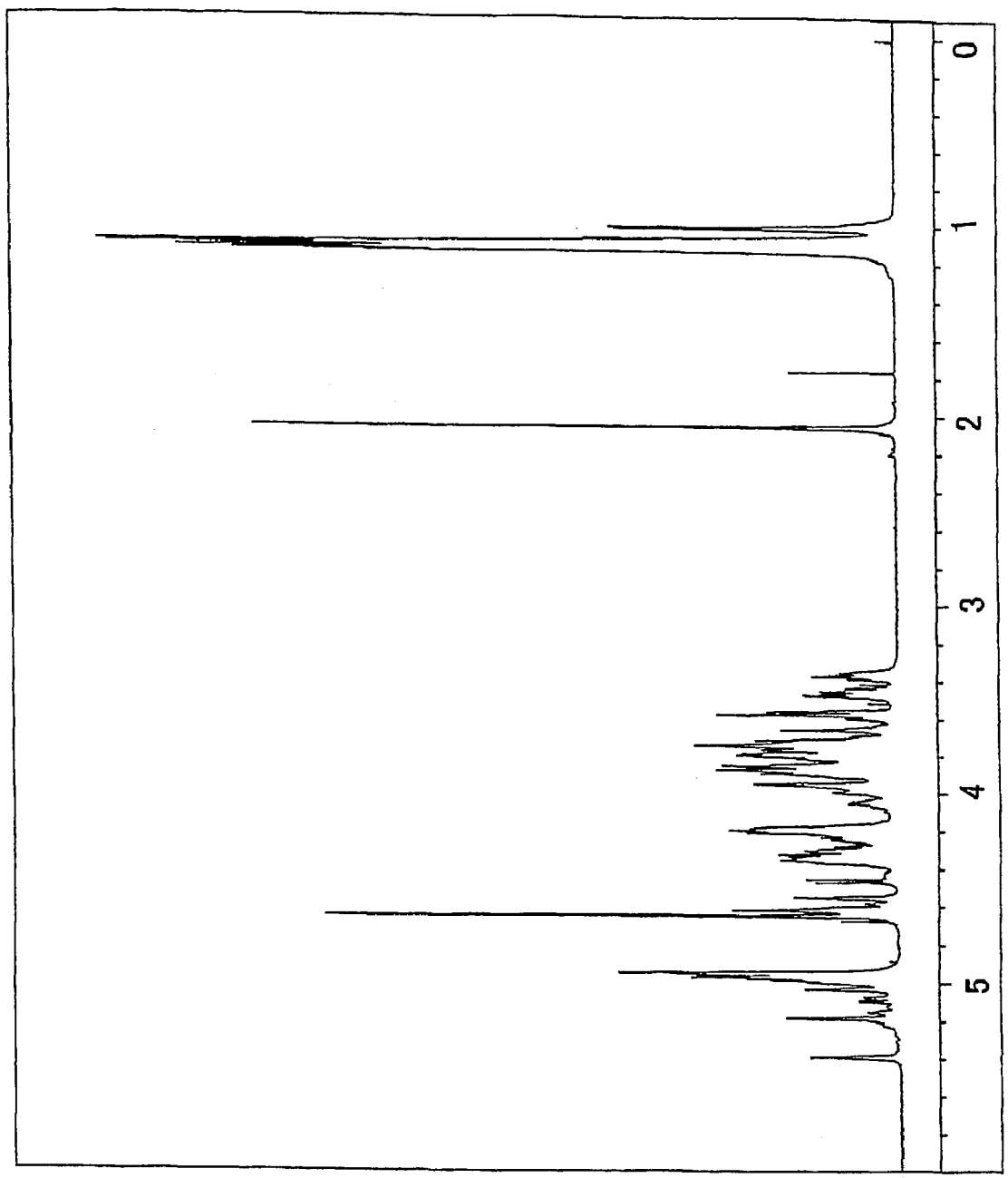
FIG. 35: a figure which illustrates the $^1$H-NMR spectrum of the sulfated glucuronofucan oligosaccharide 3-(5) according to the present invention.
Figure 36:
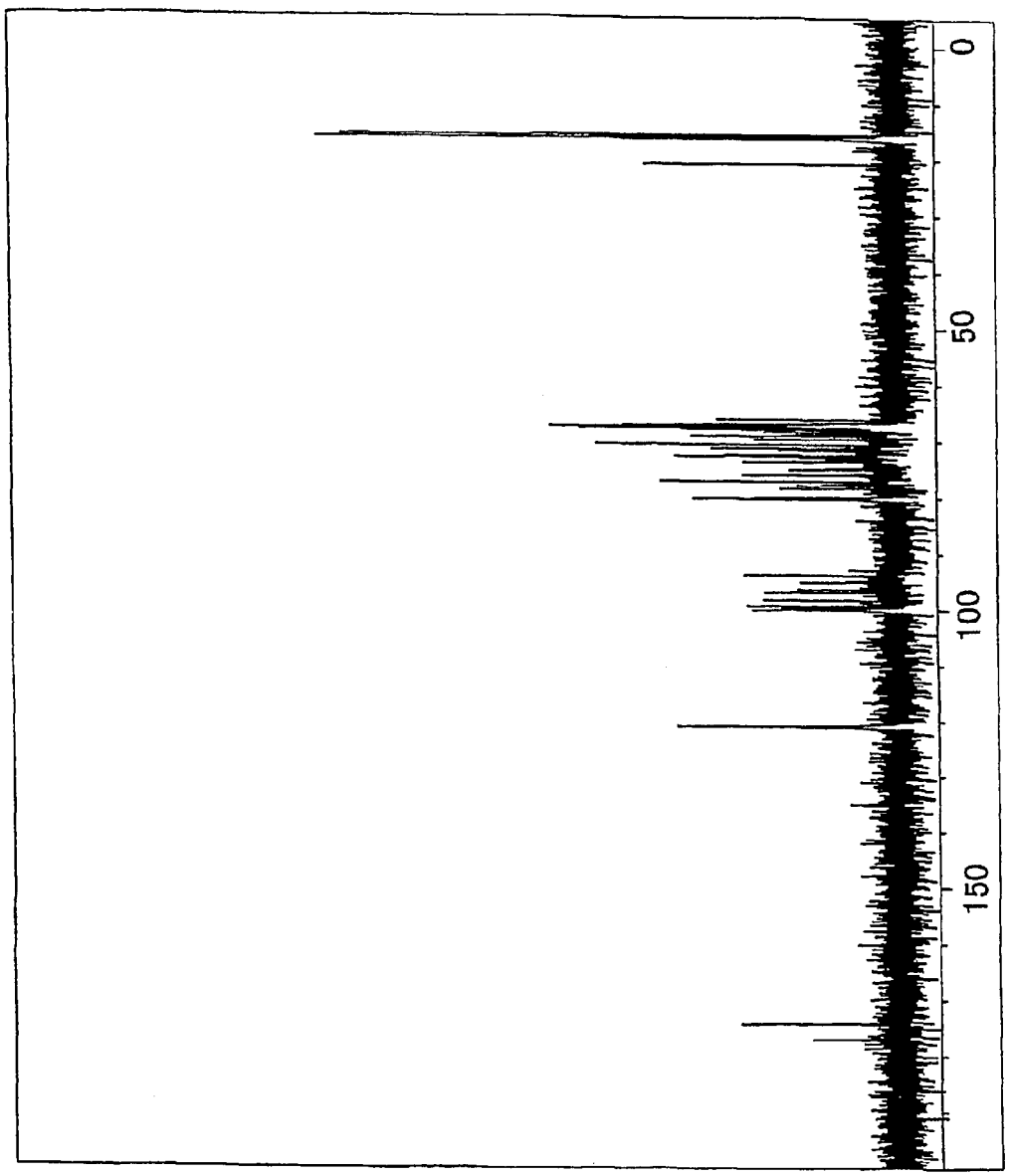
FIG. 36: a figure which illustrates the $^{13}$C-NMR spectrum of the sulfated glucuronofucan oligosaccharide 3-(5) according to the present invention.
Figure 37:
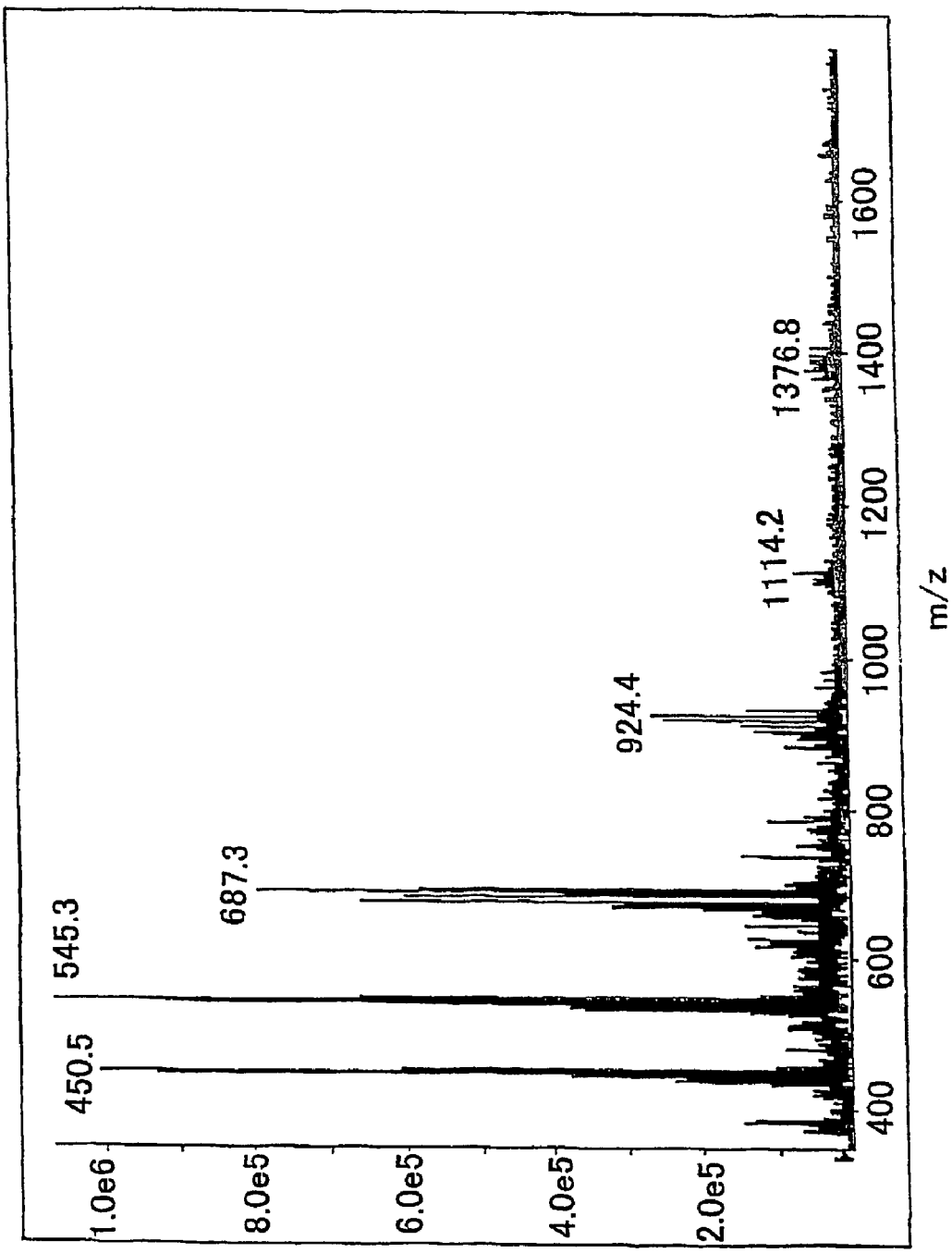
FIG. 37: a figure which illustrates the mass spectrum of the sulfated glucuronofucan, oligosaccharide 3-(5), according to the present invention.

The results for mass spectrometric analysis and identification in NMR analysis are shown below. The $^1$H-NMR spectrum, $^{13}$C-NMR spectrum and mass spectrum of the sulfated glucuronofucan oligosaccharide 3-(5) of the present invention are illustrated in FIGS. 35, 36 and 37, respectively. In FIGS. 35 and 36, the vertical axes represent the signal intensity and the horizontal axes represent the chemical shift value (ppm). In FIG. 37, the vertical axis represents the relative intensity and the horizontal axis represents the m/z value.

Molecular weight: 2689

MS m/z 924.0 [M+4Na$^+$−7H$^+$]$^{3−}$, 687.3 [M+3Na$^+$−7H$^+$]$^{4−}$, 545.3 [M+2Na$^+$−7H$^+$]$^{5−}$, 450.5 [M+Na$^+$−7H$^+$]$^{6−}$

Results of $^1$H-NMR and $^{13}$C-NMR analyses are shown in Table 12.

TABLE 12

| | Chemical shift value (ppm) | |
|---|---|---|
| | $^{13}$C-NMR | $^1$H-NMR Chemical shift value, multiplicity, coupling constant |
| F1-1 | 96.8 | 4.46, d, 7.9 |
| F1-2 | 70.5 | 3.43, dd, 7.9, 10.0 |
| F1-3 | 78.3 | 3.57, m |
| F1-4 | 68.3 | 3.85, m |
| F1-5 | 71.2 | 3.65, q, 6.7 |
| F1-6 | 16.2 | 1.12, d, 6.7 |
| F2-1 | 96.3 | 4.97, d, 4.0 |
| F2-2 | 67.3 | 3.85, m |
| F2-3 | 77.1 | 3.97, m |
| F2-4 | 80.1 | 4.65, m |
| F2-5 | 67.1 | 4.29, q, 6.7 |
| F2-6 | 16.2 | 1.12, d, 6.7 |
| F3-1 | 99.7 | 4.98, d 4.0 |
| F3-2 | 67.9 | 3.74, m |
| F3-3 | 77.1 | 3.88, m |
| F3-4 | 80.3 | 4.62, m |
| F3-5 | 67.3 | 4.35, q, 6.7 |
| F3-6 | 16.3 | 1.11, d, 6.7 |

TABLE 12-continued

| | Chemical shift value (ppm) | |
|---|---|---|
| | $^{13}$C-NMR | $^1$H-NMR Chemical shift value, multiplicity, coupling constant |
| F4-1 | 99.3 | 4.94, d, 4.0 |
| F4-2 | 67.4 | 3.73, m |
| F4-3 | 75.0 | 3.87, m |
| F4-4 | 69.0 | 3.95, m |
| F4-5 | 67.7 | 4.20, q, 6.7 |
| F4-6 | 15.9 | 1.10, d, 6.7 |
| F5-1 | 95.0 | 5.03, d, 4.0 |
| F5-2 | 71.1 | 4.20, m |
| F5-3 | 71.1 | 4.31, m |
| F5-4 | 69.6 | 5.39, m |
| F5-5 | 66.1 | 4.36, q, 6.7 |
| F5-6 | 15.6 | 1.01, d, 6.7 |
| CH$_3$ of acetyl group of F5 | 20.8 | 2.06, s |
| CO of acetyl group of F5 | 174.2 | |
| F6-1 | 93.7 | 4.97, d, 4.0 |
| F6-2 | 66.9 | 3.79, m |
| F6-3 | 77.8 | 3.82, m |
| F6-4 | 80.1 | 4.55, m |
| F6-5 | 66.9 | 4.35, q, 6.7 |
| F6-6 | 16.3 | 1.12, d, 6.7 |
| F7-1 | 99.9 | 4.94, d, 4.0 |
| F7-2 | 67.9 | 3.70, m |
| F7-3 | 75.9 | 3.88, m |
| F7-4 | 79.9 | 4.64, m |
| F7-5 | 67.1 | 4.24, q, 6.7 |
| F7-6 | 16.5 | 1.11, d, 6.7 |
| F8-1 | 99.3 | 4.94, d, 4.0 |
| F8-2 | 67.4 | 3.73, m |
| F8-3 | 75.0 | 3.87, m |
| F8-4 | 69.0 | 3.95, m |
| F8-5 | 67.7 | 4.20, q, 6.7 |
| F8-6 | 15.9 | 1.10, d, 6.7 |
| F9-1 | 95.0 | 5.03, d, 4.0 |
| F9-2 | 71.1 | 4.20, m |
| F9-3 | 71.1 | 4.31, m |
| F9-4 | 69.6 | 5.39, m |
| F9-5 | 66.1 | 4.36, q, 6.7 |
| F9-6 | 15.6 | 1.01, d, 6.7 |

TABLE 12-continued

| | Chemical shift value (ppm) | |
|---|---|---|
| $^{13}$C-NMR | $^{1}$H-NMR Chemical shift value, multiplicity, coupling constant | |
| CH$_3$ of acetyl group of F9 | 20.8 | 2.06, s |
| CO of acetyl group of F9 | 174.2 | |
| F10-1 | 93.7 | 4.97, d, 4.0 |
| F10-2 | 66.9 | 3.79, m |
| F10-3 | 77.8 | 3.82, m |
| F10-4 | 80.1 | 4.55, m |
| F10-5 | 66.9 | 4.35, q, 6.7 |
| F10-6 | 16.3 | 1.12, d, 6.7 |
| F11-1 | 99.9 | 4.94, d, 4.0 |
| F11-2 | 67.9 | 3.70, m |
| F11-3 | 75.9 | 3.88, m |
| F11-4 | 79.9 | 4.64, m |
| F11-5 | 67.1 | 4.24, q, 6.7 |
| F11-6 | 16.5 | 1.11, d, 6.7 |
| F12-1 | 98.2 | 4.94, d, 4.0 |
| F12-2 | 69.1 | 3.57, m |
| F12-3 | 70.5 | 3.75, m |
| F12-4 | 72.6 | 3.66, m |
| F12-5 | 67.7 | 4.20, q, 6.7 |
| F12-6 | 15.8 | 1.07, d, 6.7 |

TABLE 12-continued

| | Chemical shift value (ppm) | |
|---|---|---|
| $^{13}$C-NMR | $^{1}$H-NMR Chemical shift value, multiplicity, coupling constant | |
| GA1-1 | 99.7 | 5.19, d, 4.0 |
| GA1-2 | 71.6 | 3.47, dd, 4.0, 9.8 |
| GA1-3 | 73.6 | 3.58, t, 9.8 |
| GA1-4 | 72.3 | 3.37, t, 9.8 |
| GA1-5 | 73.0 | 3.81, d, 9.8 |
| GA1-6 | 177.0 | |
| GA2-1 | 99.7 | 5.19, d, 4.0 |
| GA2-2 | 71.6 | 3.47, dd, 4.0, 9.8 |
| GA2-3 | 73.6 | 3.58, t, 9.8 |
| GA2-4 | 72.3 | 3.37, t, 9.8 |
| GA2-5 | 73.0 | 3.81, d, 9.8 |
| GA2-6 | 177.0 | |

Saccharide composition: L-fucose:D-glucuronic acid=12:2

Sulfate group: 6 molecules

Acetyl group: 2 molecule

The numbers for peak identification in $^{1}$H-NMR and $^{13}$C-NMR are as indicated in formula (X) below:

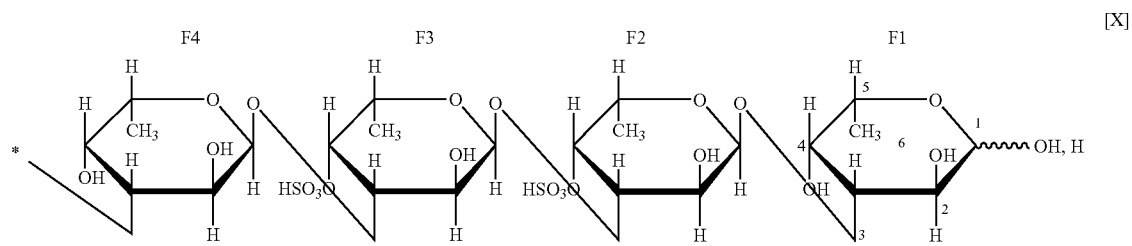

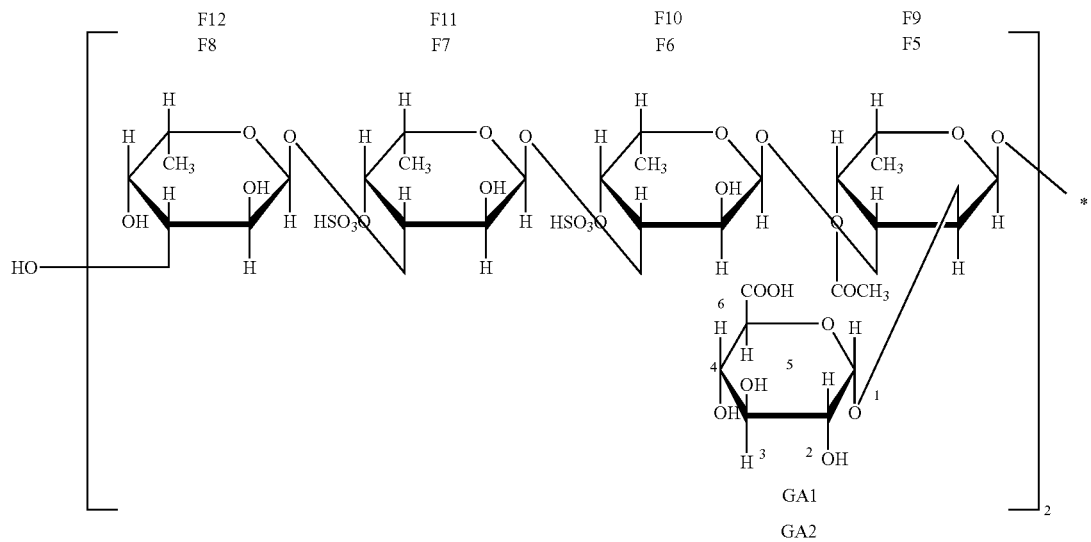

This substance is referred to as 12Fuc-6S-2GlcUA-2 acetyl hereinafter.

Example 12

(1) Purification of α-D-Glucuronidase and Endo-α-L-Fucosidase

Three rounds of cultivation of *Fucophilus fucoidanolyticus* strain SI-1234 was carried as described in Example 9. A cell extract prepared as described in Example 9 from the cultured cells was adequately dialyzed against 10 mM imidazole-hydrochloride buffer (pH 7.5) containing 100 mM sodium chloride and 10 mM calcium chloride and centrifuged to obtain a supernatant as a crude enzyme solution containing the α-D-glucuronidase and the endo-α-L-fucosidase of the present invention. Thereafter, the respective enzymes were purified. In the course of purification, the α-D-glucuronidase activity was determined as described in Example 5(3) and the endo-α-L-fucosidase activity was determined as described in Example 5(6).

The crude enzyme solution was loaded onto a 3-L DEAE-Cellulofine A-800 column equilibrated with the same buffer. After washing with the same buffer, elution was carried out with a gradient of 100 mM to 400 mM sodium chloride to collect a fraction with the α-D-glucuronidase activity and the endo-α-L-fucosidase activity. Each fraction contained 200 ml of the eluate. In the above-mentioned procedure, the two enzymes behaved almost in the same manner and therefore could not be separated each other.

The fraction with the two enzymatic activities was concentrated using an ultrafiltration device equipped with hollow fibers with fractionation molecular weight of 10,000 and the buffer was exchanged for 10 mM imidazole-hydrochloride buffer (pH 7.5) containing 100 mM sodium chloride and 10 mM calcium chloride.

The resulting enzyme solution was loaded onto 240-ml DEAE-Cellulofine A-800 column equilibrated with the same buffer. After washing with the same buffer, elution was carried out with a gradient of 100 mM to 300 mM sodium chloride to collect a fraction with the α-D-glucuronidase activity and the endo-α-L-fucosidase activity. Each fraction contained 25 ml of the eluate. In the above-mentioned procedure, the two enzymes behaved almost in the same manner and therefore could not be separated each other.

The fraction with the two enzymatic activities was concentrated using an ultrafiltration device equipped with hollow fibers with fractionation molecular weight of 10,000 and the buffer was exchanged for 10 mM imidazole-hydrochloride buffer (pH 7.5) containing 50 mM sodium chloride and 5 mM calcium chloride.

The resulting enzyme solution was loaded onto 50-ml Sulfated-Cellulofine (Seikagaku Corporation) column equilibrated with the same buffer. After washing with the same buffer, elution was carried out with a gradient of 50 mM to 1 M sodium chloride to collect a fraction with the α-D-glucuronidase activity and a fraction with the endo-α-L-fucosidase activity. Each fraction contained 50 ml of the eluate. In the above-mentioned procedure, the two enzymes were completely separated each other and purified independently thereafter.

(2) Purification of Endo-α-L-Fucosidase

The fraction with the endo-α-L-fucosidase activity obtained in (1) above was concentrated using an ultrafiltration membrane with fractionation molecular weight of 10,000 and then loaded onto a Sephacryl S-200 column (4.4×100 cm) equilibrated with 10 mM imidazole-hydrochloride buffer (pH 7.5) containing 100 mM sodium chloride, 10 mM calcium chloride and 5 mM sodium azide. Elution was carried out using the same buffer to collect a fraction with the endo-α-L-fucosidase activity. Each fraction contained 13.3 ml of the eluate.

The fraction with the endo-α-L-fucosidase activity was loaded onto a Phenyl-Cellulofine column (2.4×44 cm) equilibrated with a buffer prepared by mixing 10 mM imidazole-hydrochloride buffer (pH 7.5) containing 10 mM sodium chloride and 5 mM calcium chloride with ethanol at a ratio of 85:15. Elution was carried out using the same buffer. Each fraction contained 30 ml of the eluate. The thus obtained active fraction was homogeneous as determined by SDS-polyacrylamide gel electrophoresis. As described above, a purified preparation of the endo-α-L-fucosidase of the present invention was obtained.

(3) Purification of α-D-Glucuronidase

The fraction with the α-D-glucuronidase activity obtained in (1) above was concentrated using an ultrafiltration membrane with fractionation molecular weight of 10,000 and then loaded onto a Sephacryl S-200 column (4.4×100 cm) equilibrated with 10 mM imidazole-hydrochloride buffer (pH 7.5) containing 100 mM sodium chloride, 10 mM calcium chloride and 5 mM sodium azide. Elution was carried out using the same buffer to collect a fraction with the α-D-glucuronidase activity. Each fraction contained 13.3 ml of the eluate.

The fraction of the α-D-glucuronidase of the present invention was adequately dialyzed against 10 mM imidazole-hydrochloride buffer containing 300 mM sodium chloride and 5 mM calcium chloride, and loaded onto a 20-ml Sulfated-Cellulofine column equilibrated with the same buffer. After washing with the same buffer, elution was carried out using a gradient of 300 mM to 900 mM sodium chloride to collect a fraction with the α-D-glucuronidase activity. Each fraction contained 10 ml of the eluate.

The fraction of the α-D-glucuronidase of the present invention was adequately dialyzed against 10 mM imidazole-hydrochloride buffer containing 200 mM sodium chloride and 5 mM calcium chloride, and loaded onto a 20-ml Sulfated-Cellulofine column equilibrated with the same buffer. After washing with the same buffer, elution was carried out using a gradient of 200 mM to 800 mM sodium chloride to collect a fraction with the α-D-glucuronidase activity. Each fraction contained 7 ml of the eluate. The thus obtained active fraction was homogeneous as determined by SDS-polyacrylamide gel electrophoresis. As described above, a purified preparation of the α-D-glucuronidase of the present invention was obtained.

Example 13

Conversion of a sulfated glucuronofucan into smaller molecules was examined using the purified preparation of the endo-α-L-fucosidase of the present invention obtained in Example 12(2) and the purified preparation of the α-D-glucuronidase of the present invention obtained in Example 12(3). First, in order to examine the effect of acetyl groups on degradation of a sulfated glucuronofucan, a deacetylated sulfated glucuronofucan was prepared.

(1) Preparation of Deacetylated Sulfated Glucuronofucan 200 mg of the sulfated glucuronofucan prepared as described in Referential Example 1(1) was dissolved in 20 ml of 1 N sodium hydroxide, treated at 25° C. for 20 hours, and adequately dialyzed against 20 mM imidazole-hydrochloride buffer (pH 6.6) containing 200 mM sodium chloride and 50 mM calcium chloride to obtain a deacetylated sulfated glucuronofucan.

(2) Degradation of Substrates

150 μU of the α-D-glucuronidase of the present invention and 1 mU of the endo-α-L-fucosidase of the present invention were added to 200 mg of the sulfated glucuronofucan prepared as described in Referential Example 1(1) or the deacetylated sulfated glucuronofucan prepared as described in (1) above. Degradation reactions were carried out at 25° C. Each reaction mixture contained the following components at the final concentrations indicated in parentheses: a sulfated glucuronofucan (6.7 mg/ml), bovine serum albumin (0.1 mg/ml), sodium chloride (200 mM), calcium chloride (50 mM) and imidazole (20 mM). The pH was adjusted to 6.6. The molecular weight of the sulfated glucuronofucan at the beginning of the reaction was almost the same as that of the deacetylated sulfated glucuronofucan. After reaction for two days, the average molecular weight of the sulfated glucuronofucan was about 1,950,000 whereas the average molecular weight of the deacetylated sulfated glucuronofucan was about 27,000.

Thus, it was confirmed that deacetylation is necessary for efficiently obtaining sulfated glucuronofucan oligosaccharides using the α-D-glucuronidase and the endo-α-L-fucosidase of the present invention. When the crude enzyme or the partially purified enzyme as described in Example 1 was allowed to act on the sulfated glucuronofucan, almost no acetyl group was found in the resulting oligosaccharides. When the purified non-adsorbed fraction and the purified eluted fraction as described in Example 11(1) were allowed to act on the sulfated glucuronofucan, oligosaccharides having acetyl groups were generated. Based on these results, it was supposed that *Fucophilus fucoidanolyticus* strain SI-1234 of the present invention produces a fucoidan deacetylase which releases acetyl groups from the sulfated glucuronofucan.

Example 14

A fucoidan deacetylase produced by *Fucophilus fucoidanolyticus* strain SI-1234, which releases acetyl groups from the sulfated glucuronofucan, was examined.

(1) Purification of Fucoidan Deacetylase

First, a reaction system for measuring a fucoidan deacetylase activity in the crude enzyme solution from *Fucophilus fucoidanolyticus* strain SI-1234 of the present invention prepared as described in Example 11(1) was established.

Briefly, 20 μl of a fucoidan deacetylase solution was added to 100 μl of 50 mM imidazole-hydrochloride buffer (pH 7.5), 10 μl of 4 M sodium chloride, 1 μl of 1 M calcium chloride, 40 μl of 1% sulfated glucuronofucan and 29 μl of water. The mixture was reacted at 30° C. for 3 hours. The amount of released acetyl groups was measured using a commercially available kit for quantifying acetic acid (F-kit Acetic Acid, Roche Diagnostics). As a result, the activity of the fucoidan deacetylase of the present invention contained in 1 ml of the culture was determined to be about 2 mU.

Alternatively, a fucoidan deacetylase activity was determined using the oligosaccharide 3-(4) fluorescently labeled with 2-aminopyridine at the reducing end as a substrate in the following reaction system.

Reaction System

75 μl of 50 mM sodium phosphate buffer (pH 7.5)
28.5 μl of water
9 μl of 4 M sodium chloride
15 μl of 3 mg/ml bovine serum albumin
15 μl of 4 pmole/μl fluorescently labeled oligosaccharide 3-(4)
7.5 μl of fucoidan deacetylase solution All of the components were mixed together, the mixture was reacted at 30° C. for 1 hour and treated at 100° C. for 10 minutes, and a supernatant obtained by centrifugation was subjected to analysis using HPLC under the following conditions to determine the deacetylation level:

Instrument: L-6200 (Hitachi);

Column: L-column (4.6×250 mm; Chemical Inspection and Testing Institue);

Eluent: 50 mM acetate-triethylamine buffer (pH 5.0) containing 0.5% butanol;

Detection: excitation wavelength at 320 nm and emission wavelength at 400 nm using fluorescence detector F-1150 (Hitachi);

Flow rate: 1 ml/minute; and

Column temperature: 40° C.

One unit of the fucoidan deacetylase of the present invention is defined as an amount of the enzyme that cleaves 1 μmole of acetyl group in 1 minute in the above-mentioned reaction system. Since a product generated upon cleavage of an acetyl group of the substrate in the reaction system had the same structure as that of the PA-labeled sulfated glucuronofucan oligosaccharide 1-(3) obtained in Example 5(1), this PA-labeled one was used to determine the column retention time of the substrate from which an acetyl group was cleaved. The amount of cleaved acetyl group was calculated according to the following equation:

$$DA/60 \times 0.015 = U/\text{ml} \qquad \text{Equation 6}$$

DA: amount of cleaved acetyl group (μmole);

60: reaction time (minutes); and 0.015: volume of enzyme solution (ml).

The activity of the fucoidan deacetylase of the present invention contained in 1 ml of the culture as determined by the above-mentioned method was 0.8 mU/ml. 50 ml of the crude enzyme solution was loaded onto a Sephacryl S-200 column (4.4×100 cm) equilibrated with 10 mM imidazole-hydrochloride buffer (pH 7.5) containing 100 mM sodium chloride, 10 mM calcium chloride and 5 mM sodium azide. Elution was carried out using the same buffer. Each fraction contained 13 ml of the eluate. The activities of the fucoidan deacetylase of the present invention contained in the respective fractions were determined according to the method as described above. The molecular weight of the fucoidan deacetylase of the present invention calculated based on the volume of the eluent was about 30,000 to 50,000.

Figure 2:
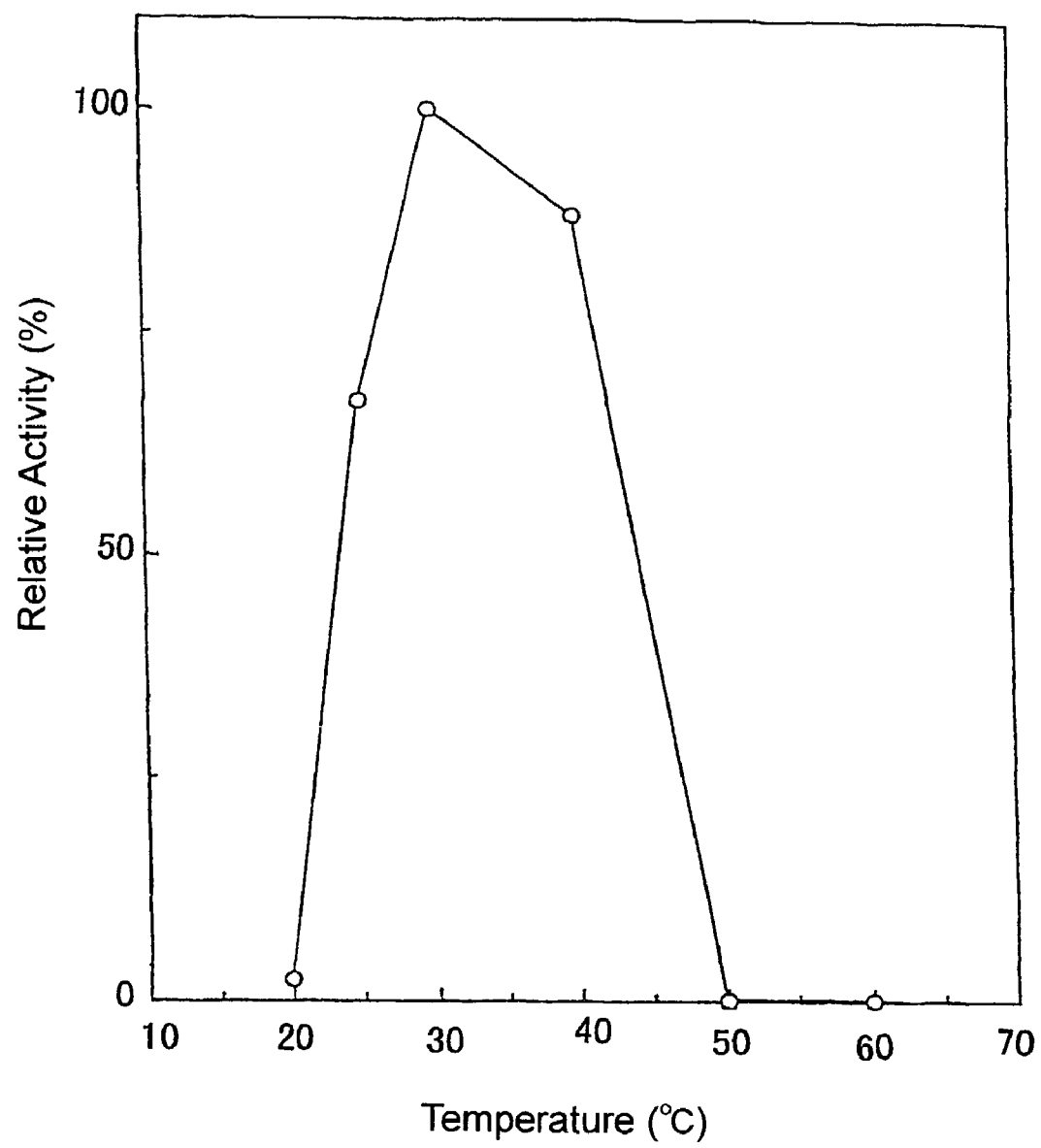
FIG. 2: a graph which illustrates the relationship between temperature (° C.) and the relative activity (%) of the fucoidan deacetylase according to the present invention.

The active fractions were collected and the properties of the fucoidan deacetylase of the present invention were determined. The results are shown in FIGS. 1 and 2. FIGS. 1 and 2 show the optimal pH and the optimal temperature.

As shown in FIG. 1, the optimal pH for the fucoidan deacetylase of the present invention was about 6 to 9.1 and the optimal temperature was 23 to 45° C.

(2) Deacetylation Reaction of Various Fucoidans Using Fucoidan Deacetylase

The following reaction system was constructed and the amounts of acetyl groups contained in various fucoidans were determined.

The fucoidans derived from algae as shown in Table 13 below were used for the reactions.

Reaction System
60 μl of 1% fucoidan
50 μl of 100 mM sodium phosphate buffer (pH 7.5)
10 μl of 4 M sodium chloride
20 μl of 3 mg/ml bovine serum albumin
30 μl of water
30 μl of fucoidan deacetylase All of the components were mixed together, the mixture was reacted at 30° C. for 21 hours. The amount of generated acetic acid was determined using the above-mentioned kit for quantifying acetic acid. Furthermore, each fucoidan was treated in 1 N sodium hydroxide at 25° C. for 18 hours. The amount of generated acetic acid was determined using the above-mentioned kit for quantifying acetic acid. The results are shown in Table 13.

TABLE 13

| Algae | Deacetylase | Sodium hydroxide |
|---|---|---|
| Cladosiphon okamuranus | 13.6 | 17.2 |
| Nemacystus decipiens | n.d. | 1.74 |
| Fucus vesiculosus | 0.91 | 15.4 |
| Ascophyllum nodosum | 0.69 | 7.74 |
| Kjellmaniella crassifolia | 1.27 | 4.40 |
| Laminaria japonica | 2.00 | 11.3 |
| Eisenia bicyclis | 1.70 | 3.77 |
| Sporophyll of Undaria pinnatifida | 2.70 | 30.3 |
| Lessonia nigrescens | 3.80 | 22.9 |
| Macrocystis pyriferra | 1.46 | 12.9 |
| Durvillaea antarctica | 1.84 | 15.3 | mg acetyl group/g fucoidan;
n.d.: not detected.

As shown in Table 13, it was confirmed that the fucoidan deacetylase of the present invention is an enzyme that acts on fucoidans derived from various algae and hydrolyzes acetyl groups. Furthermore, it was confirmed that the fucoidan deacetylase of the present invention has a high specificity for an acetyl group in a fucoidan derived from *Cladosiphon okamuranus* Tokida (i.e., a sulfated glucuronofucan) based on the comparison with the non-specific deacetylation using sodium hydroxide.

Example 15

Figure 38:
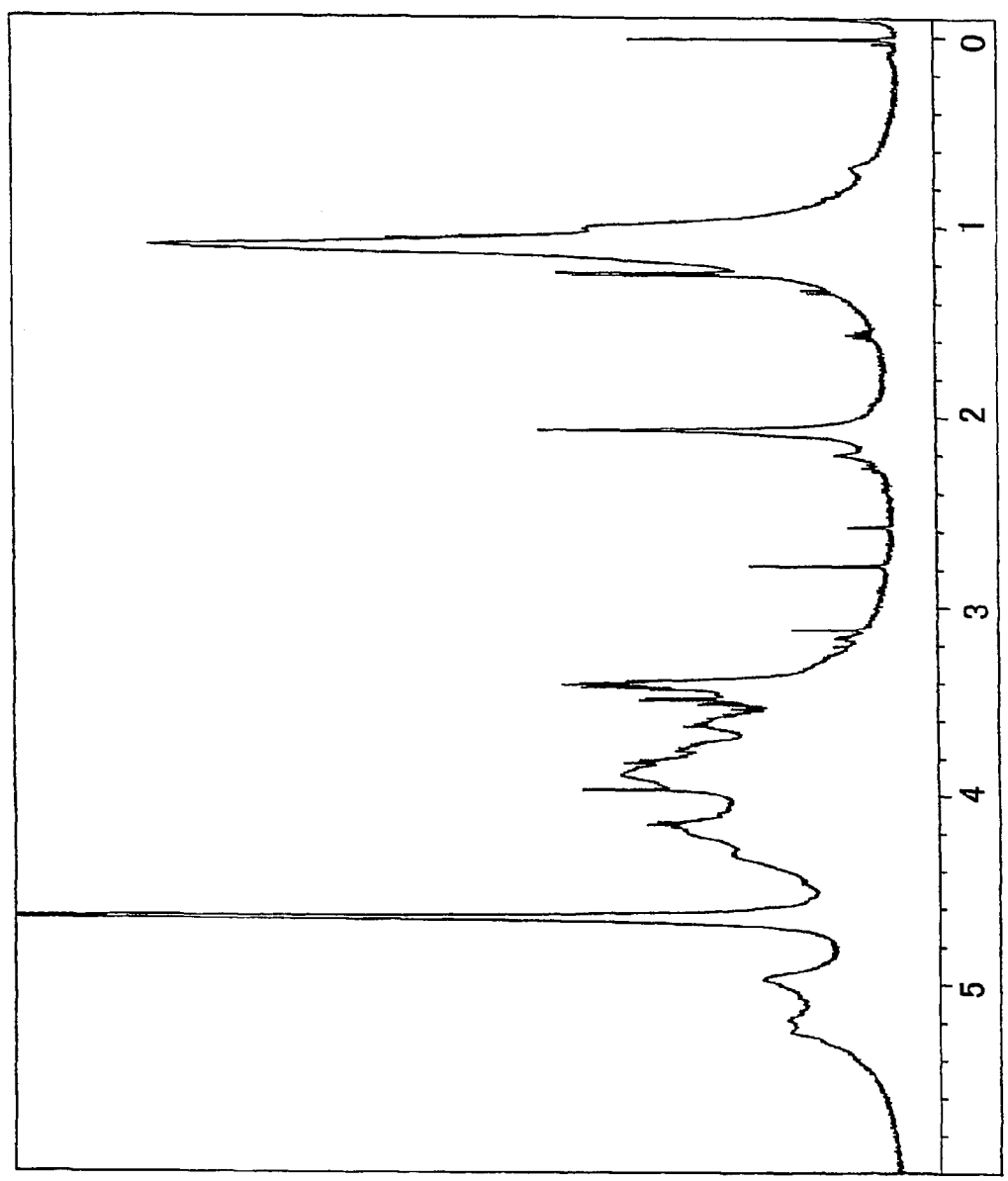
FIGS. 38 and 39: figures which illustrate NMR spectra of the sulfated glucuronofucan, according to the present invention.
Figure 39:
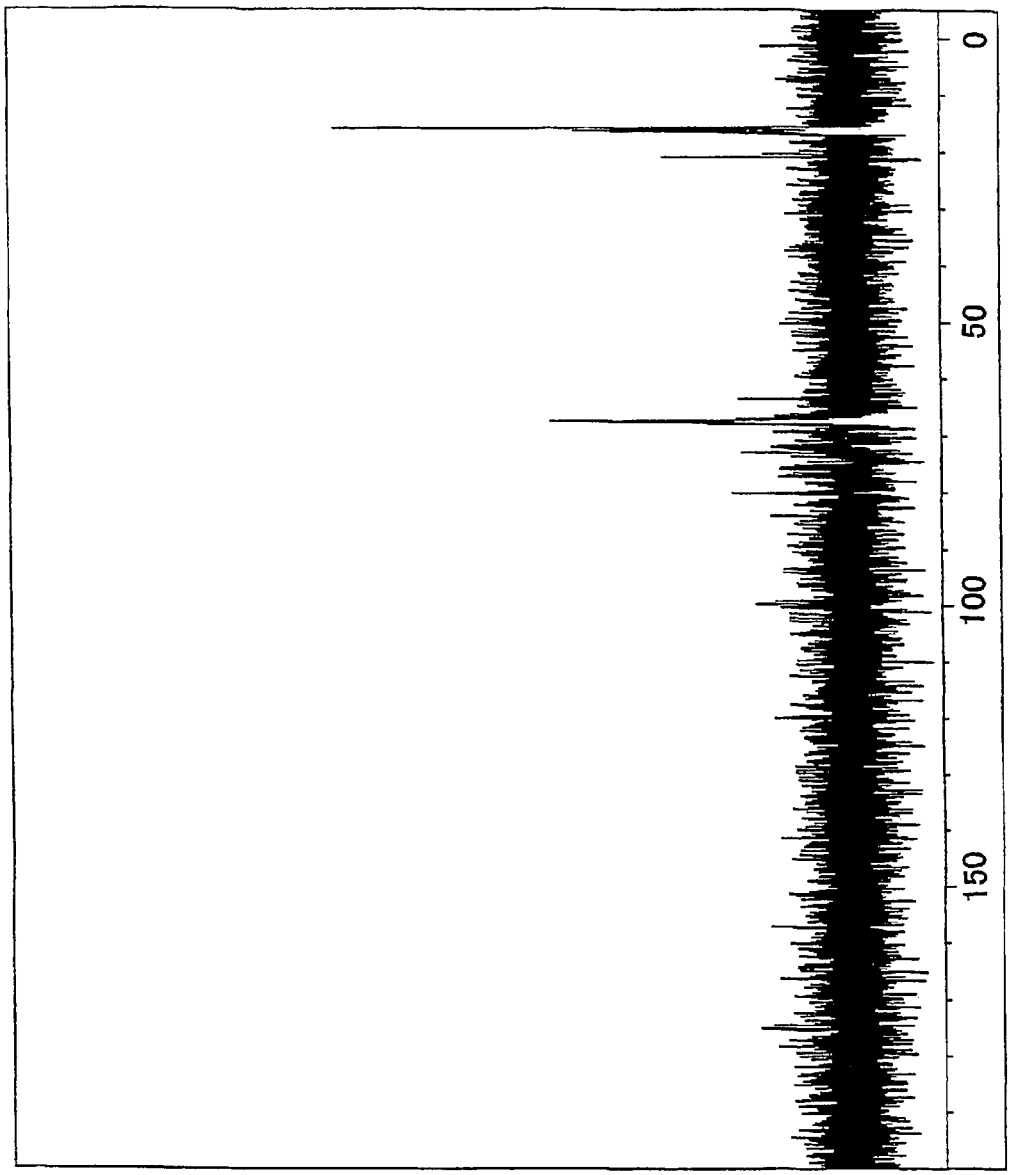
Figure 40:
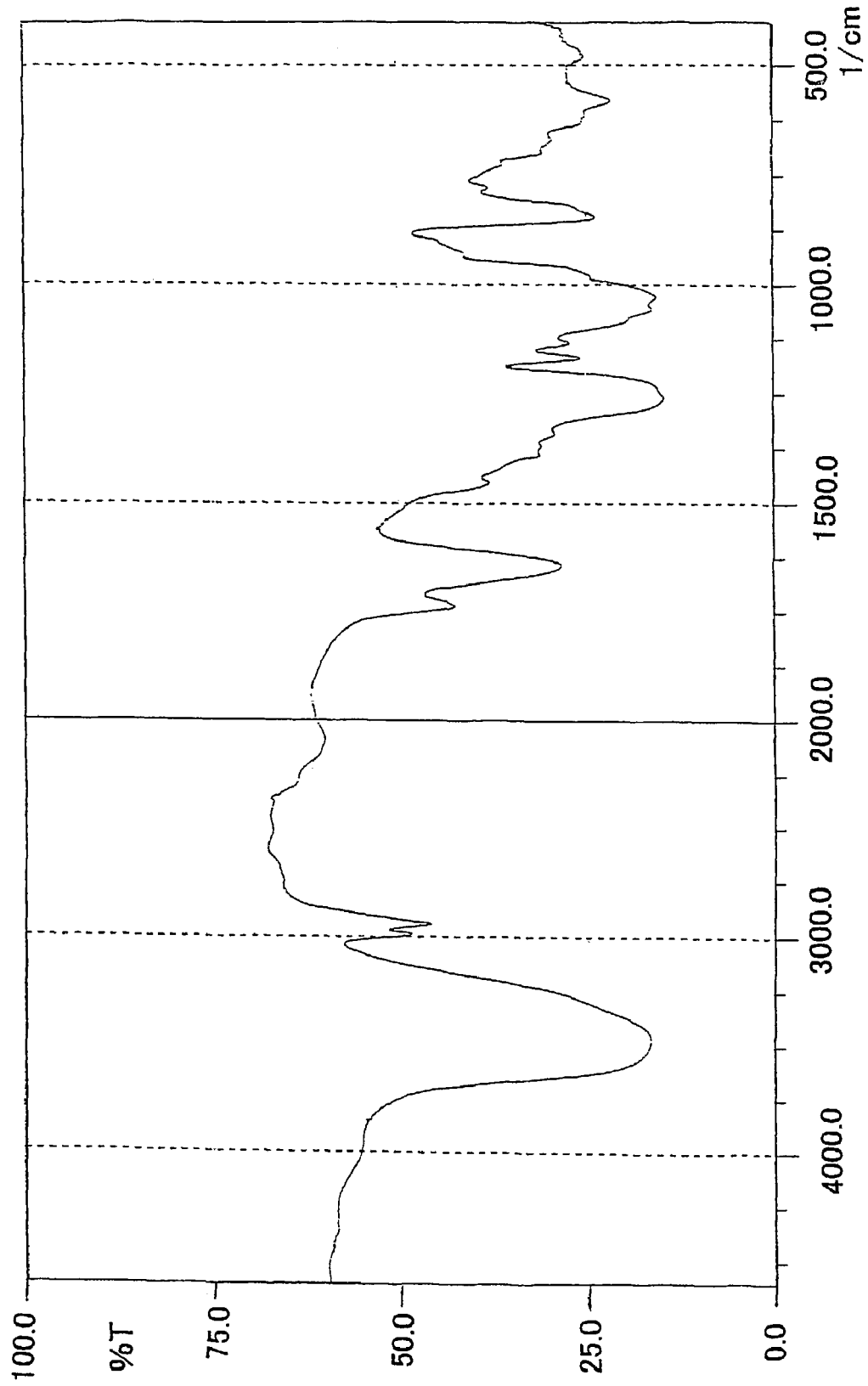
FIG. 40: a figure which illustrates the infrared absorption spectrum thereof.

(1) Analysis of Main Structure of the Sulfated Glucuronofucan of the Present Invention NMR analyses were carried out in order to determine the whole structure of the purified sulfated glucuronofucan fraction prepared in Example 7 and the site of cleavage by the sulfated glucuronofucan-degrading enzyme. The results for identification in NMR are shown below. The $^1$H-NMR spectrum and $^{13}$C-NMR spectrum of the sulfated glucuronofucan of the present invention are illustrated in FIGS. 38 and 39, respectively. In FIGS. 38 and 39, the vertical axes represent the signal intensity and the horizontal axes represent the chemical shift value (ppm). Furthermore, the infrared absorption spectrum is illustrated in FIG. 40. In FIG. 40, the vertical axis represents the transmissivity (%) and the horizontal axis represents the wave number ($cm^{-1}$). Results of $^1$H-NMR and $^{13}$C-NMR analyses are shown in Table 14.

TABLE 14

| | Chemical shift value (ppm) | |
|---|---|---|
| | $^{13}$C-NMR | $^1$H-NMR |
| F1-1 | 94.8 | 5.03 |
| F1-2 | 71.0 | 4.10 |
| F1-3 | 72.0 | 4.20 |
| F1-4 | 69.4 | 5.31 |
| F1-5 | 66.8 | 4.33 |
| F1-6 | 15.4 | 1.01 |
| CH$_3$ of acetyl group | 20.5 | 2.07 |
| CO of acetyl group | 175.0 | — |
| CH$_3$ | 20.5 | 2.07 |
| F2-1 | 94.5 | 5.01 |
| F2-2 | 67.0 | 3.85 |
| F2-3 | 76.6 | 3.85 |
| F2-4 | 80.0 | 4.63 |
| F2-5 | 66.9 | 4.33 |
| F2-6 | 16.0 | 1.10 |
| F3-1 | 99.2 | 4.96 |
| F3-2 | 67.0 | 3.80 |
| F3-3 | 76.6 | 3.88 |
| F3-4 | 80.0 | 4.63 |
| F3-5 | 66.9 | 4.24 |
| F3-6 | 16.0 | 1.10 |
| F4-1 | 99.2 | 4.96 |
| F4-2 | 67.2 | 3.73 |
| F4-3 | 74.7 | 3.85 |
| F4-4 | 68.7 | 3.95 |
| F4-5 | 67.4 | 4.18 |
| F4-6 | 16.0 | 1.10 |
| GA1-1 | 99.6 | 5.18 |
| GA1-2 | 71.2 | 3.47 |
| GA1-3 | 72.4 | 3.63 |
| GA1-4 | 71.8 | 3.42 |
| GA1-5 | 72.6 | 3.87 |
| GA1-6 | 177.0 | — |

The identification results in Table 14 showed that the sulfated glucuronofucan of the present invention has a structure in which a fucose F1 is linked through an α-bond to 3-position of a fucose F4 in another repeated pentasaccharide as shown in formula (XV) below. Furthermore, it was confirmed that one residue of acetyl group is attached mainly to 4-position of a fucose F1 in a repeated pentasaccharide. Specifically, it was shown that the sulfated glucuronofucan has a structure in which the following main backbone is repeated.

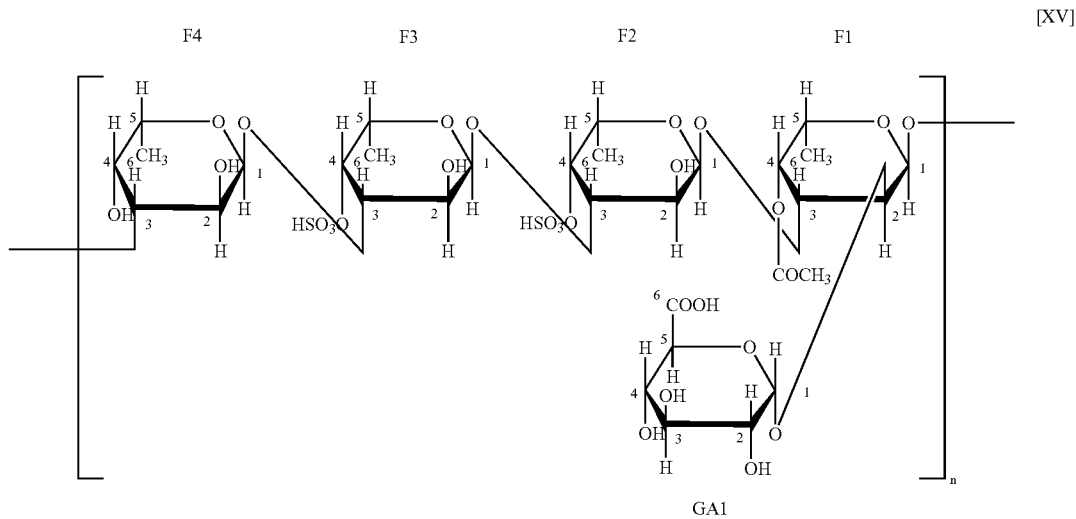

INDUSTRIAL APPLICABILITY

The present invention provides a novel fucoidan deacetylase, a novel α-D-glucuronidase and a novel endo-α-L-fucosidase which can be used for structural analysis of a sulfated glucuronofucan and reproducible production of smaller molecules from a sulfated glucuronofucan. The present invention also provides methods for producing the enzymes. By using the enzyme, deacetylated sulfated glucuronofucans deacetylated to varying degrees, deacetylated deglucuronylated sulfated glucuronofucans deglucuronylated to varying degrees and sulfated glucuronofucan oligosaccharides, which are useful as reagents for glycotechnology, are provided. Furthermore, an additive for efficient utilization of the enzyme is provided. Also, a microorganism producing enzymes that degrades sulfated polysaccharides derived from various brown algae is provided.

Sequence Listing Free Text

SEQ ID NO:1: Designed oligonucleotide primer to amplify 16S rDNA region.

SEQ ID NO:2: Designed oligonucleotide primer to amplify 16S rDNA region.

---

The invention claimed is:
1. A saccharide having a chemical structure of one selected from the group consisting of general formulas (I) to (III), or a salt thereof:
[I]
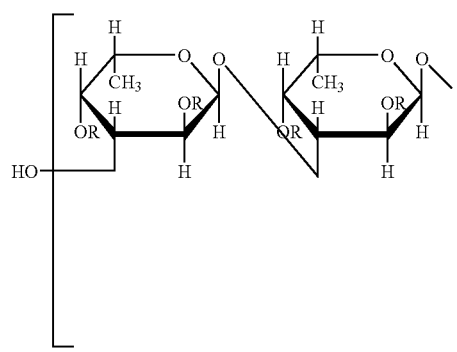
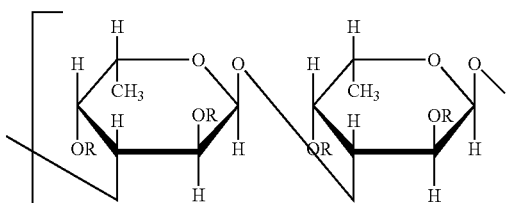
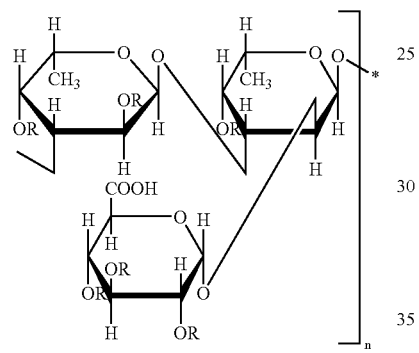
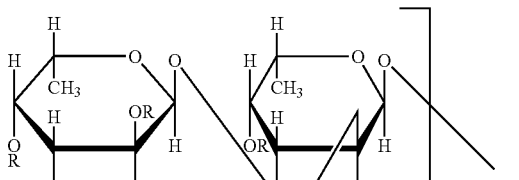
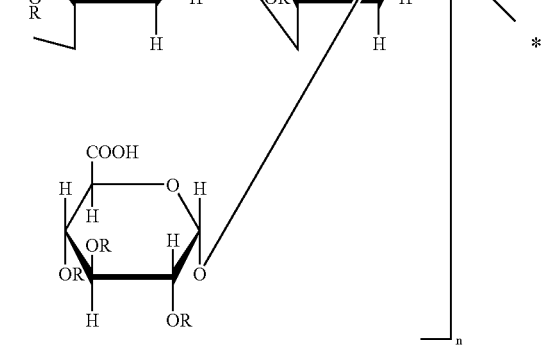
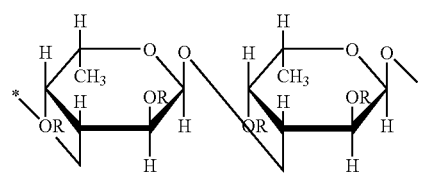
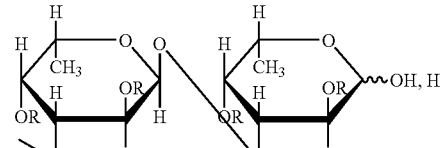
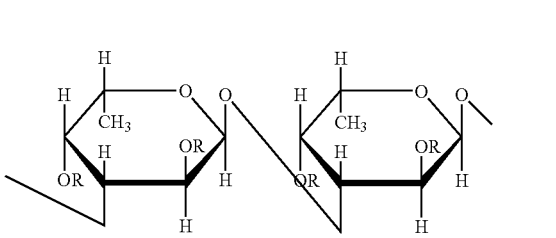
[II]
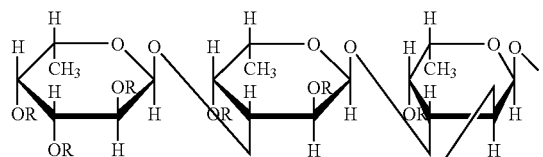
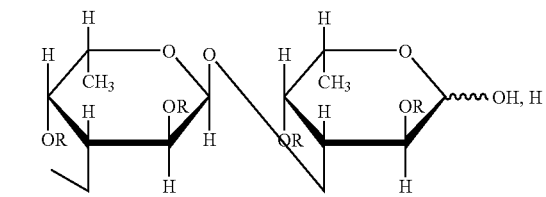
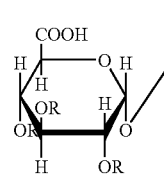

-continued

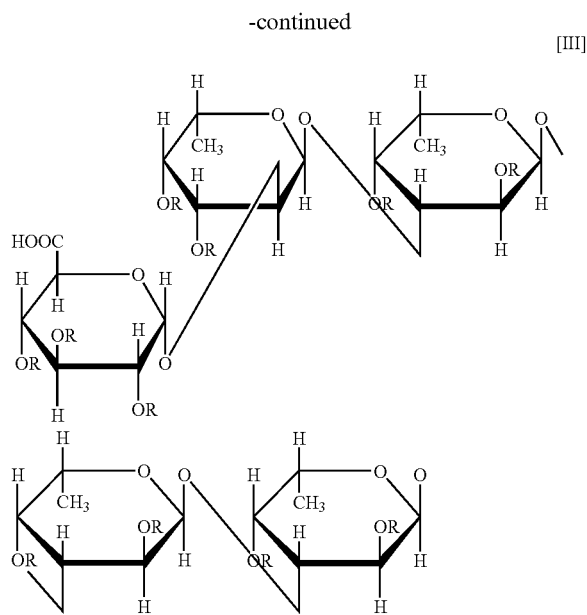
[III]

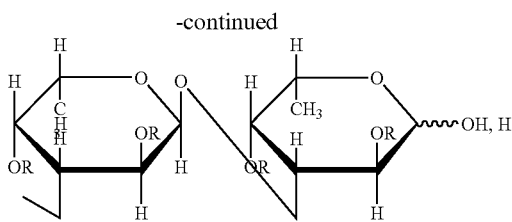

wherein R is H, SO₃H or CH₃CO; n is 0 or an integer of 1 or more.

2. A sulfated glucuronofucan having the following chemical and physical properties, or a salt thereof:

(1) containing fucose and glucuronic acid as constituting saccharides at a molar ratio of 35:10 to 44:10; and (2) containing a sulfated saccharide of general formula (VIII) as an essential component of the constituting saccharides:

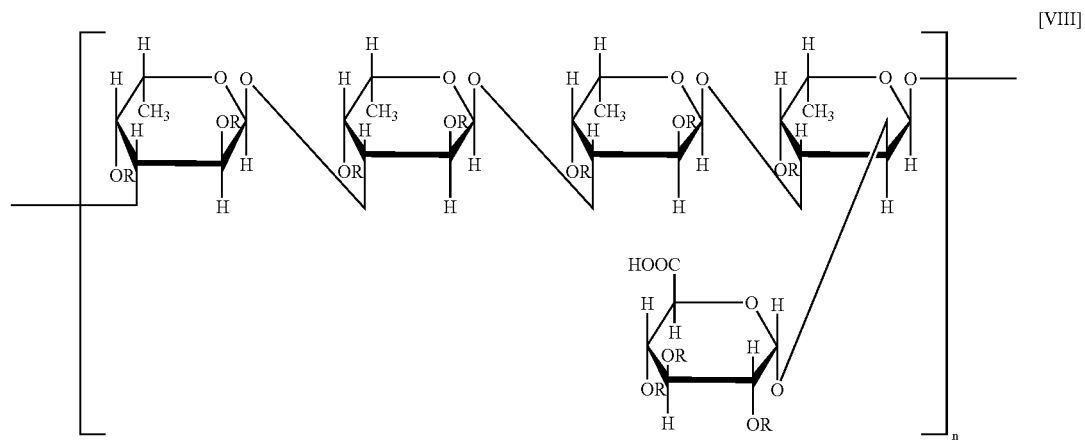
[VIII]

3. The sulfated glucuronofucan according to claim 2, wherein n is from 1 to 5000.

* * * * *